(12) United States Patent
Buesing et al.

(10) Patent No.: US 9,409,883 B2
(45) Date of Patent: Aug. 9, 2016

(54) MATERIALS FOR ORGANIC ELECTROLUMINESCENT DEVICES

(75) Inventors: Arne Buesing, Frankfurt am Main (DE); Holger Heil, Frankfurt am Main (DE); Teresa Mujica-Fernaud, Darmstadt (DE); Irina Martynova, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 1045 days.

(21) Appl. No.: 13/575,697

(22) PCT Filed: Dec. 28, 2010

(86) PCT No.: PCT/EP2010/007955
§ 371 (c)(1),
(2), (4) Date: Jul. 27, 2012

(87) PCT Pub. No.: WO2011/091840
PCT Pub. Date: Aug. 4, 2011

(65) Prior Publication Data
US 2012/0292571 A1 Nov. 22, 2012

(30) Foreign Application Priority Data
Jan. 29, 2010 (DE) .......................... 10 2010 006 121

(51) Int. Cl.
| | | |
|---|---|---|
| *H01L 51/54* | (2006.01) | |
| *C09K 11/06* | (2006.01) | |
| *C07D 401/10* | (2006.01) | |
| *H01L 51/00* | (2006.01) | |
| *C07F 1/02* | (2006.01) | |
| *C07F 5/06* | (2006.01) | |
| *C07D 401/14* | (2006.01) | |
| *C07D 413/10* | (2006.01) | |
| *C07D 417/10* | (2006.01) | |
| *H01L 51/50* | (2006.01) | |

(52) U.S. Cl.
CPC ............ *C07D 401/10* (2013.01); *C07D 401/14* (2013.01); *C07D 413/10* (2013.01); *C07D 417/10* (2013.01); *C07F 1/02* (2013.01); *C07F 5/069* (2013.01); *H01L 51/0081* (2013.01); *H01L 51/5072* (2013.01)

(58) Field of Classification Search
CPC .. C07D 401/10; C07D 401/14; C07D 413/10; C07D 417/10; H01L 51/008; H01L 51/0081; H01L 51/009; H01L 51/0091; H01L 51/0092; C07F 1/005; C07F 1/008; C07F 3/003; C07F 5/022; C07F 5/06; C07F 5/069; C07F 7/006
USPC ............................................ 546/7
See application file for complete search history.

(56) References Cited

U.S. PATENT DOCUMENTS

| | | |
|---|---|---|
| 4,539,507 A | 9/1985 | VanSlyke et al. |
| 5,151,629 A | 9/1992 | VanSlyke |

FOREIGN PATENT DOCUMENTS

| | | | |
|---|---|---|---|
| CN | 101165137 A | 4/2008 | |
| CN | 101168661 A | 4/2008 | |
| EP | 0825803 A2 | 2/1998 | |
| JP | 2003/077671 A | * 3/2003 | ............ H05B 33/14 |
| WO | WO-03/060953 A2 | 7/2003 | |

OTHER PUBLICATIONS

English language machine translation of JP 2003/077671 A, 2003.*
English language translation of CN 101168661 A, 2008.*
Cui et al. J. Org. Chem. 2006, 71, 6485-6496. Year of publication: 2006.*
International Search Report of corresponding PCT application PCT/EP2010/007955 mailed Aug. 4, 2011.

* cited by examiner

*Primary Examiner* — Andrew K Bohaty
(74) *Attorney, Agent, or Firm* — Drinker Biddle & Reath LLP

(57) ABSTRACT

The present invention relates to coordination compounds which are used in an electron-transport layer in electronic devices, to ligands, and to the use thereof for the preparation of metal complexes, to a layer, and to an electronic device which comprise the compounds according to the invention, and to a process for the preparation of the compounds according to the invention.

16 Claims, No Drawings

MATERIALS FOR ORGANIC ELECTROLUMINESCENT DEVICES

RELATED APPLICATIONS

This application is a national stage application (under 35 U.S.C. §371) of PCT/EP2010/007955, filed Dec. 28, 2010, which claims benefit of German Patent Application No. 10 2010 006 121.2, filed Jan. 25, 2010.

The present invention relates to coordination compounds of the general formulae (1) to (21), in particular as materials in the electron-transport layer in electronic devices, to ligands of the general formula (1'), to a process for the preparation thereof, and to the use thereof for the preparation of a metal complex, to a layer, and to an electronic device which comprise the compounds according to the invention.

Chelate complexes and organometallic compounds are used as functional materials in a number of different applications which can be ascribed to the electronics industry in the broadest sense. In spite of the successes that have already been achieved, further improvements are still desirable in the case of the organic electroluminescent devices based on organic components (general description of the structure cf. U.S. Pat. No. 4,539,507 and U.S. Pat. No. 5,151,629) and the individual components thereof, the organic light-emitting diodes (OLEDs).

There is also a need for improvement in the case of, in particular, the electron-transport materials used hitherto with respect to their lifetime and efficiency. A further requirement of materials used in OLEDs is that they have a high degree of purity. A high glass transition temperature of these compounds and a low tendency towards crystallisation are highly desired. Furthermore, there is a need for improvement in the case of materials which are processed from solution.

At present, a large number of electron-transport materials is available. Thus, for example, WO 2003/060956 describes 9,10-diarylanthracene derivatives which carry a benzimidazole group in the structure as electron-transport materials. In addition, 8-hydroxyquinoline-metal complexes, whose influence on emission spectra has been studied by changing the substitution pattern, are known, for example, from Chem. Eur. J. 2006, 12, 4523.

Frequently, either an electron-transport layer and an adjacent electron-injection layer are used on the cathode side of an OLED, or a mixture of an electron-transport material and an electron-injection material is used in a layer. The electron-injection materials used here include, inter alia, metal complexes, such as, for example, Liq (lithium quinolinate). It would be desirable if it were possible to use only one layer consisting of one material here instead of using two materials in a mixture or in successive layers. This would simplify production and enable better process control since vapour deposition does not have to be carried out from two sources.

There is therefore a need for novel compounds which have improved properties, in particular with respect to the above-mentioned problems. The object of the invention thus consisted in the provision of such compounds.

Surprisingly, it has been found that complexes containing hydroxyquinoline derivatives as ligands which contain an electron-deficient heteroaryl group covalently bonded via an aromatic system achieve a long operating lifetime and/or high stability to temperature stresses compared with the compounds already presented in the prior art. The said compounds can furthermore be processed well from solution and can be employed in an OLED without the use of a separate electron-injection layer.

In order to achieve the said object, the present invention provides a compound of the general formula (1) or (2):

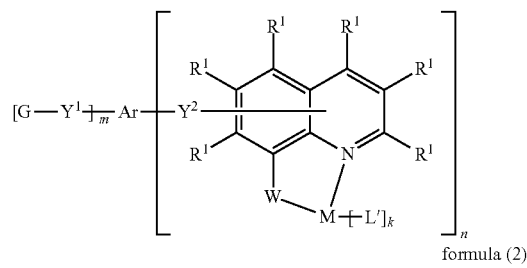

formula (1)

formula (2)

The symbols and indices used in formula (1) or (2) have the following meanings:

G is, identically or differently on each occurrence, a group of the following formula (a), (b) or (c):

formula (a)

formula (b)

formula (c)

Q is selected, identically or differently on each occurrence, from the group consisting of N and $CR^3$;

V is selected from the group consisting of O, S, N, $CR^4$ and $NR^4$, with the proviso that, if V is equal to O, S or $NR^4$, $R^3$ represents a non-bonding electron pair;

the two dashed bonds in formula (a) and (b) mean that one of the bonds is a single covalent bond and the other is a double covalent bond;

$R^1$ is selected, identically or differently on each occurrence, from the group defined for $R^2$, $R^3$ or $R^4$; where one $R^1$ is not present, and the quinoline unit is bonded to $Y^2$ at this position;

$R^2$, $R^3$, $R^4$ are selected, identically or differently on each occurrence, from the group consisting of H, D, F, Cl, Br, I, CHO, N(Ar$^1$)$_2$, C(=O)Ar$^1$, P(=O)(Ar$^1$)$_2$, S(=O)Ar$^1$, S(=O)$_2$Ar$^1$, OR$^5$=OR$^5$Ar$^1$, CN, NO$_2$, Si(R$^5$)$_3$, B(OAr$^1$)$_2$, B(OR$^5$)$_2$, OSO$_2$R$^5$, OH, a saturated or unsaturated, straight-chain, branched or cyclic C$_{1-40}$-alkyl group, C$_{1-40}$-alkoxy group or C$_{1-40}$-thioalkyl group, each of which may be substituted by one or more radicals R$^5$, where one or more non-adjacent CH$_2$ groups may be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$, and where one or more H atoms may be replaced by D, F, Cl, Br, I, CN or NO$_2$, an aromatic or heteroaromatic ring system having 5 to 60 aromatic ring atoms, which may be substituted by one or more radicals R$^6$, an aryl-oxy or heteroaryloxy group having 5 to 60 aromatic ring atoms, which may be substituted by one or more radicals R$^6$, and a combination of these systems; where one of the substituents R$^2$, R$^3$ or R$^4$ is not present on the group G, and the group G is bonded to Y$^1$ at this position;

W is selected, identically or differently on each occurrence, from O, S and NR$^8$, where R$^8$ is selected from the group defined for R$^2$, R$^3$ or R$^4$;

Y$^1$, Y$^2$ are each, independently of one another, either not present, so that the groups bonded thereto are linked directly to one another by a single covalent bond, or are selected from the group consisting of a saturated or unsaturated, linear, branched or cyclic C$_{1-40}$-alkyl group and an aromatic or heteroaromatic ring system having 5 to 60 ring atoms, which may be substituted by one or more radicals R$^6$;

Ar is an aromatic or heteroaromatic ring system having 5 to 60 aromatic ring atoms, which may be substituted by one or more radicals R$^9$, where R$^9$ is selected from the group defined for R$^2$, R$^3$ or R$^4$;

Ar$^1$ is, identically or differently on each occurrence, an aromatic or heteroaromatic ring system having 5 to 30 aromatic ring atoms, which may be substituted by one or more radicals R$^7$, where, in addition, two radicals Ar$^1$ which are bonded to the same nitrogen or phosphorus atom may be linked to one another by a single bond or a bridge selected from B(R$^7$), C(R$^7$)$_2$, Si(R$^7$)$_2$, C=O, C=NR$^7$, C=C(R$^7$)$_2$, O, S, S=O, SO$_2$, N(R), P(R$^7$) and P(=O)R$^7$;

R$^5$ is selected, identically or differently on each occurrence, from the group consisting of H, D, a saturated or unsaturated, linear, branched or cyclic C$_{1-20}$-alkyl group, in which one or more H atoms may be replaced by D or F, and an aromatic or heteroaromatic ring system having 5 to 20 ring atoms, in which one or more H atoms may be replaced by F, and which may be substituted by one or more radicals R$^6$;

R$^6$ is selected, identically or differently on each occurrence, from the group consisting of H, D, F, Cl, Br, I, CHO, N(Ar$^1$)$_2$, C(=O)Ar$^1$, P(=O)(Ar$^1$)$_2$, S(=O)Ar$^1$, S(=O)$_2$Ar$^1$, CR$^7$=CR$^7$Ar$^1$, CN, NO$_2$, Si(R$^7$)$_3$, B(OAr$^1$)$_2$, B(OR$^7$)$_2$, OSO$_2$R$^7$, OH, and a saturated or unsaturated, straight-chain, branched or cyclic C$_{1-40}$-alkyl group, C$_{1-40}$-alkoxy group or C$_{1-40}$-thioalkyl group, each of which may be substituted by one or more radicals R$^7$, where one or more non-adjacent CH$_2$ groups may be replaced by R$^7$C=CR$^7$, C≡C, Si(R$^7$)$_2$, Ge(R$^7$)$_2$, Sn(R$^7$)$_2$, C=O, C=S, C=Se, C=NR$^7$, P(=O)(R$^7$), SO, SO$_2$, NR$^7$, O, S or CONR$^7$, and where one or more H atoms may be replaced by D, F, Cl, Br, I, CN or NO$_2$, R$^7$ is selected, identically or differently on each occurrence, from the group consisting of H, D, a saturated or unsaturated, linear, branched or cyclic C$_{1-20}$-alkyl group, in which one or more H atoms may be replaced by F or D, and an aromatic or heteroaromatic ring system having 5 to 20 ring atoms, in which one or more H atoms may be replaced by F or D;

M is, identically or differently on each occurrence, a mono-, di-, tri- or tetravalent metal;

L' is, identically or differently on each occurrence, a monodentate or bidentate ligand;

m is, identically or differently on each occurrence, 0, 1, 2, 3 or 4, with the proviso that at least one index m is >0;

n is 1, 2, 3 or 4;

r is 1, 2, 3 or 4;

k is, identically or differently on each occurrence, 0, 1, 2, 3, 4, 5 or 6; and l is 0, 1, 2, 3, 4, 5 or 6.

The following general definitions are used within this invention:

For the purposes of the present invention, a saturated or unsaturated, straight-chain, branched or cyclic C$_{1-20}$-alkyl group or C$_{1-40}$-alkyl group is taken to mean an alkyl, alkenyl and alkynyl groups having 1 to 20 or 1 to 40 C atoms respectively. Individual —CH— or —CH$_2$— groups may be substituted by N, NH, O or S. Preference is given to the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, cyclohexyl, neohexyl, n-heptyl, cycloheptyl, n-octyl, cyclooctyl, 2-ethylhexyl, trifluoromethyl, pentafluoro-ethyl, 2,2,2-trifluoroethyl, ethenyl, propenyl, butenyl, pentenyl, cyclo-pentenyl, hexenyl, cyclohexenyl, heptenyl, cycloheptenyl, octenyl, cyclo-octenyl, ethynyl, propynyl, butynyl, pentynyl, hexynyl, heptynyl or octynyl. Particular preference is given to alkyl groups having 1 to 6 carbon atoms, even more preferably having 1 to 4 carbon atoms, in particular methyl and tert-butyl.

Aliphatic hydrocarbons having 1 to 20 carbon atoms are linear, branched or cyclic alkyl groups, alkenyl groups, alkynyl groups, in which one or more carbon atoms may be replaced by O, N or S. In addition, one or more hydrogen atoms may be replaced by fluorine. Examples of aliphatic hydrocarbons having 1 to 20 carbon atoms include the same ones as defined above for the alkyl, alkenyl and alkynyl groups.

A C$_{1-40}$-alkoxy group or C$_{1-40}$-thioalkyl group is taken to mean a C$_{1-40}$-alkyl group as defined above which is bonded via an O or S atom. Preference is given to alkoxy groups having 1 to 20 carbon atoms, particularly preferably 1 to 6 carbon atoms, extraordinarily preferably 1 to 4 carbon atoms.

The alkyl groups, alkoxy groups and thioalkyl groups may, in addition, be substituted by one or more radicals R$^5$ as defined above.

An aromatic or heteroaromatic ring system having 5 to 60, or 5 to 30 ring atoms, or 5 to 20 ring atoms in the sense of this invention is taken to mean an aromatic ring system having 6 to 60, or 6 to 30, or 6 to 20 carbon atoms respectively, or a heteroaromatic ring system having 5 to 60, or 5 to 30, or 5 to 20 carbon atoms respectively, one or more carbon atoms of which may be substituted by a heteroatom. Preferred heteroatoms are N, O and S. These aromatic ring systems may be monocyclic or polycyclic, i.e. they may have one ring (for example phenyl) or two or more rings (for example biphenyl, fluorenyl), which may also be in condensed form (for example naphthyl).

Preference is given to aromatic or heteroaromatic ring systems having 5 to 30 aromatic ring atoms, particularly preferably 5 to 24 aromatic ring atoms, more preferably 5 to 14 aromatic ring atoms. Preferred aromatic ring systems having 6 to 60, or 6 to 30, or 6 to 24 carbon atoms respectively are, for example, phenyl, naphthalene, anthracene, benzanthracene, phenanthrene, benzophenanthrene, pyrene, benzopyrene, chrysene, perylene, biphenyl, terphenyl, fluorene, spirobifluorene, indene, indenofluorene, benzindenofluorene, dibenzindenofluorene or fluoranthene.

Preferred heteroaromatic ring systems having 5 to 60, or 5 to 30, or 5 to 24 ring atoms respectively are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalin-imidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, benzothiadiazothiophene, or combinations of these groups. Particular preference is given to imidazole, benzimidazole, pyridine, pyrimidine and triazine The mono- or polycyclic aromatic or heteroaromatic ring systems having 5 to 60 ring atoms may carry one or more substituents which are defined above under $R^6$.

An aryloxy or heteroaryloxy group having 5 to 60 aromatic ring atoms is taken to mean a group which carries a mono- or polycyclic aromatic or heteroaromatic ring system having 5 to 60 ring atoms as defined above via an O atom. Preference is given to aryloxy or heteroaryloxy groups having 5 to 30 aromatic ring atoms, particularly preferably 5 to 20 ring atoms, more preferably 5 to 10 ring atoms. The aryloxy or heteroaryloxy group may likewise carry one or more substituents which are defined above under $R^6$.

M is preferably an element, a metal or a metal ion selected from the group consisting of alkali metal, alkaline-earth metal, boron group and sub-group elements. M is particularly preferably a metal or a metal ion of an element selected from the group consisting of Li, Be, Ca, Mg, Ba, Zn, B, Al, Zr, Cu, Sc and Y, extraordinarily preferably Li, Ca, Mg, Zn, Al and Zr.

The following applies to compounds of the formula (1) which are preferred in accordance with the invention:

If M is a metal having two coordination sites, then k is equal to 0;
if M is a metal having three coordination sites and L' is a monodentate ligand, then k is equal to 1;
if M is a metal having four coordination sites and L' is a monodentate ligand, then k is equal to 2;
if M is a metal having five coordination sites and L' is a monodentate ligand, then k is equal to 3;
if M is a metal having six coordination sites and L' is a monodentate ligand, then k is equal to 4;
if M is a metal having seven coordination sites and L' is a monodentate ligand, then k is equal to 5;
if M is a metal having eight coordination sites and L' is a monodentate ligand, then k is equal to 6;
if M is a metal having four coordination sites and L' is a bidentate ligand, then k is equal to 1;
if M is a metal having six coordination sites and L' is a bidentate ligand, then k is equal to 2;
if M is a metal having eight coordination sites and L' is a bidentate ligand, then k is equal to 3.

The following applies to compounds of the formula II which are preferred in accordance with the invention:
if M is a metal having two coordination sites and r is equal to 1, then l is equal to 0;
if M is a metal having three coordination sites, L' is a monodentate ligand and r is equal to 1, then l is equal to 1;
if M is a metal having four coordination sites, L' is a monodentate ligand and r is equal to 1, then l is equal to 2;
if M is a metal having five coordination sites, L' is a monodentate ligand and r is equal to 1, then l is equal to 3;
if M is a metal having six coordination sites, L' is a monodentate ligand and r is equal to 1, then l is equal to 4;
if M is a metal having seven coordination sites, L' is a monodentate ligand and r is equal to 1, then l is equal to 5;
if M is a metal having eight coordination sites, L' is a monodentate ligand and r is equal to 1, then l is equal to 6;
if M is a metal having four coordination sites and r is equal to 2, then l is equal to 0;
if M is a metal having five coordination sites, L' is a monodentate ligand and r is equal to 2, then l is equal to 1;
if M is a metal having six coordination sites, L' is a monodentate ligand and r is equal to 2, then l is equal to 2;
if M is a metal having seven coordination sites, L' is a monodentate ligand and r is equal to 2, then l is equal to 3;
if M is a metal having eight coordination sites, L' is a monodentate ligand and r is equal to 2, then l is equal to 4;
if M is a metal having six coordination sites and r is equal to 3, then l is equal to 0;
if M is a metal having seven coordination sites, L' is a monodentate ligand and r is equal to 3, then l is equal to 1;
if M is a metal having eight coordination sites, L' is a monodentate ligand and r is equal to 3, then l is equal to 2;
if M is a metal having eight coordination sites and r is equal to 4, then l is equal to 0;
if M is a metal having four coordination sites, L' is a bidentate ligand and r is equal to 1, then l is equal to 1;
if M is a metal having six coordination sites, L' is a bidentate ligand and r is equal to 1, then l is equal to 2;
if M is a metal having eight coordination sites, L' is a bidentate ligand and r is equal to 1, then l is equal to 3;
if M is a metal having six coordination sites, L' is a bidentate ligand and r is equal to 2, then l is equal to 1;
if M is a metal having eight coordination sites, L' is a bidentate ligand and r is equal to 2, then l is equal to 2;
if M a metal having eight coordination sites, L' a bidentate ligand and r equal to 3, then l is equal to 1;
if M a metal having eight coordination sites, La bidentate ligand and r equal to 4, then l is equal to 0.

It is particularly preferred in accordance with the invention for M to be a metal having two, four or six coordination sites. In an extraordinarily preferred embodiment, M is equal to $Li^+$, $Al^{3+}$ or $Zr^{4+}$, in particular $Li^+$ or $Al^{3+}$.

In a further embodiment of the present invention, it is preferred for the group Ar to be selected from the following formulae:

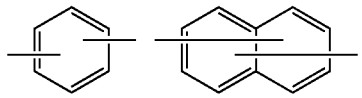

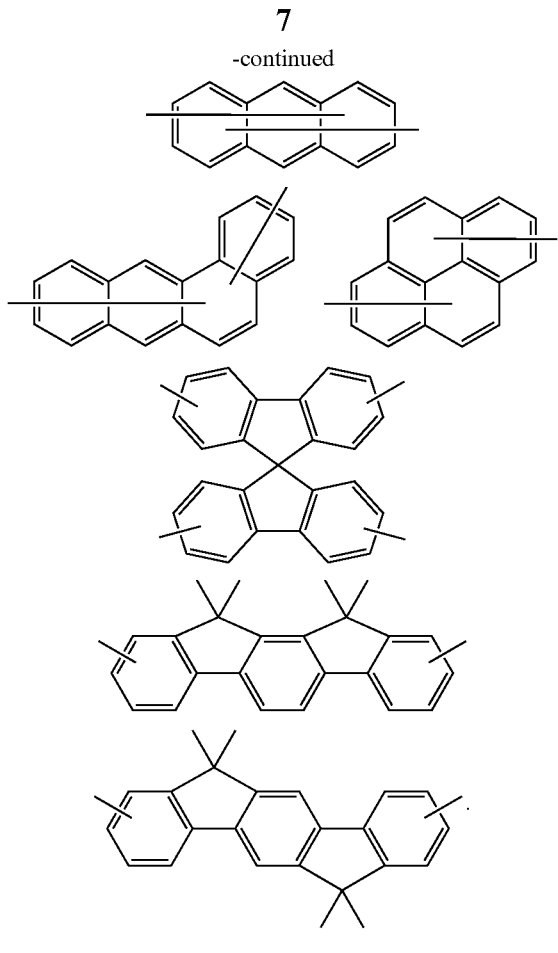

These groups may each also be substituted by one or more radicals $R^9$.

In a further embodiment of the present invention, it is preferred for the group G to be selected from the following formulae:

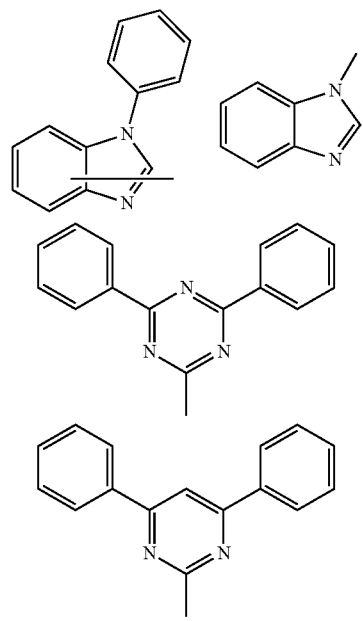

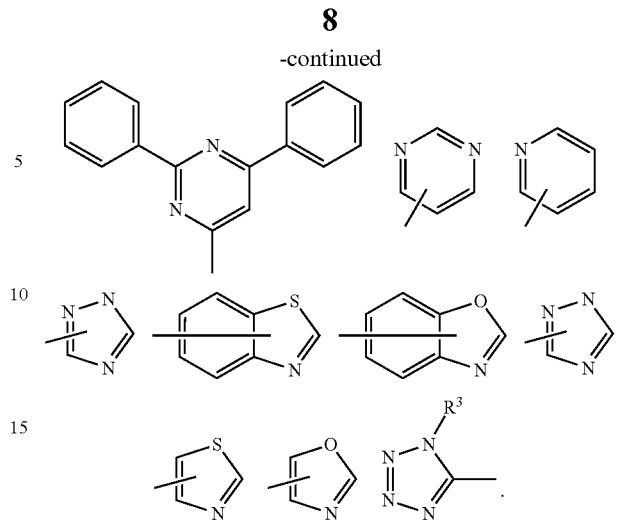

These structures may also be substituted by one or more substituents $R^2$, $R^3$ or $R^4$.

In a further embodiment of the present invention, it is preferred for the groups $Y^1$ and $Y^2$, identically or differently on each occurrence, not to be present or to be selected from the following groups:

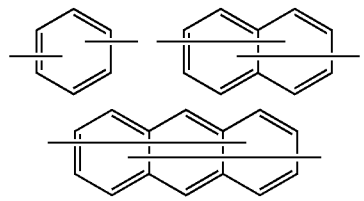

These structures may also be substituted by one or more substituents $R^6$.

In a further embodiment of the present invention, it is preferred for the compound of the formula (1) or (2) according to the invention to be a compound of the following formulae (3) to (12):

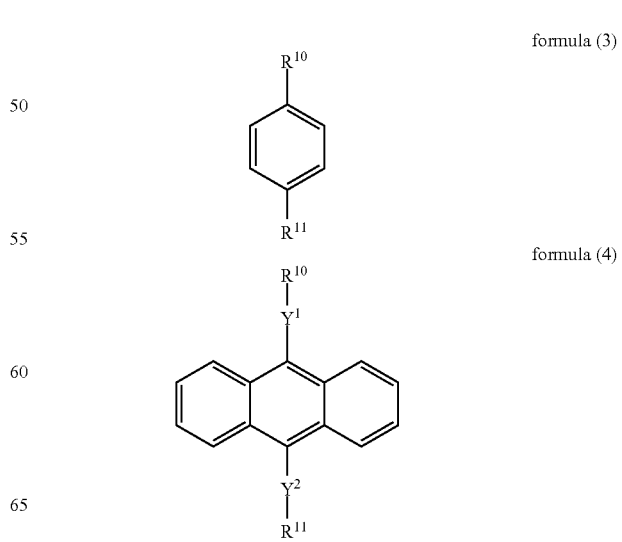

formula (3)

formula (4)

formula (5)
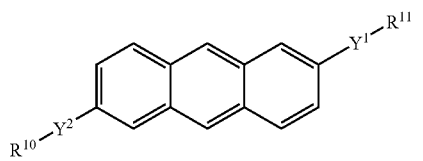

formula (6)
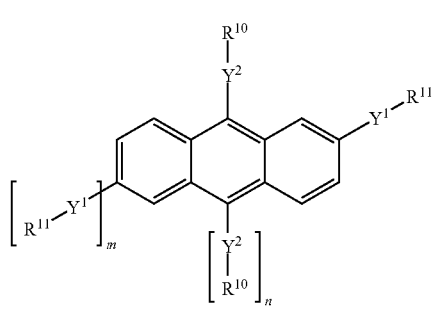

formula (7)
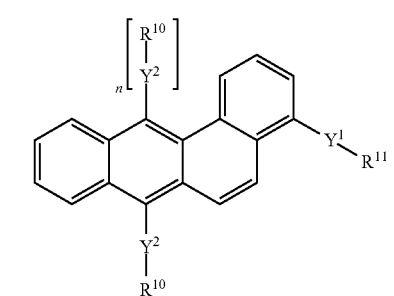

formula (8)
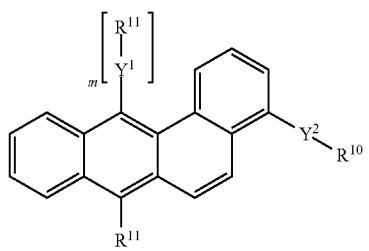

formula (9)
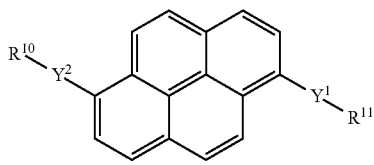

formula (10)
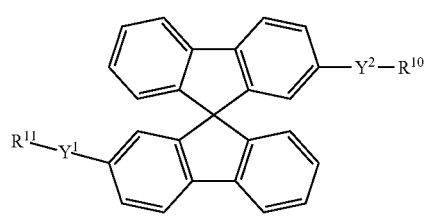

formula (11)
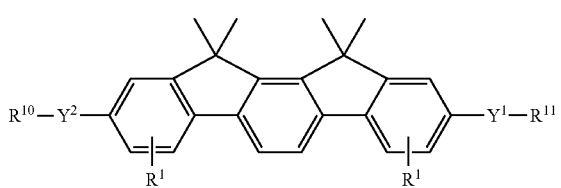

formula (12)
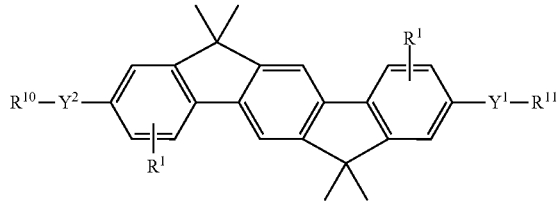

where the symbols used have the following meanings:
$Y^1$ and $Y^2$ have the same meaning as in the above embodiments;
$R^{10}$ is, identically or differently on each occurrence, either H or a radical of the following formula (d):

formula (d)
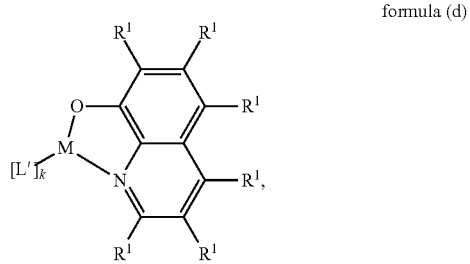

where L', k and $R^1$ have the same meanings as in the above embodiments, with the proviso that one $R^1$ is not present, and the compound of the formula (d) is bonded to the compound of the formula (3) to (12) at this position;
$R^{11}$ is, identically or differently on each occurrence, either H or a radical of the following formula (e) or (f):

formula (e)
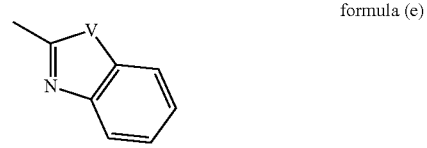

formula (f)

where V is selected from the group consisting of O, S and $NR^4$ and Q is selected from the group consisting of N and $CR^3$, where at least one Q, preferably at least two Q, stand for N and where $R^3$ has the same meaning as in the above embodiments;
with the proviso that both at least one $R^{10}$ in each formula and also at least one $R^{11}$ in each formula is other than H.

In still a further embodiment of the present invention, the compound of the above-mentioned formulae is a compound in which $Y^1$ and $Y^2$ is each not present or is a p-phenylene unit, V is an —N-Ph radical and $R^1$ is equal to H or D, with the proviso that either the $R^1$ which is in the ortho position to the metal-coordinated oxygen atom in the compound of the formula (d) or the $R^1$ which is in the para position to the metal-coordinated oxygen atom in the compound of the formula (d) is not present, and the compound of the formula (d) is bonded via this position.

It is furthermore preferred for two or three symbols Q in the group of the formula (f) to stand for N. The group of the formula (f) is particularly preferably a 1,3,5-triazine.

In a preferred embodiment of the invention, $R^{10}$ is selected from the following formulae, where the bond drawn in indicates the position of the link to $Y^2$:

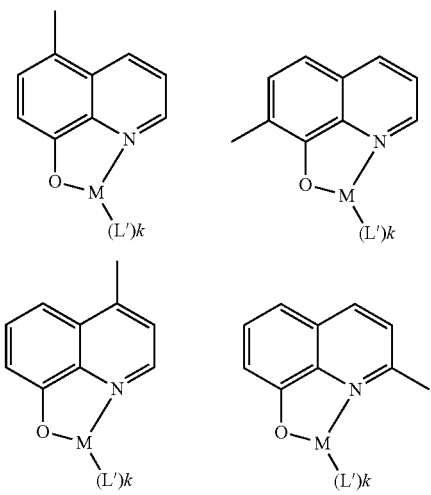

Furthermore, m in all embodiments according to the invention is preferably equal to 1 or 2.

In addition, n in all embodiments according to the invention is preferably equal to 1, 2 or 3.

The object according to the invention is also achieved by a compound, an oligomer or a polymer which contains a structural unit of the general formula (13) to (21):

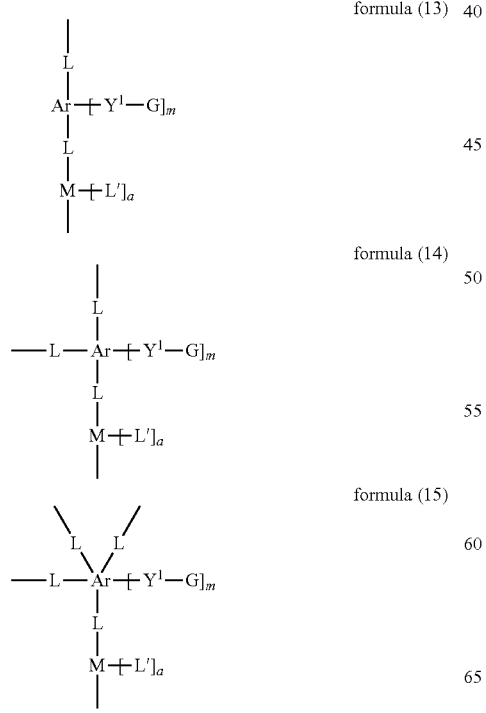

formula (13)

formula (14)

formula (15)

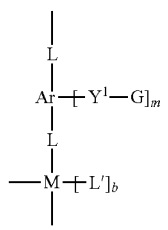

formula (16)

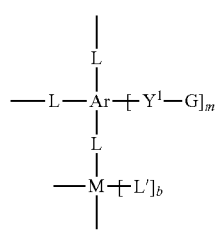

formula (17)

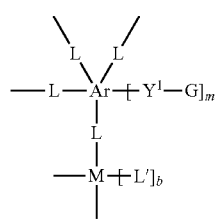

formula (18)

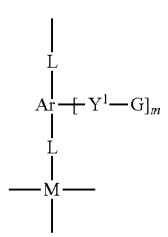

formula (19)

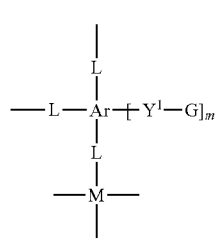

formula (20)

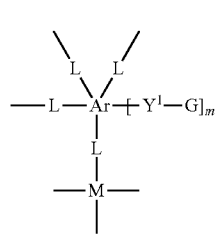

formula (21)

where the symbols Ar, L', $Y^1$ and G and the index m have the same meanings as in the above embodiments, and the other symbols and indices have the following meanings:

M is a mono-, di-, tri- or tetravalent metal;
L is a bidentate ligand of the following formula (g):

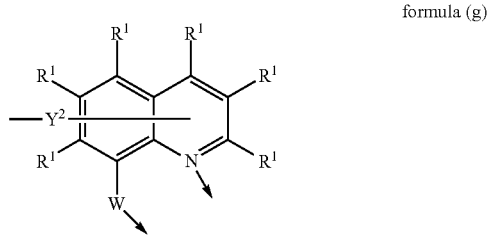

formula (g)

where the bond dash leading away from $Y^2$ represents a bond to Ar in the structural units of the formulae (13) to (21), and the arrows leading away from W and N represent a coordination bond to M, and the symbols $Y^2$, W and $R^1$ have the same meanings as defined in the above claims, where one $R^1$ is not present and the quinoline unit is bonded to $Y^2$ at this position;

a is 0, 1 or 2;
b is 0 or 1;

with the proviso that the bond dashes leading away from L in the structural units of the formulae (13) to (21) represent a bond to M of a further structural unit, and the bond dashes leading away from M in the structural units of the formulae (13) to (21) represent a bond to L of a still further structural unit.

"Polymer" is taken to mean a polymeric compound, which preferably have 10 to 10000, particularly preferably 20 to 5000 and in particular 50 to 2000 structural units (recurring units), i.e. has been built up from a correspondingly large number of monomers. An "oligomer" is taken to mean, in accordance with the invention, compounds which preferably have 2 to 9 recurring units. The branching factor of the polymers here is between 0 (linear polymer with no branching points) and 1 (fully branched dendrimer). I.e. the terms "polymer" and "oligomer" accordingly also encompass dendrimers.

The term "dendrimer" in the present application is intended to be taken to mean a highly branched compound which is built up from a multifunctional centre (core), to which branched monomers are bonded in a regular structure, giving a tree-like structure. Both the core and the monomers here can adopt any desired branched structures. "Dendrimer" here is generally intended to be understood as described, for example, by M. Fischer and F. Vögtle (Angew. Chem., Int. Ed. 1999, 38, 885).

M in the structural unit of the general formula (13) to (21) is preferably an element, a metal or a metal ion of an element selected from the group consisting of Ca, Mg, Ba, Zn, B, Al, Zr, Cu, Sc and Y, particularly preferably Ca, Mg, Zn, Al and Zr. $Al^{3+}$ is extraordinarily preferred.

The following preferably applies to the compound, oligomer or polymer of the formulae (13) to (15):

If M is a metal having four coordination sites, then a is equal to 0;
if M is a metal having five coordination sites and L' is monodentate, then a is equal to 1;
if M is a metal having six coordination sites and L' is monodentate, then a is equal to 2;
if M is a metal having seven coordination sites and L' is monodentate, then a is equal to 3;
if M is a metal having eight coordination sites and L' is monodentate, then a is equal to 4;
if M is a metal having six coordination sites and L' is bidentate, then a is equal to 1;
if M is a metal having seven coordination sites and L' is bidentate, then a is equal to 2.

The following preferably applies to the compounds of the formulae (16) to (18):

If M is a metal having six coordination sites, then a is equal to 0;
if M is a metal having seven coordination sites and L' is monodentate, then a is equal to 1
if M is a metal having eight coordination sites and L' is monodentate, then a is equal to 2;
if M is a metal having eight coordination sites and L' is bidentate, then a is equal to 1.

In a further embodiment of the present invention, it is preferred for M in the structural unit of the general formula (13) to (21) to be a metal having four, six or eight coordination sites.

The index m in the structural unit of the general formula (13) to (21) is preferably equal to 1 or 2.

In still a further embodiment of the present invention, the further structural unit and the still further structural unit in the compound, oligomer or polymer in accordance with the above-mentioned embodiments is in each case, independently of one another, a structural unit which include a metal and/or a mono- or bidentate ligand. The further and still further structural unit may be identical or different from one another. The further structural unit and the still further structural unit is particularly preferably in each case, independently of one another, a structural unit of the formula (13) to (21). The further and still further structural unit is extraordinarily preferably a structural unit of the same formula as the structural unit according to the invention. In this case, the oligomer or polymer is a homopolymer.

If the structural unit of the general formula (13) to (21) in the compound, oligomer or polymer in accordance with the above-mentioned embodiments is a terminal structural unit in the compound, oligomer or polymer, either a unit of the following formula (h) is bonded to L or a unit of the following formula (i) is bonded to M:

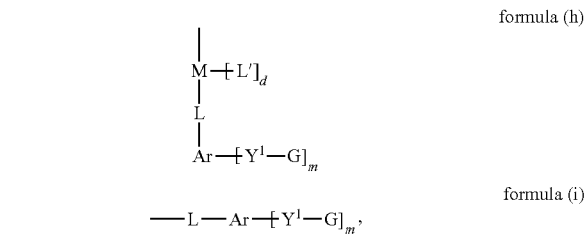

formula (h)

formula (i)

where the symbols M, L, L', Ar, $Y^1$ and G and the index m have the same meanings as in the above embodiments and the index d is equal to 0, 1, 2, 3 or 4.

In a further embodiment, it is preferred for Ar in the compound of the general formulae (1) to (12) or the compound, oligomer or polymer of the general formulae (13) to (21) to be an aromatic or heteroaromatic ring system having 5 to 22 aromatic ring atoms, which may be substituted by one or more radicals $R^9$. An aromatic or heteroaromatic ring system is taken to mean a ring system as defined above, which preferably has 5 to 22 ring atoms. It is furthermore particularly preferred for Ar to be selected from the group consisting of phenyl, naphthalene, anthracene, phenanthrene, benzanthracene, benzophenanthrene, dibenzanthracene, pyrene, 1,3, 5-triazine, pyrazine, quinoxaline and phenanthroline. The groups mentioned above for Ar are particularly preferred.

In still a further embodiment, it is preferred for $Y^1$ and $Y^2$ in the compound of the general formulae (1) to (12) or the compound, oligomer or polymer of the general formulae (13) to (21) in each case, independently of one another, either not to be present or to represent an aromatic or heteroaromatic ring system having 5 to 10 aromatic ring atoms. $Y^1$ and $Y^2$ are particularly preferably each selected, independently of one another, from the group consisting of a single covalent bond, phenyl, naphthalene, anthracene and thiophene. The groups mentioned above for $Y^1$ and $Y^2$ are particularly preferred.

The group W in the embodiments according to the invention is preferably an oxygen atom.

The group L' is preferably a monodentate or bidentate ligand. Examples of monodentate ligands L' include the following structures (1) to (26):

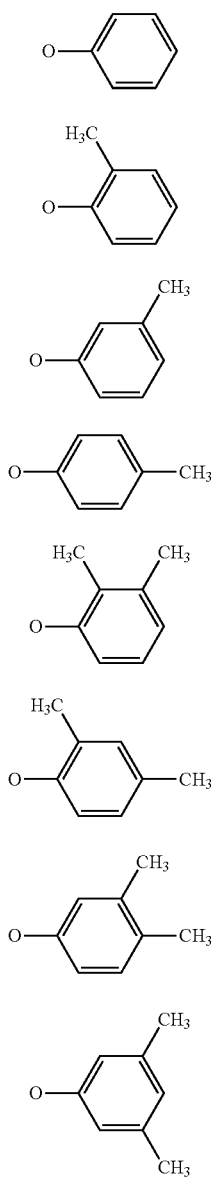

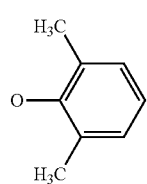

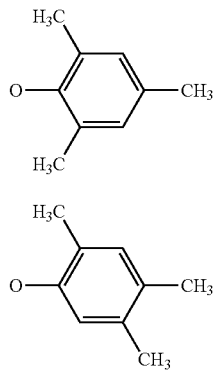

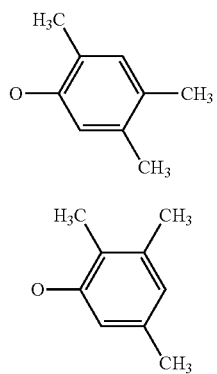

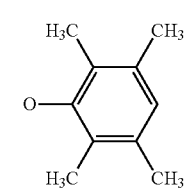

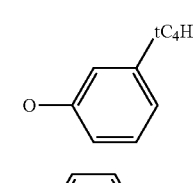

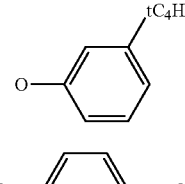

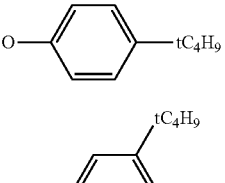

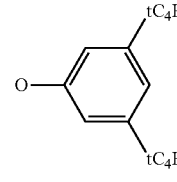

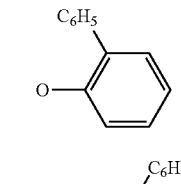

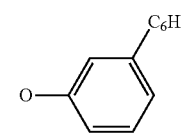

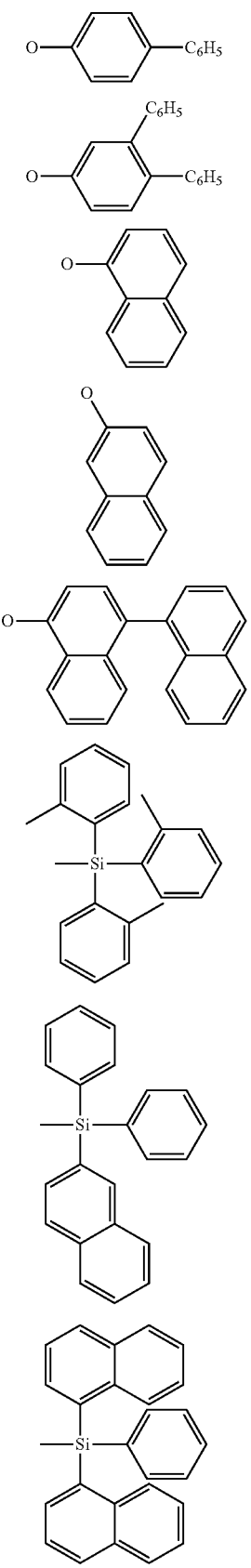

Structures (1) to (23) coordinate here via the oxygen and structures (24) to (26) via the silicon.

L' is preferably a bidentate ligand. L' is particularly preferably equal to 8-hydroxyquinoline.

In accordance with the invention, the preferred embodiments mentioned above can be combined with one another as desired.

Examples of suitable compounds according to the invention are compounds (1) to (160) shown below:

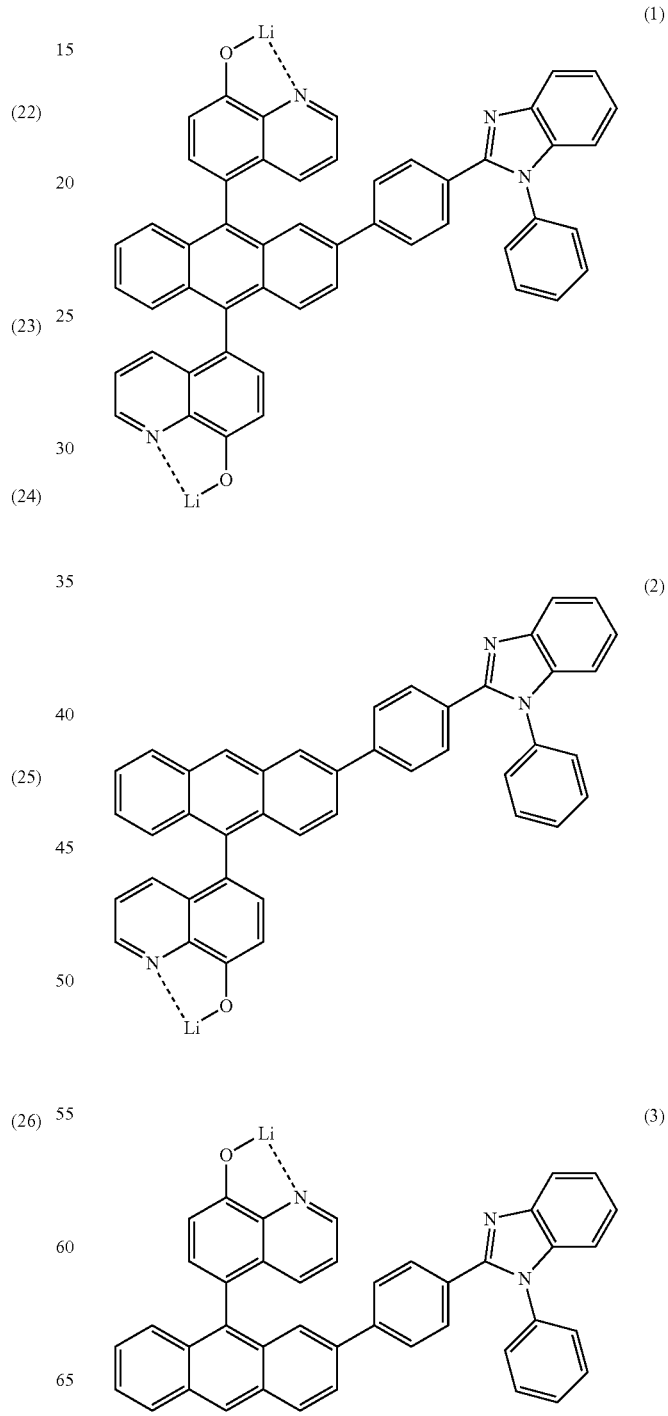

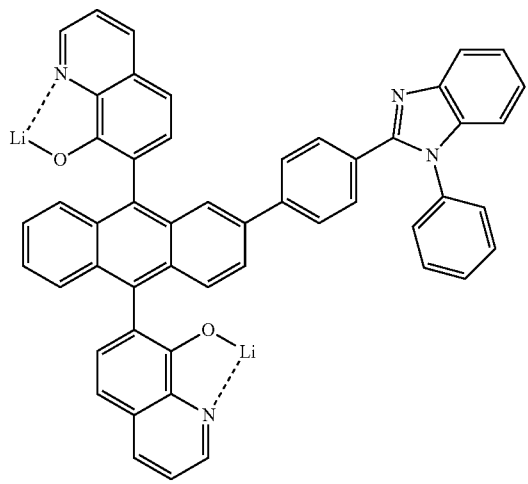
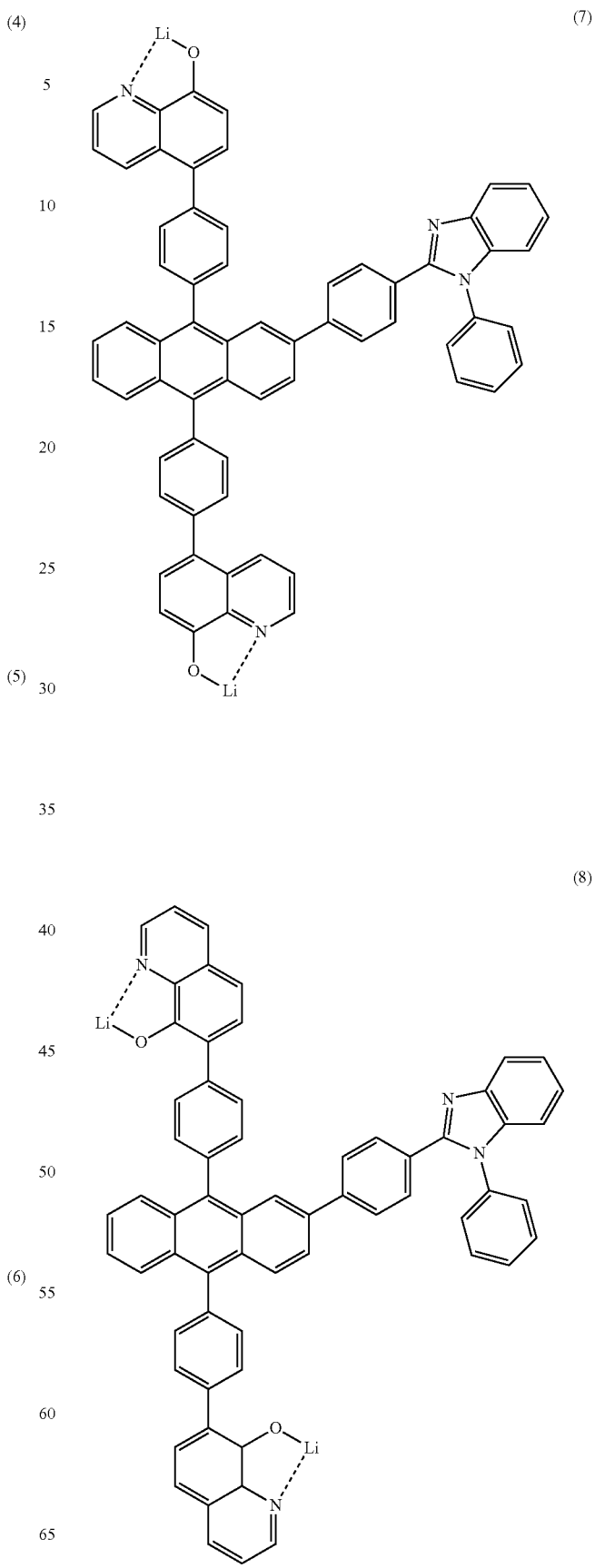

-continued
(9)
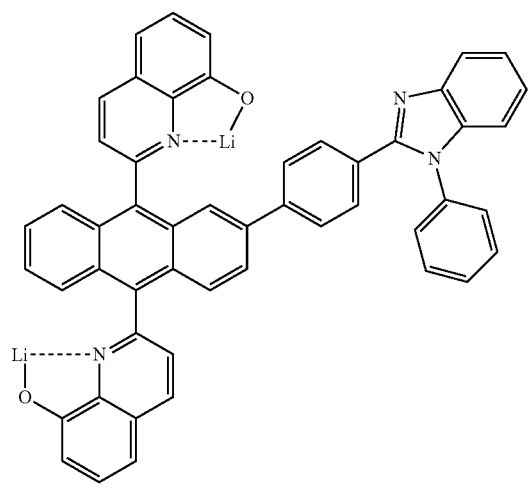
(10)
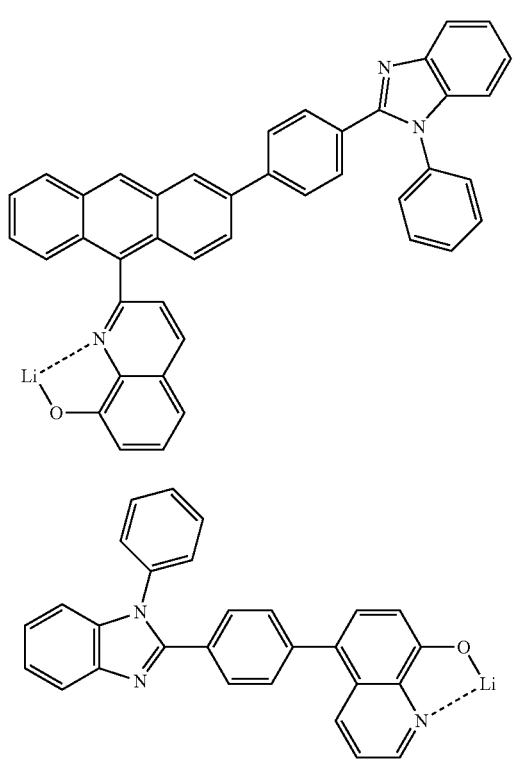
(11)
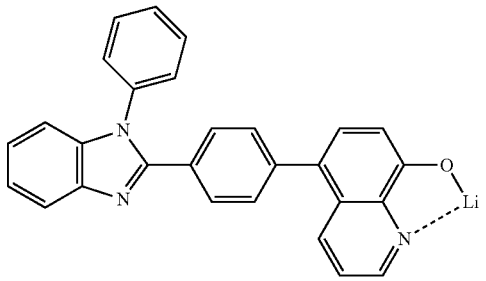
(12)
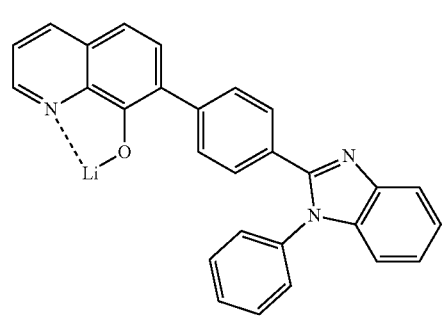
-continued
(13)
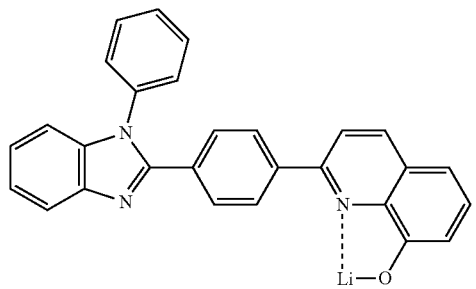
(14)
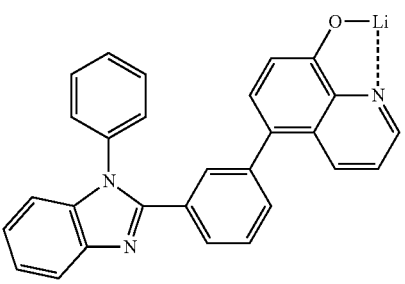
(15)
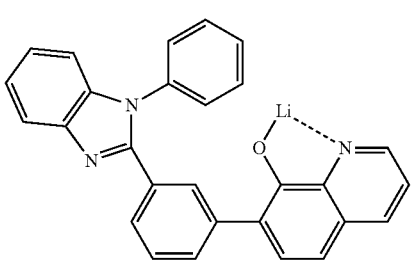
(16)
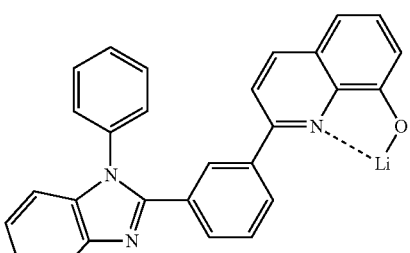
(17)
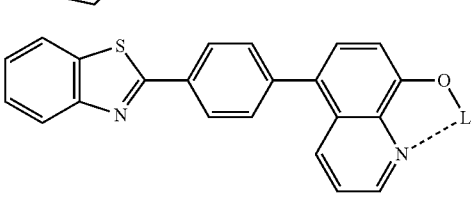
(18)
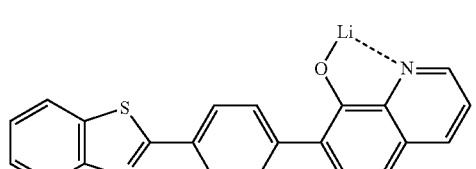
(19)
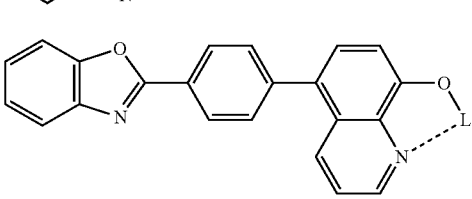

(20)
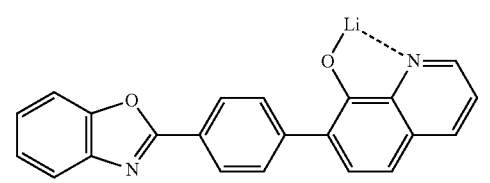
(21)
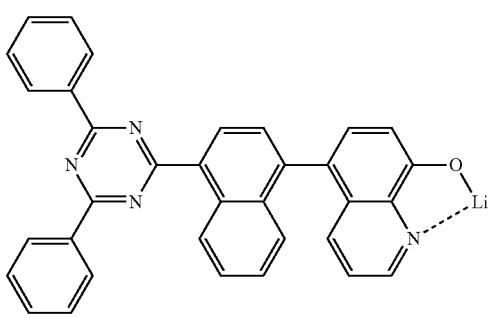
(22)
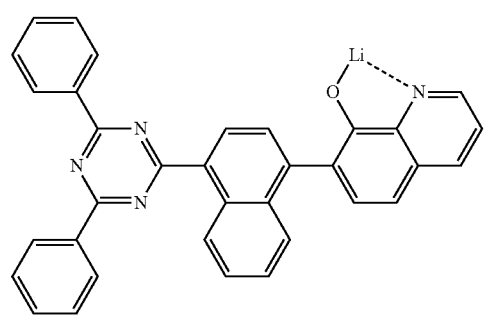
(23)
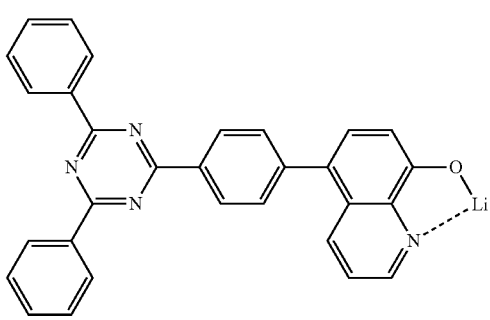
(24)
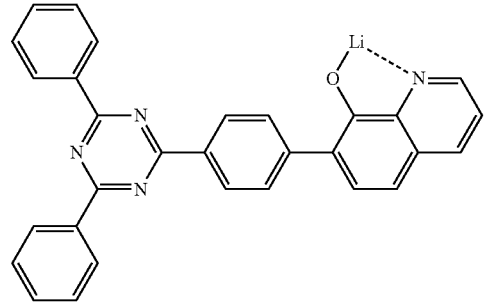
(25)
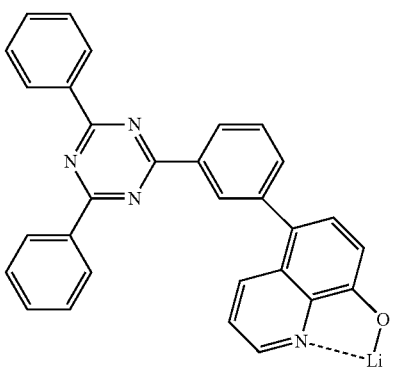
(26)
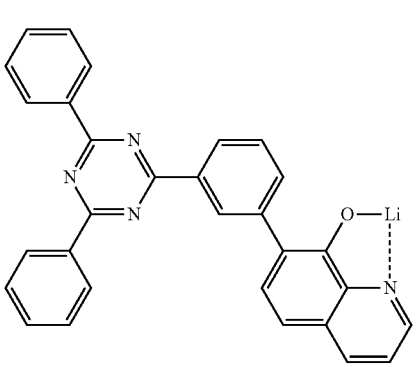
(27)
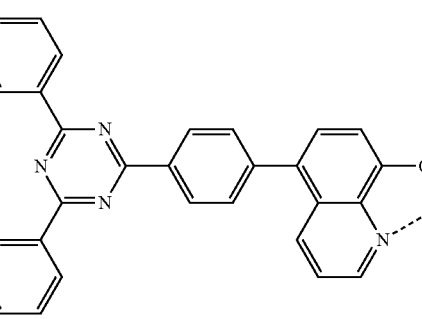
(28)
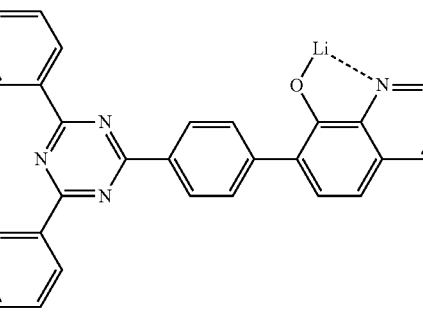

-continued
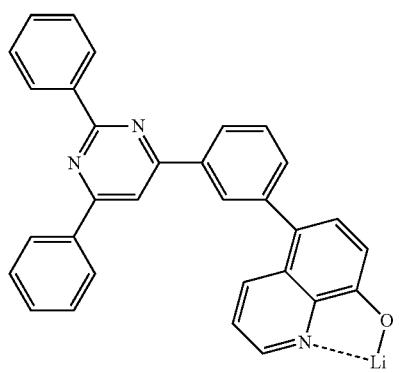
(29)
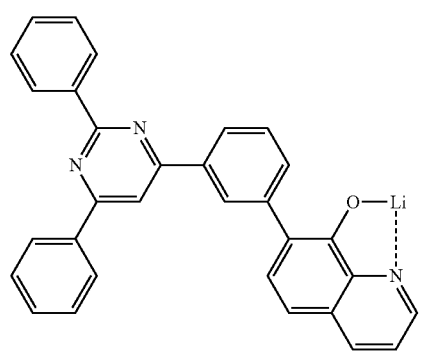
(30)
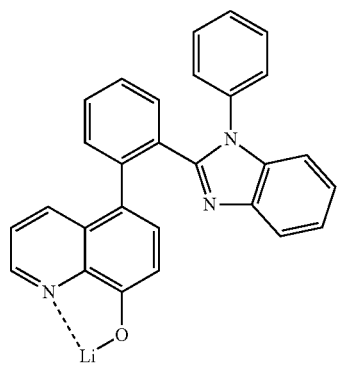
(31)
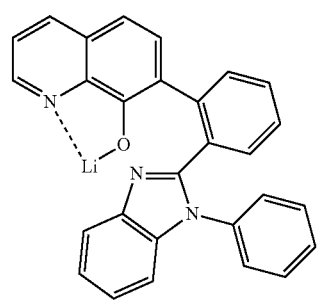
(32)
-continued
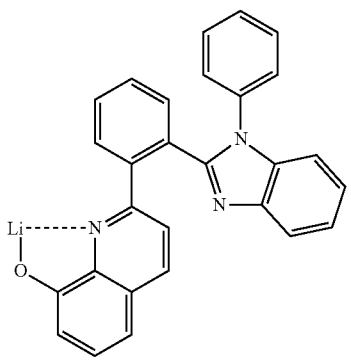
(33)
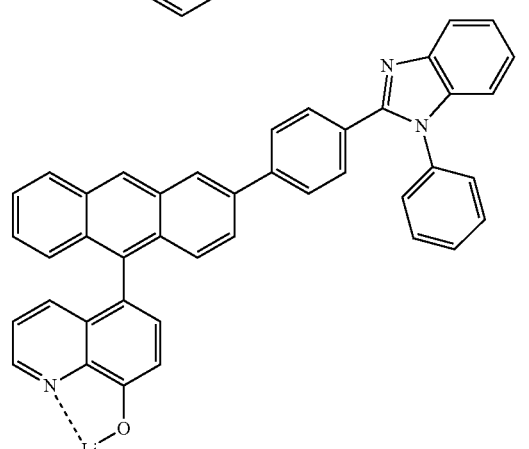
(34)
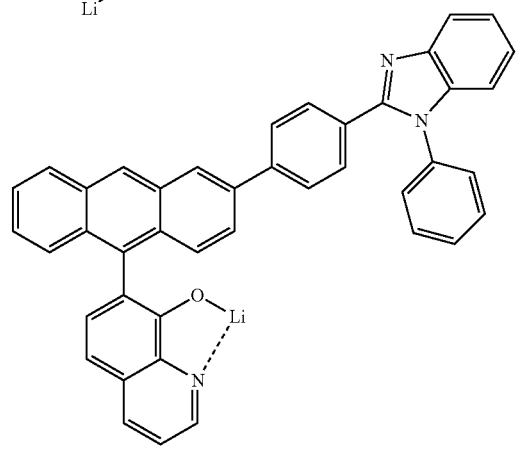
(35)
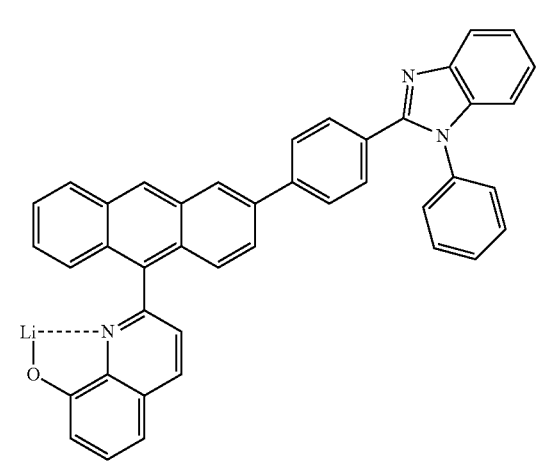
(36)

-continued
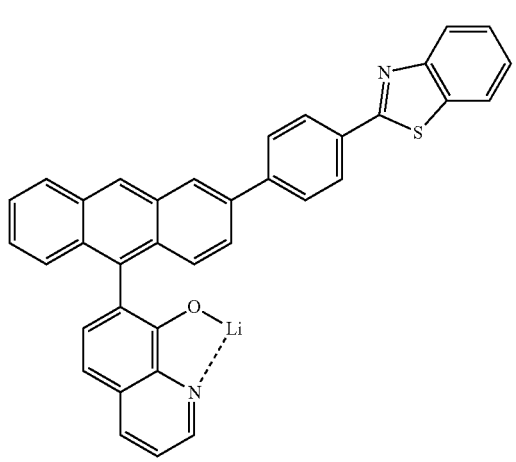
(37)
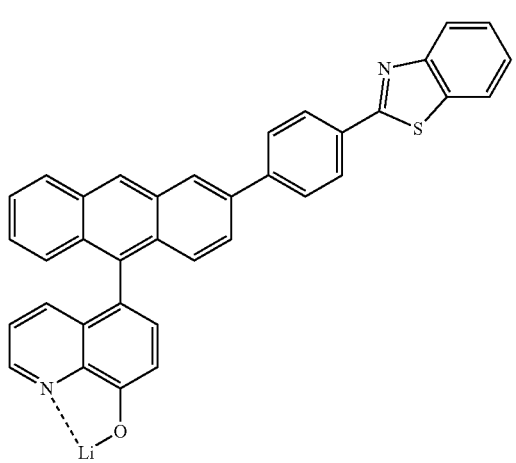
(38)
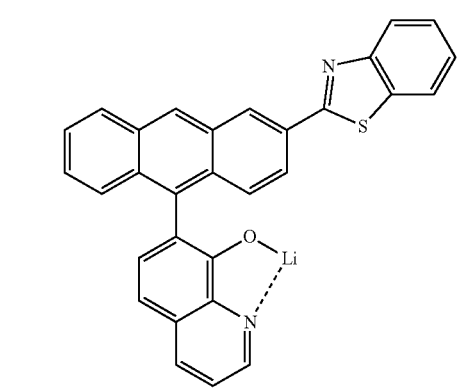
(39)
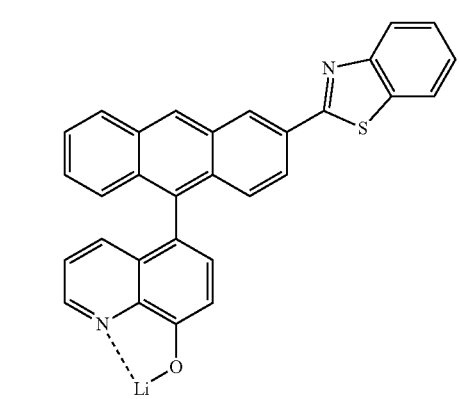
(40)
-continued
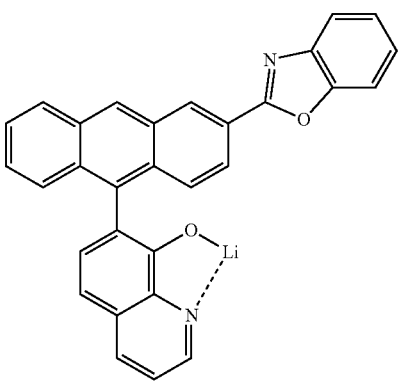
(41)
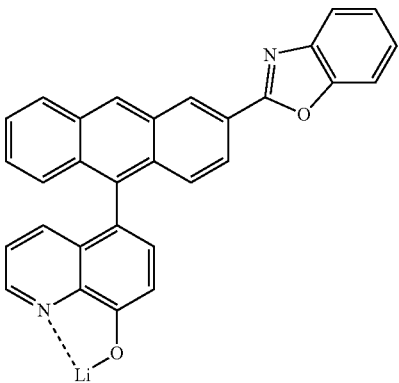
(42)
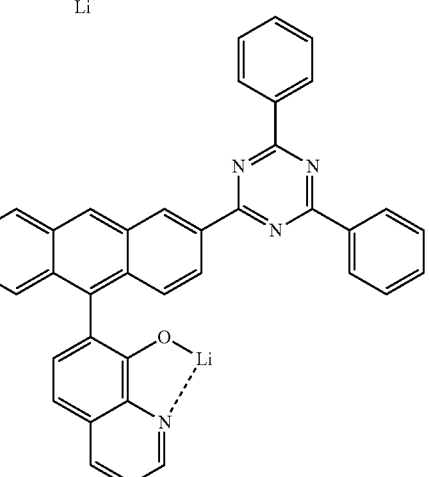
(43)
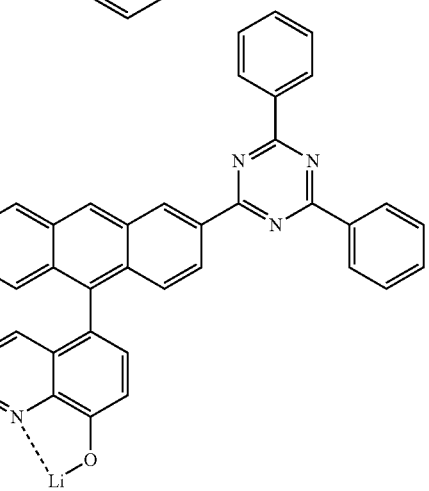
(44)

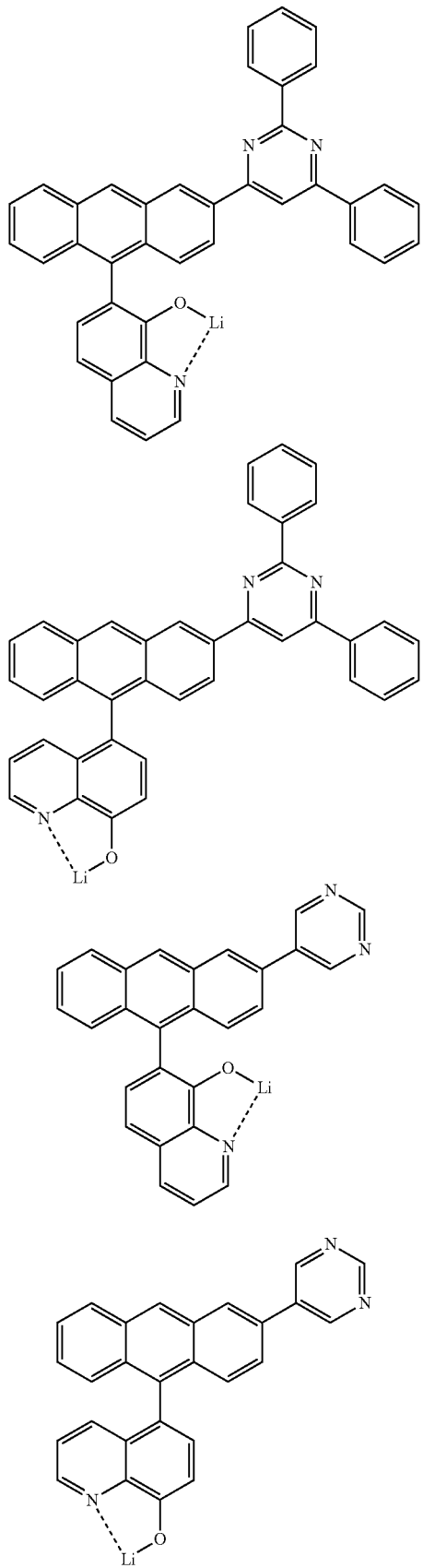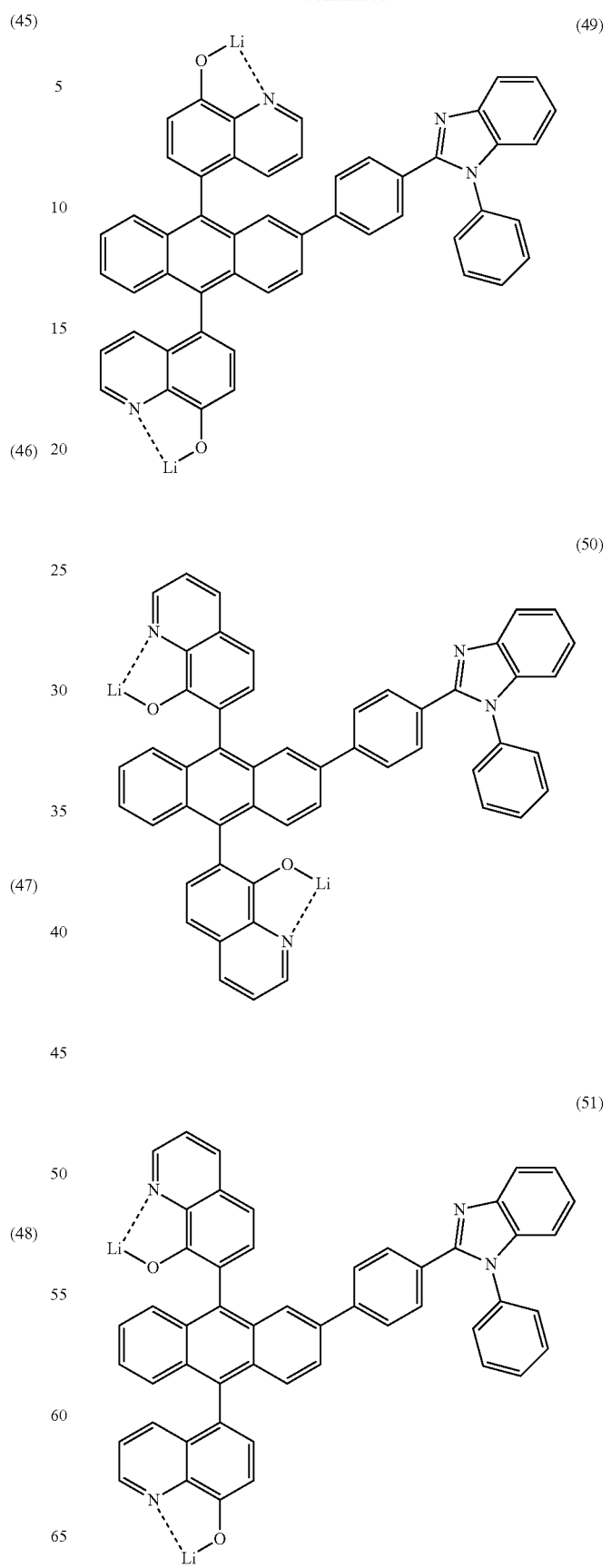

(52)
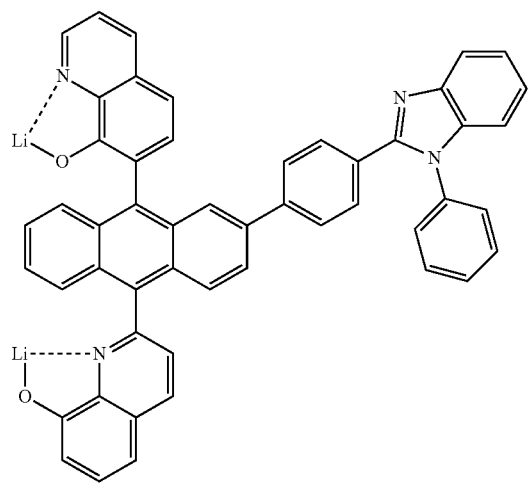
(53)
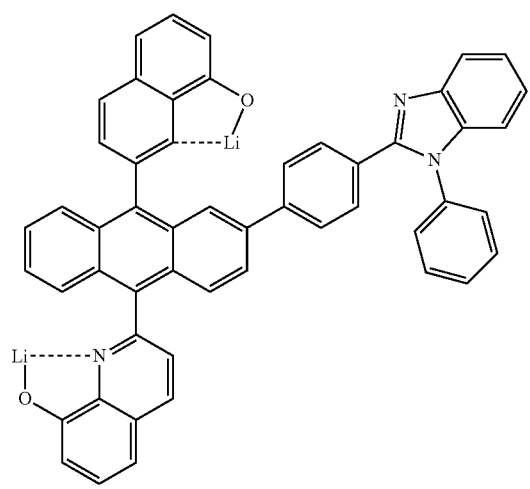
(54)
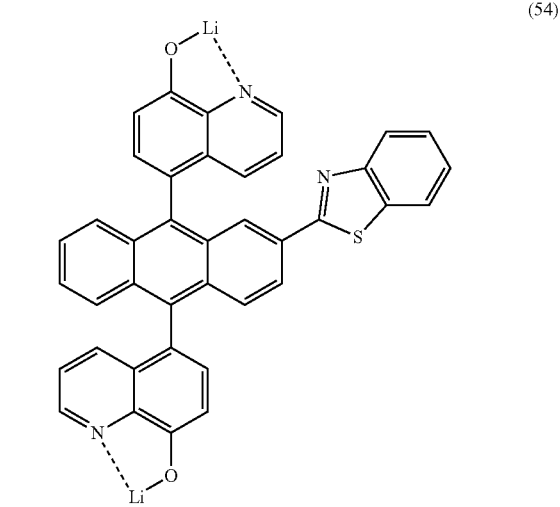
(55)
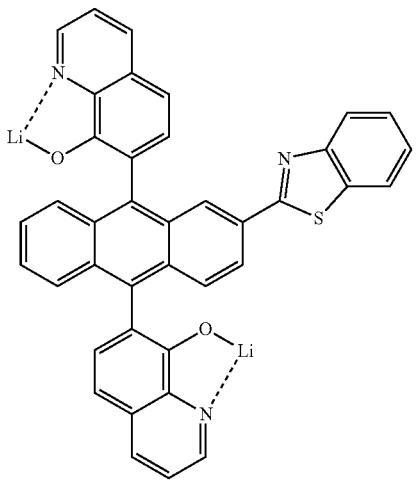
(56)
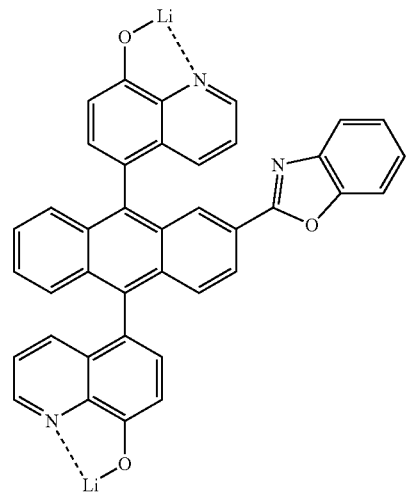
(57)
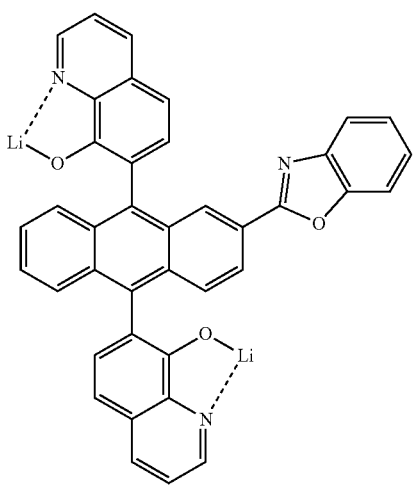

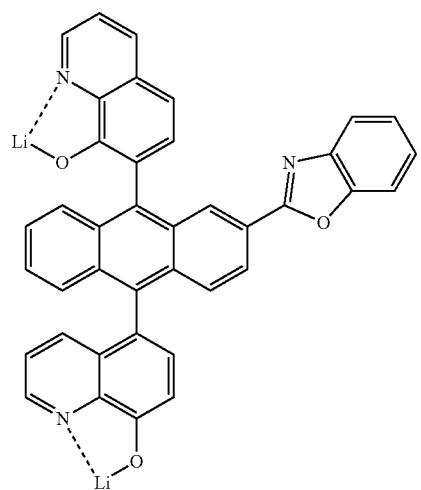
(58)
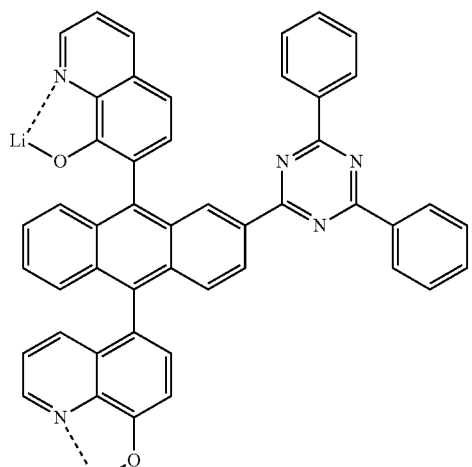
(61)
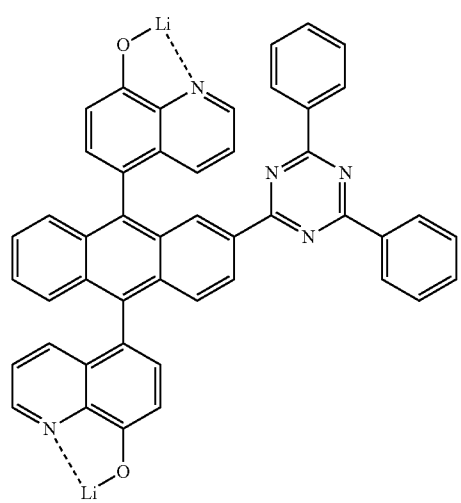
(59)
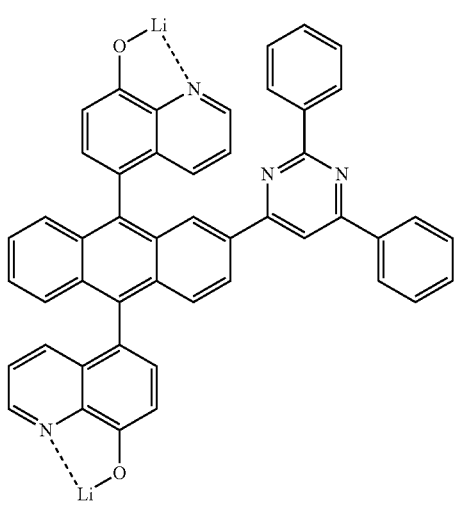
(62)
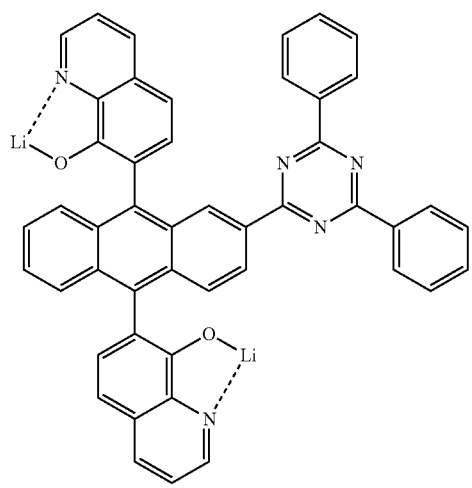
(60)
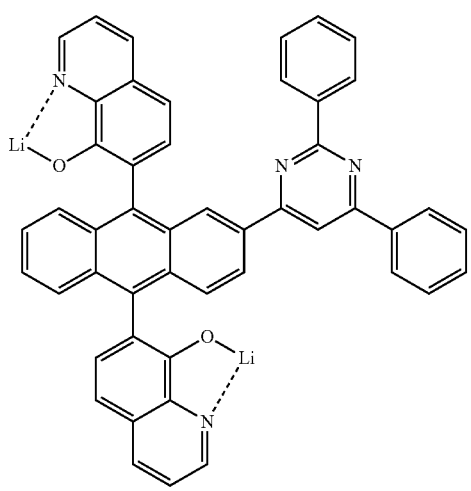
(63)

(64)
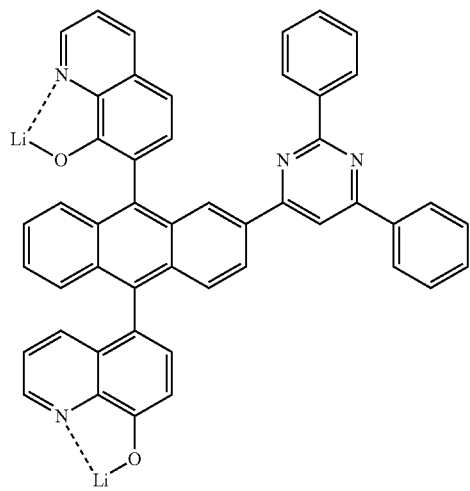
(65)
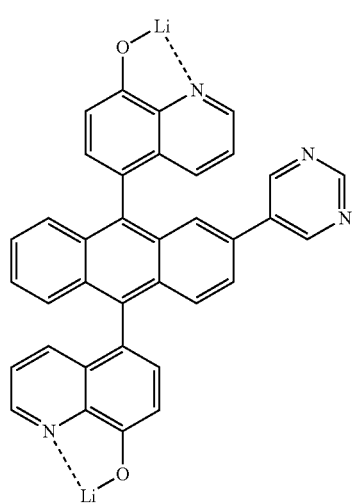
(66)
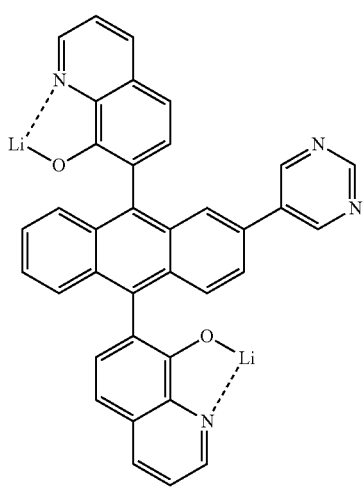
(67)
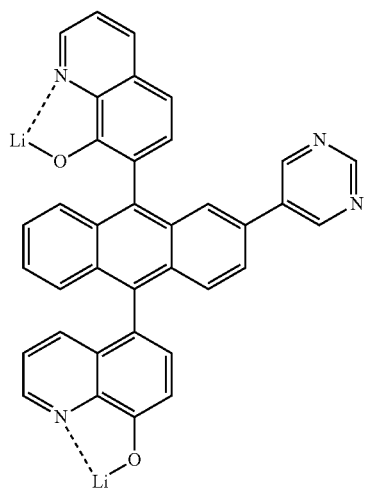
(68)
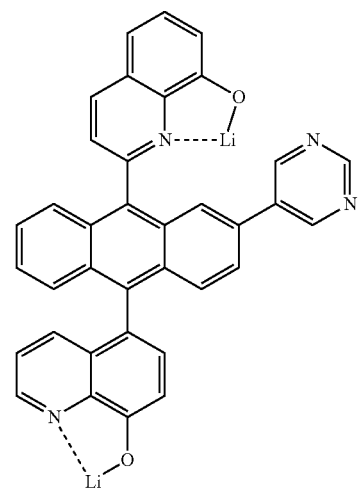
(69)
(70)
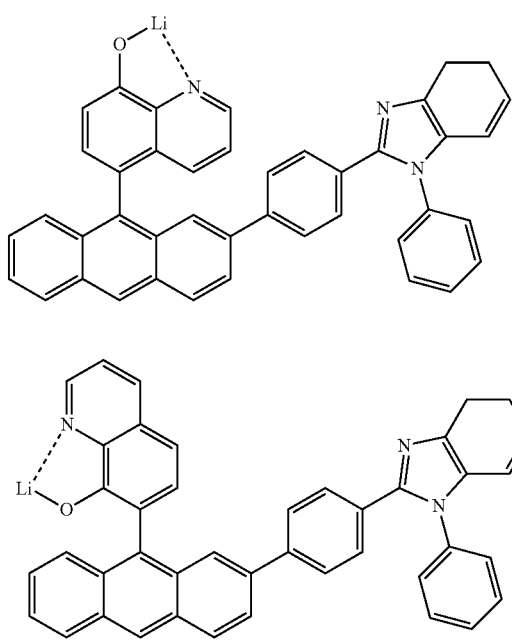

(71)
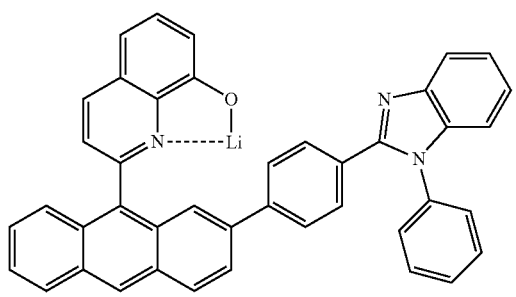
(72)
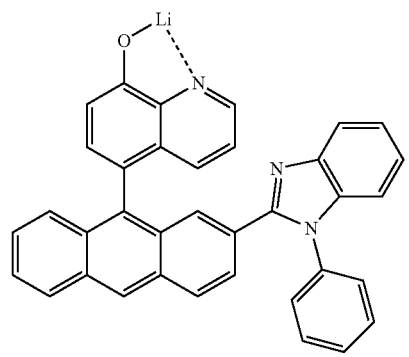
(73)
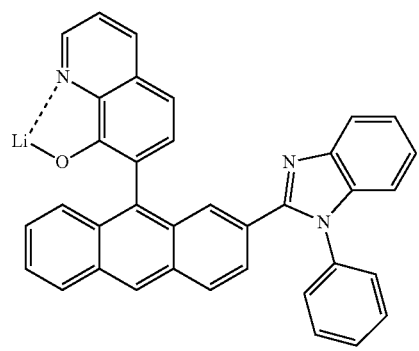
(74)
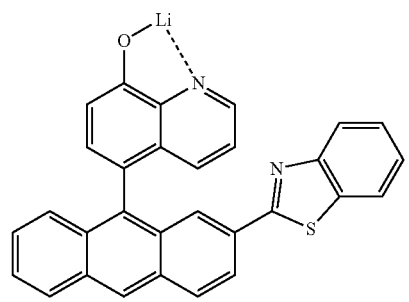
(75)
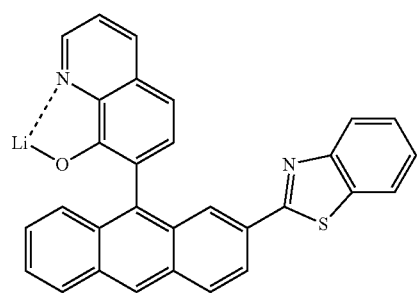
(76)
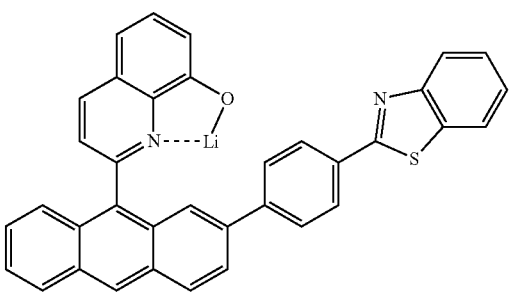
(77)
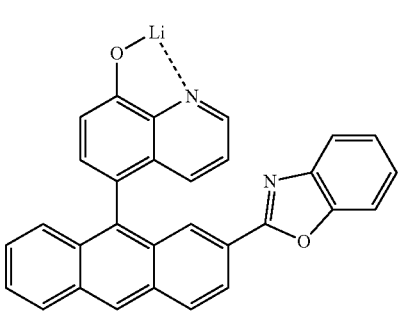
(78)
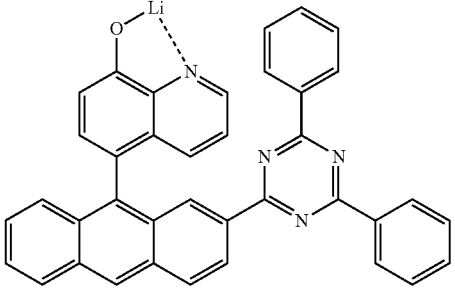
(79)
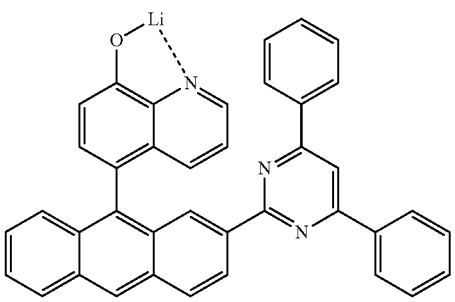
(80)
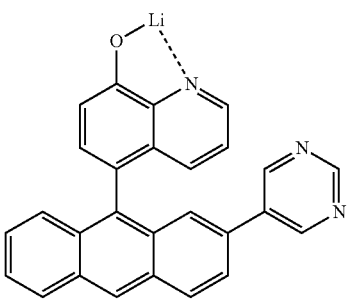

(81)
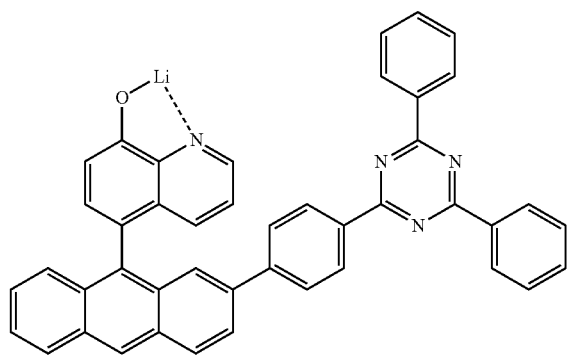
(82)
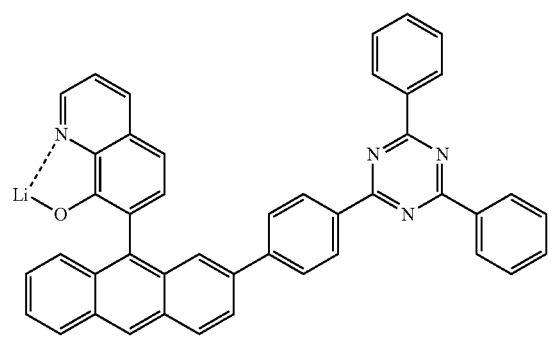
(83)
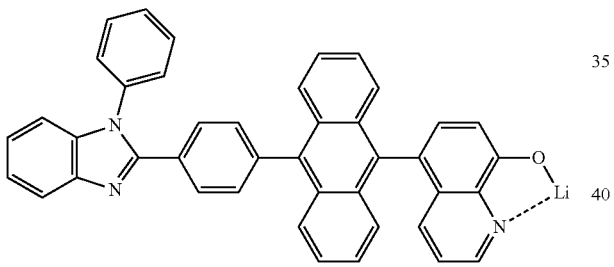
(84)
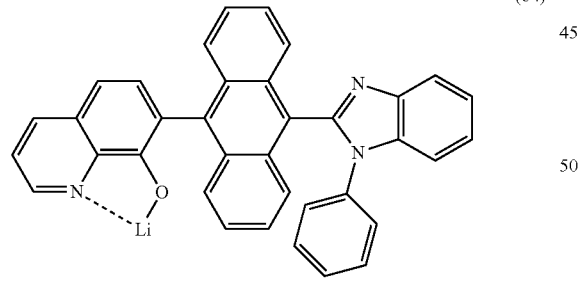
(85)
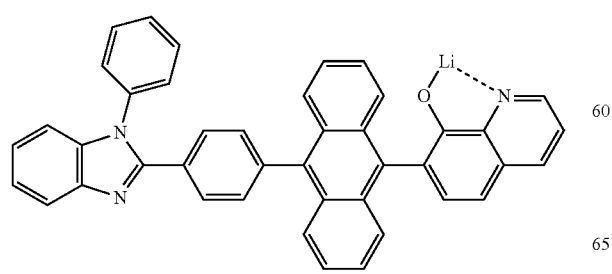
(86)
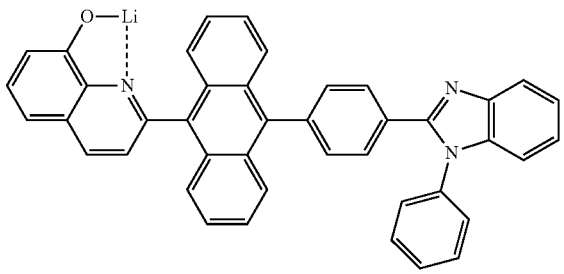
(87)
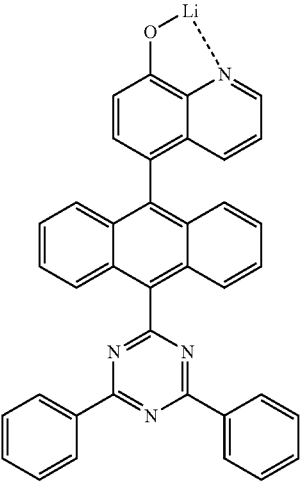
(88)
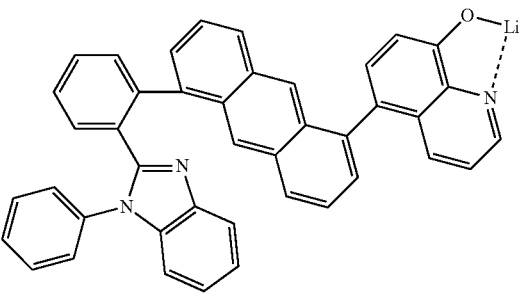
(89)
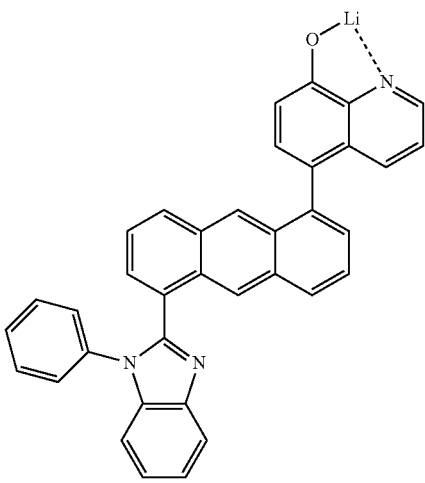

(90)
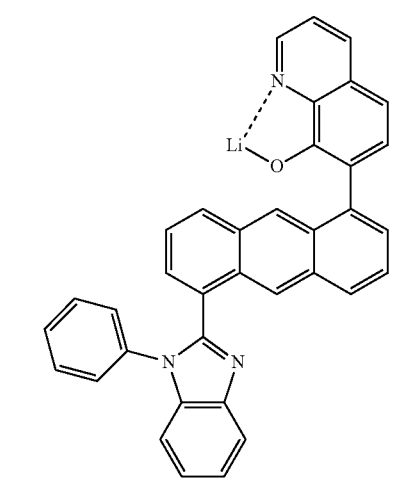
(91)
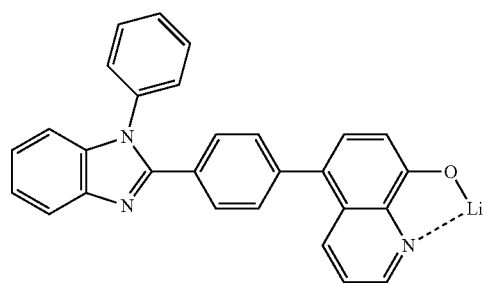
(92)
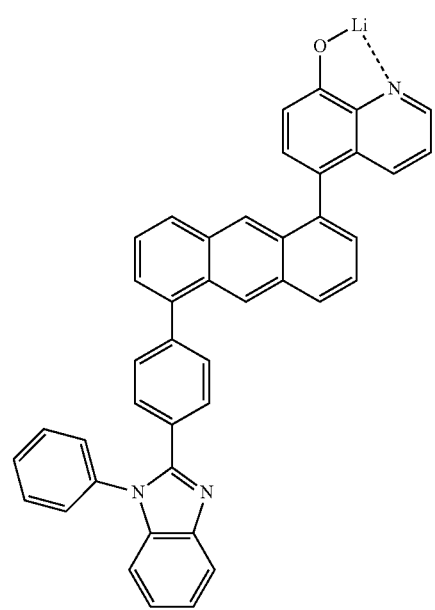
(93)
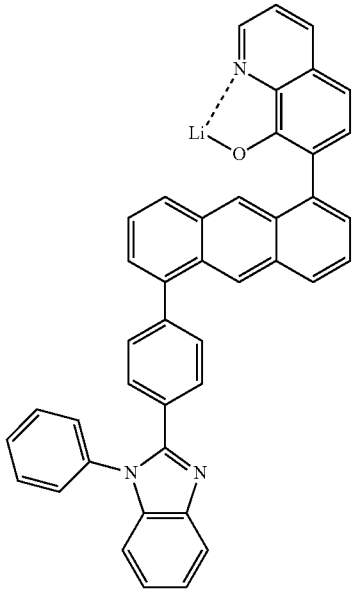
(94)
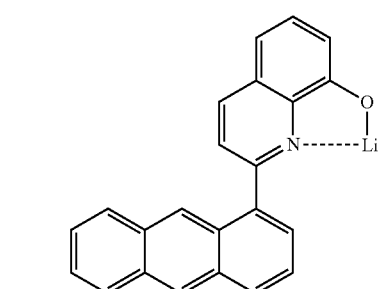
(95)
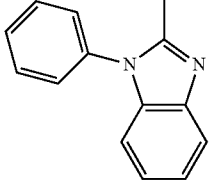
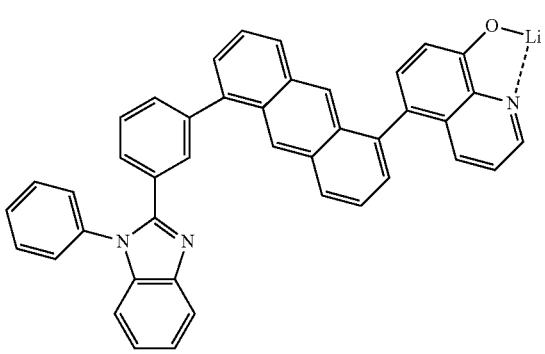

(96)
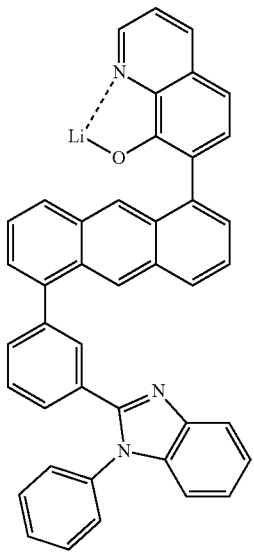
(97)
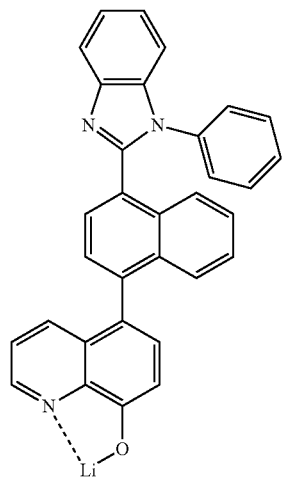
(98)
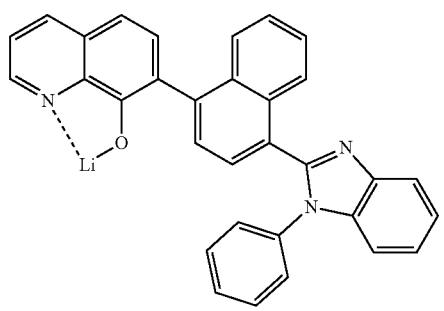
(99)
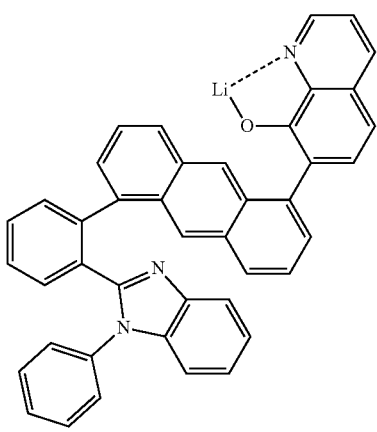
(100)
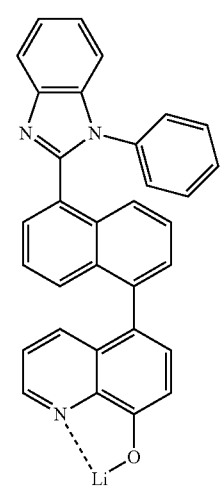
(101)
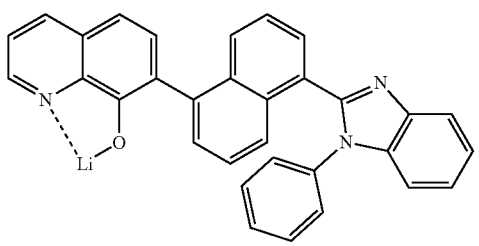
(102)
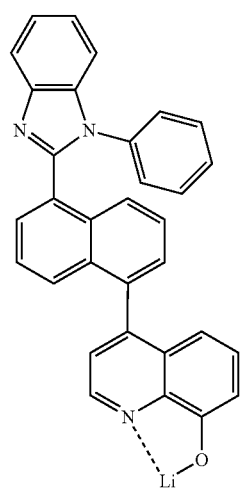

(103)
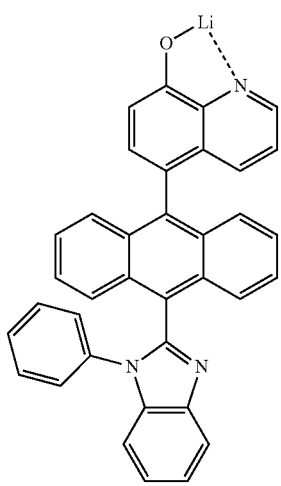
(106)
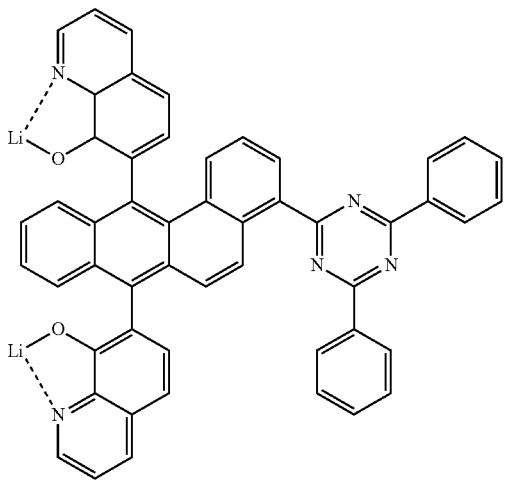
(104)
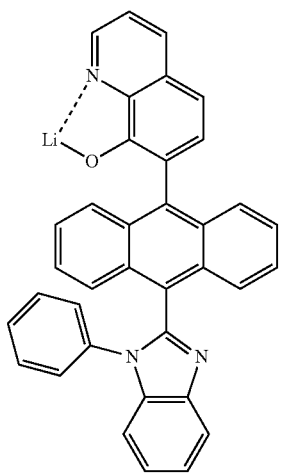
(107)
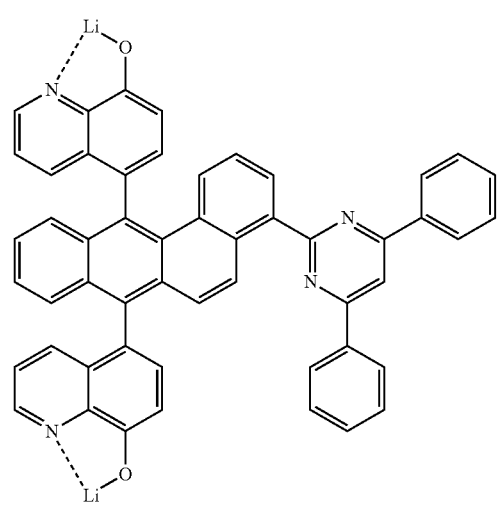
(105)
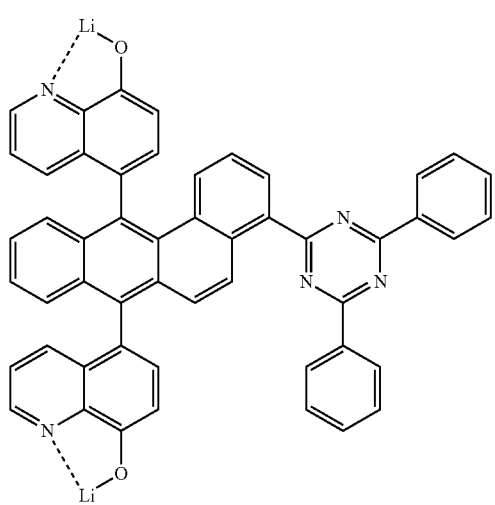
(108)
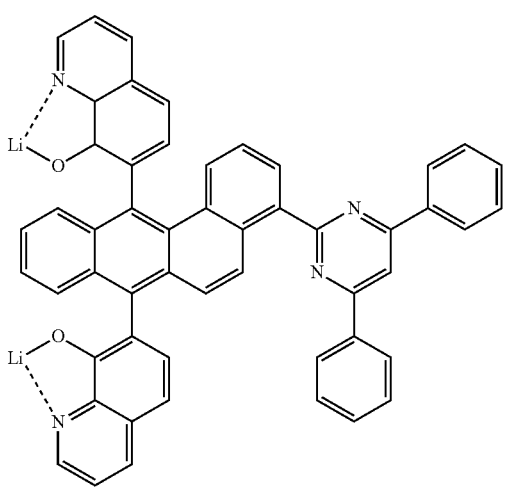

(109)
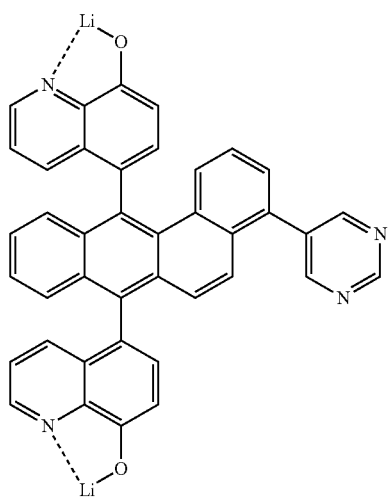
(112)
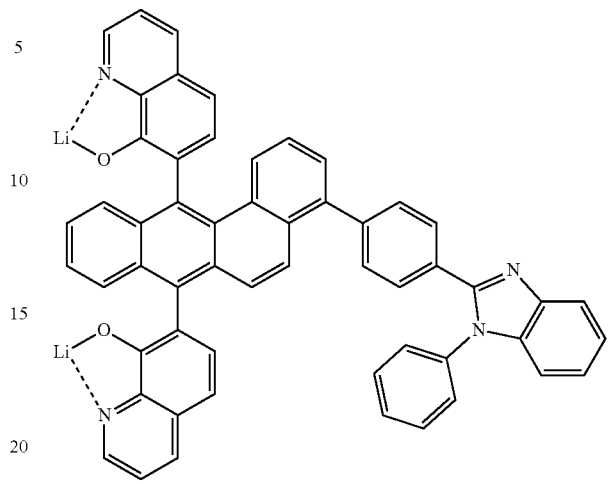
(110)
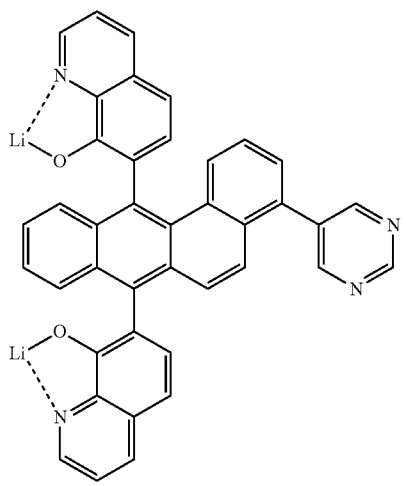
(113)
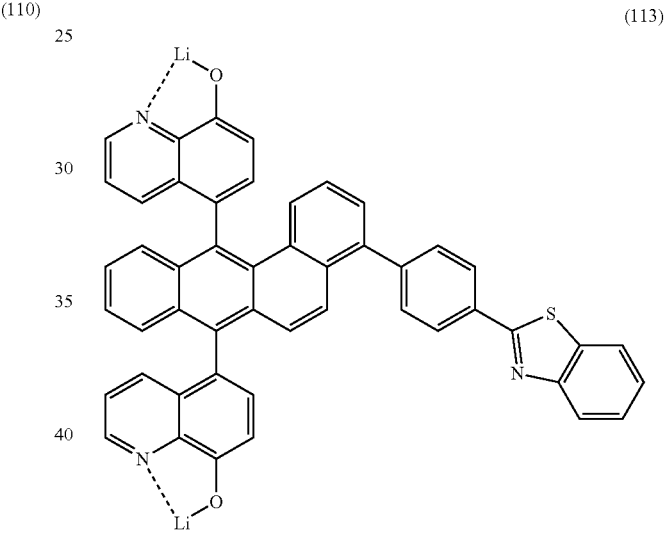
(111)
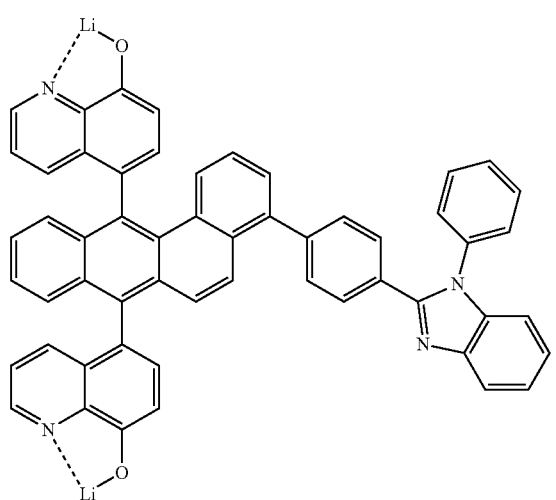
(114)
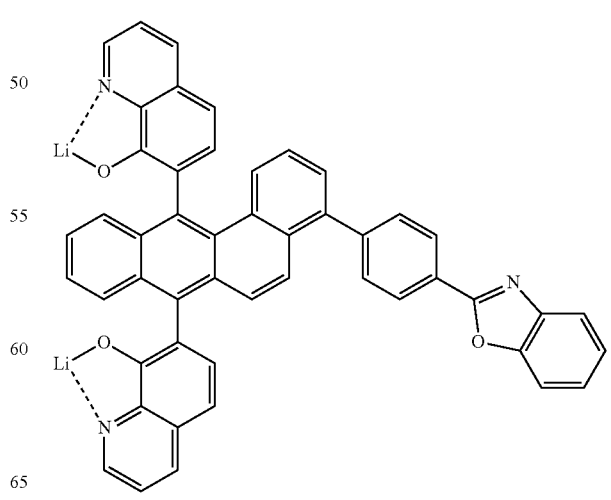

(115)
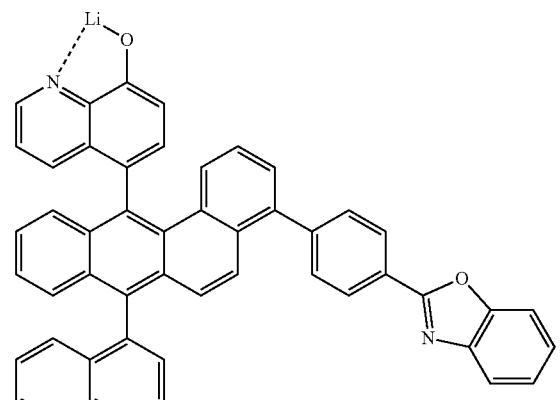
(116)
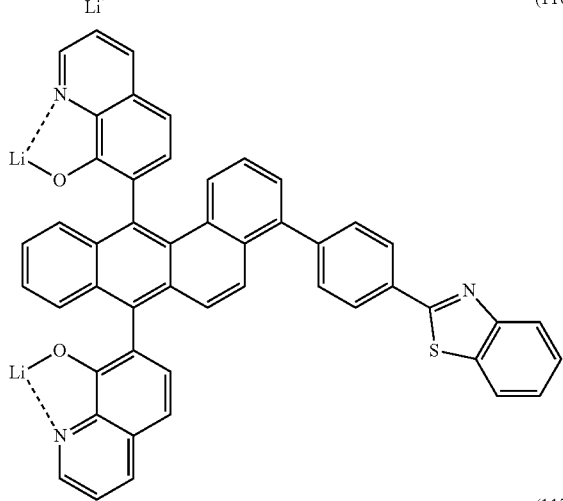
(117)
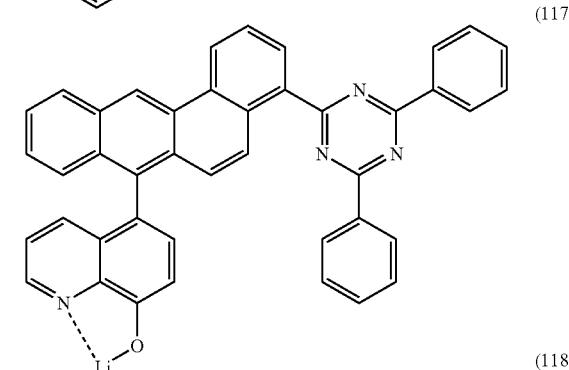
(118)
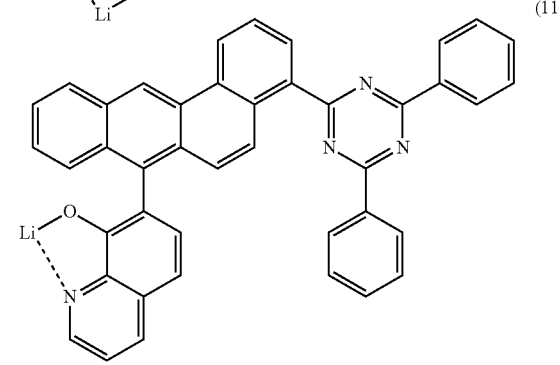
(119)
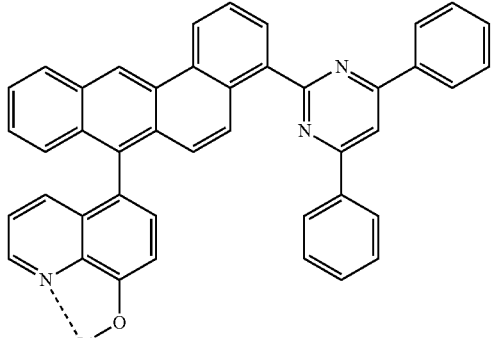
(120)
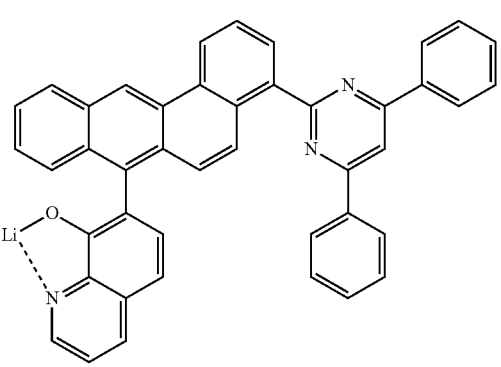
(121)
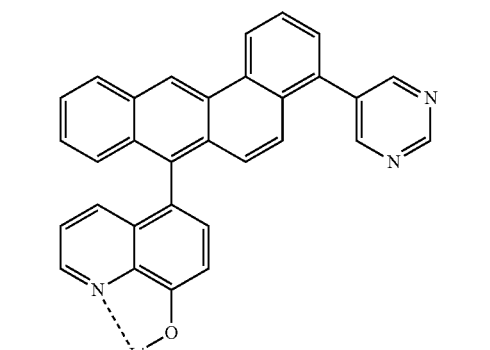
(122)
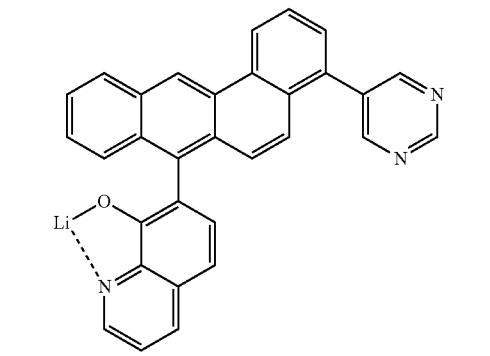

(123)
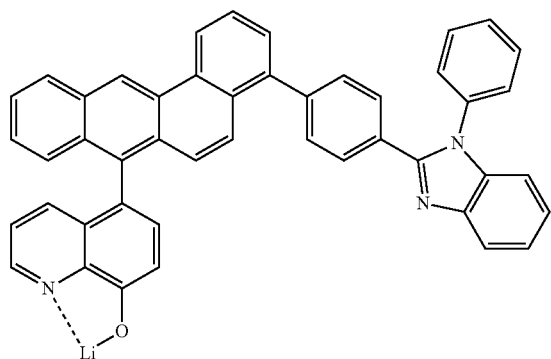
(124)
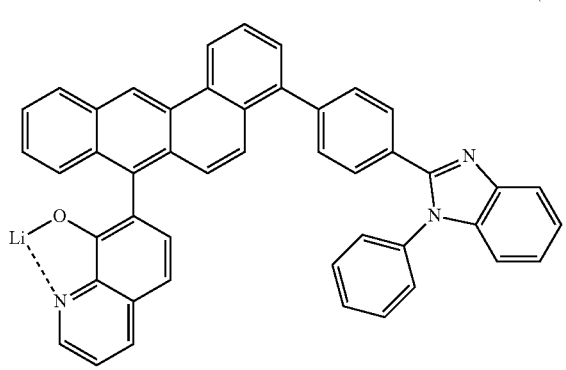
(125)
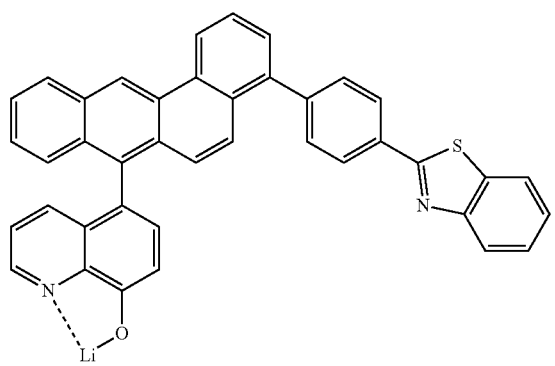
(126)
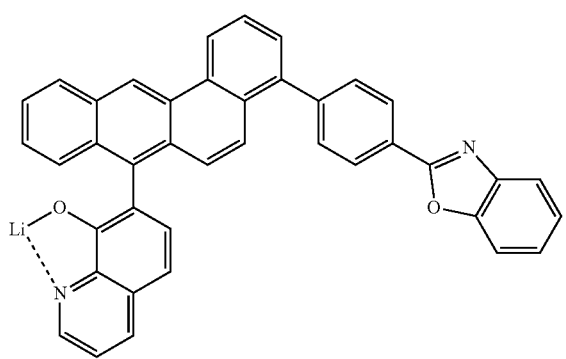
(127)
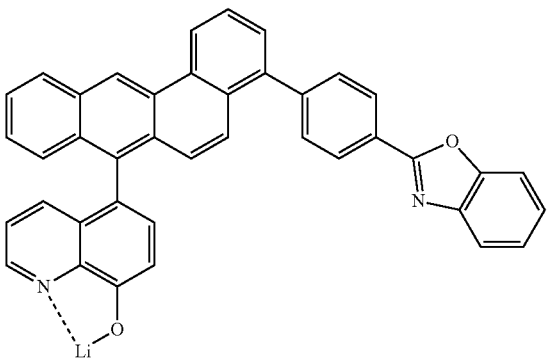
(128)
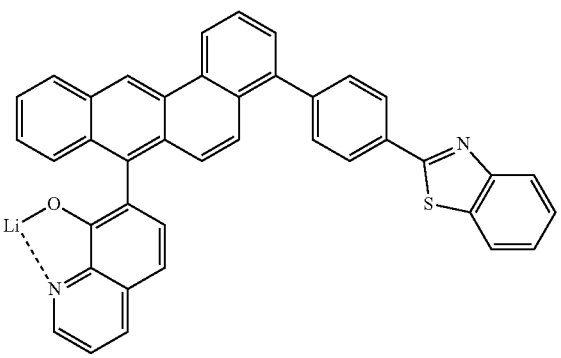
(129)
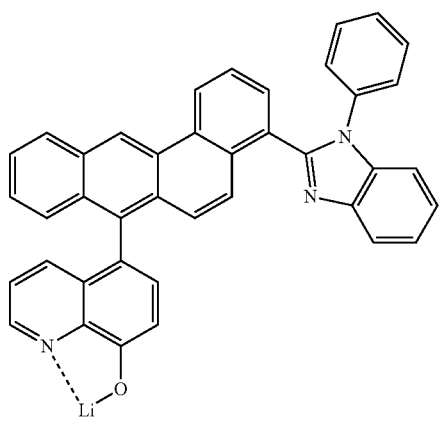
(130)
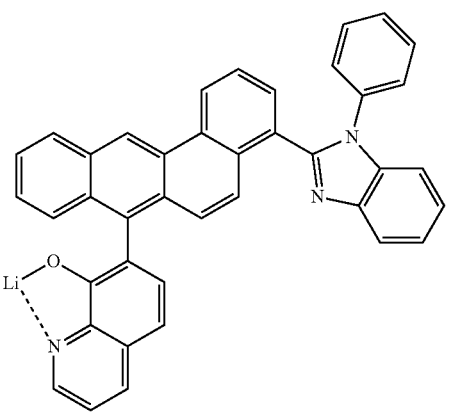

(131) 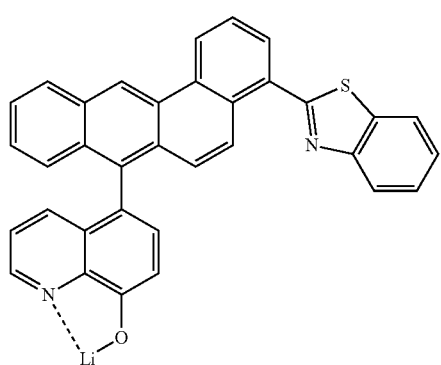
(132) 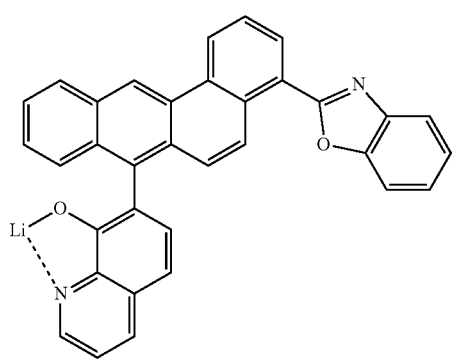
(133) 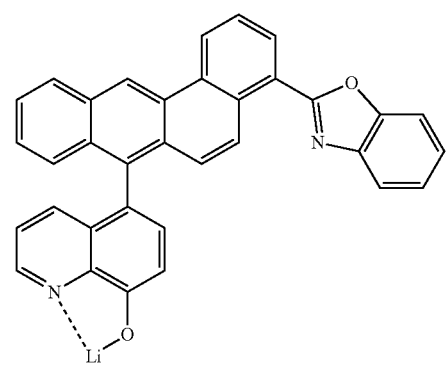
(134) 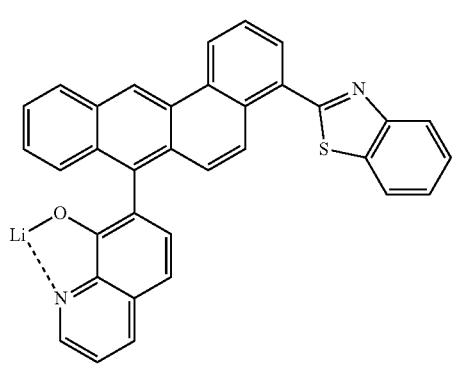
(135) 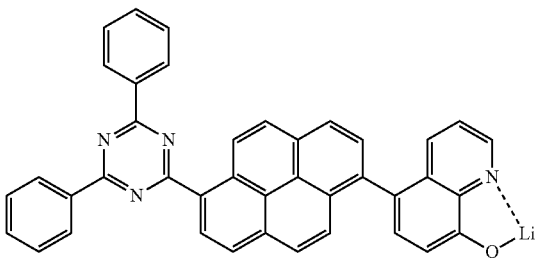
(136) 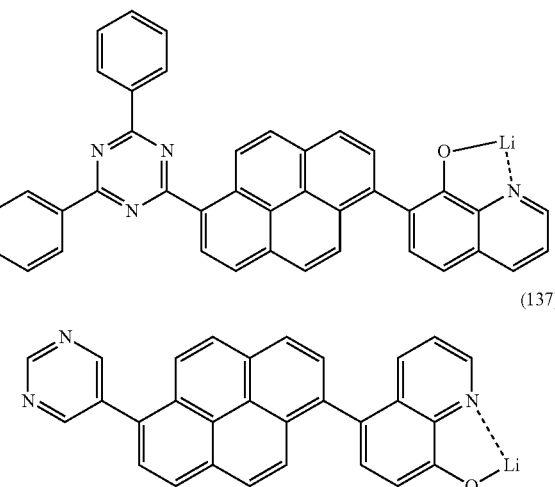
(137) 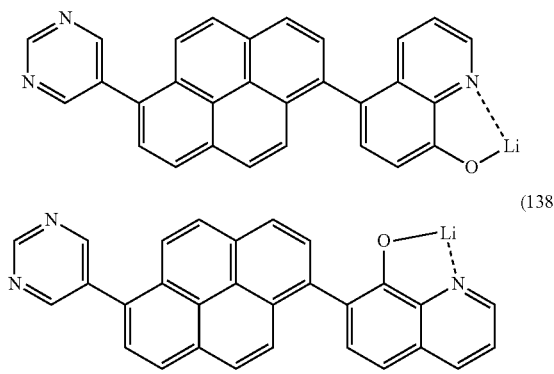
(138) 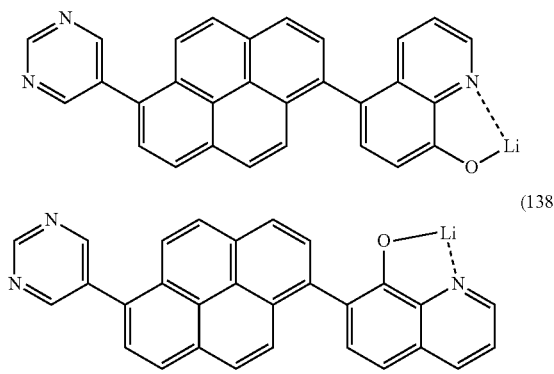
(139) 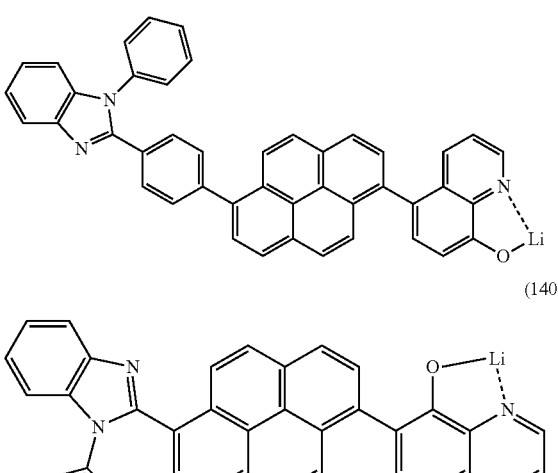
(140) 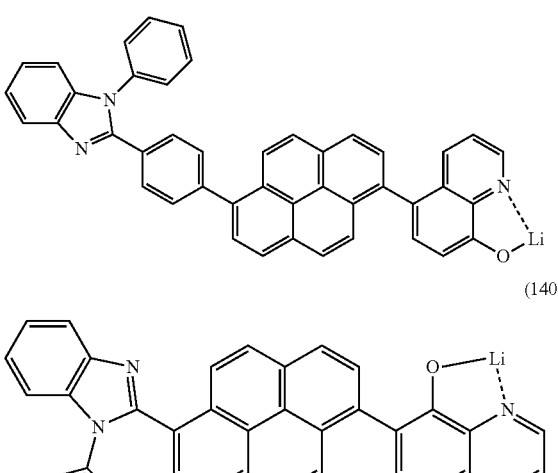

(141)
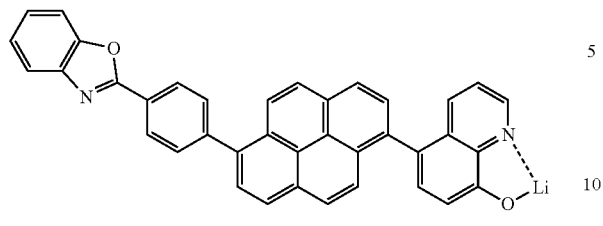
(142)
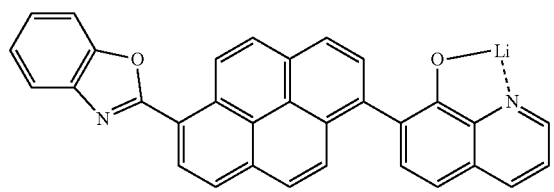
(143)
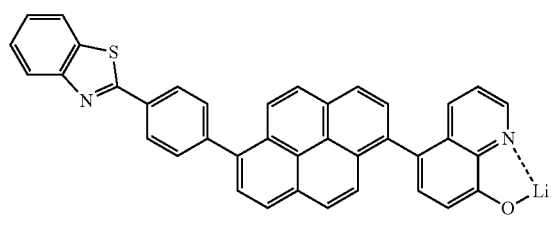
(144)
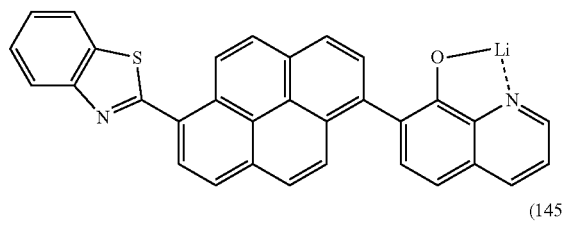
(145)
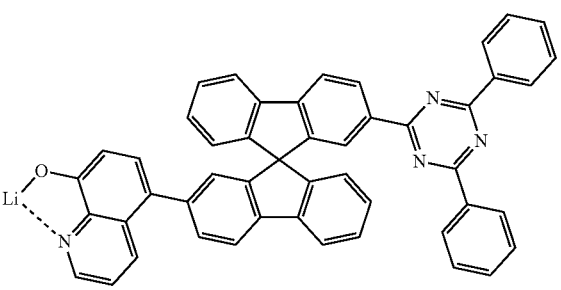
(146)
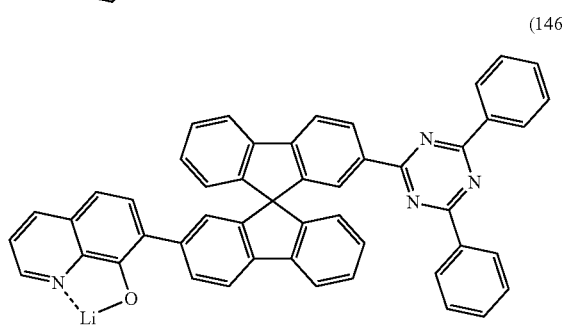
(147)
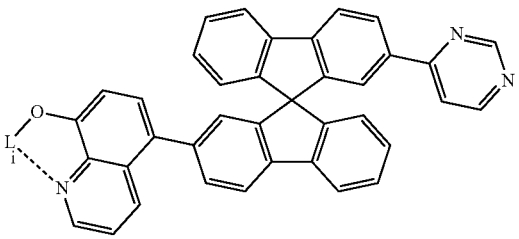
(148)
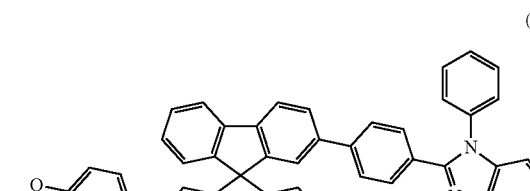
(149)
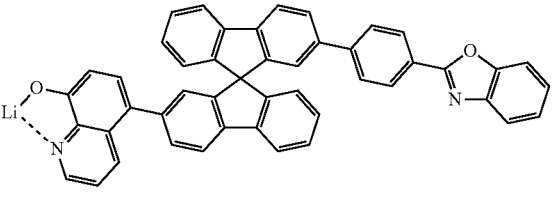
(150)
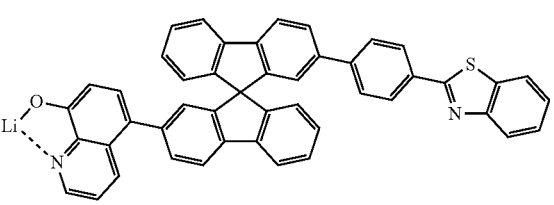
(151)
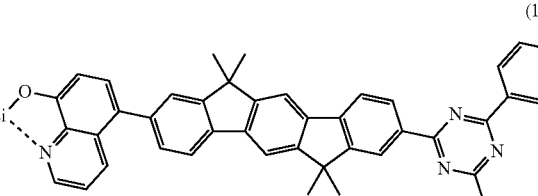
(152)
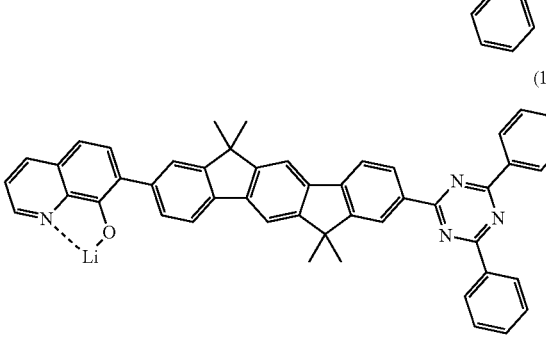

(153)
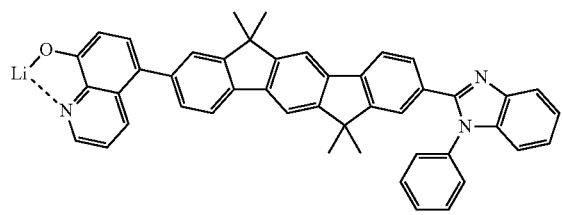

(154)
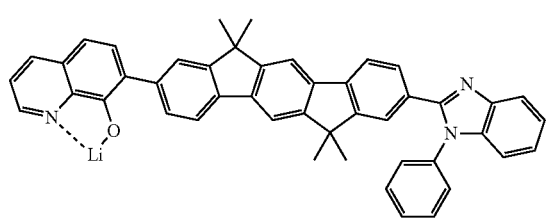

(155)
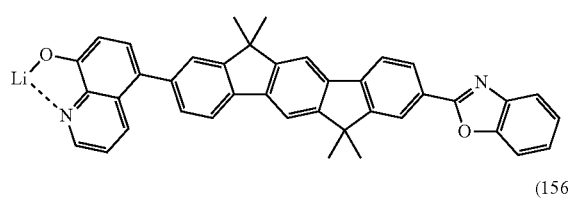

(156)
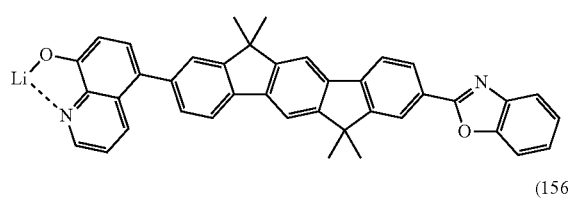

(157)
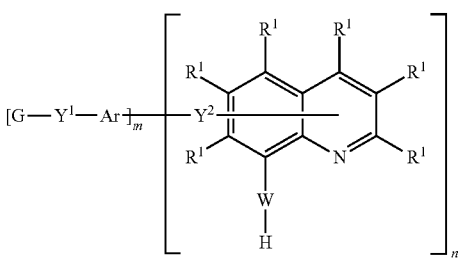

(158)
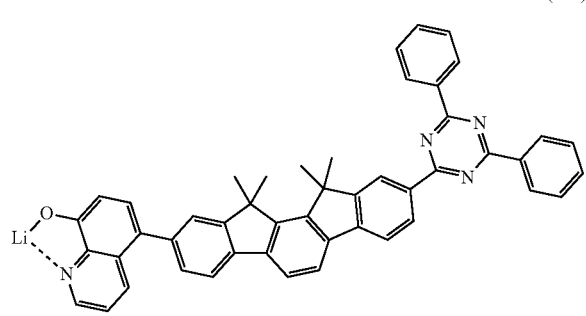

(159)
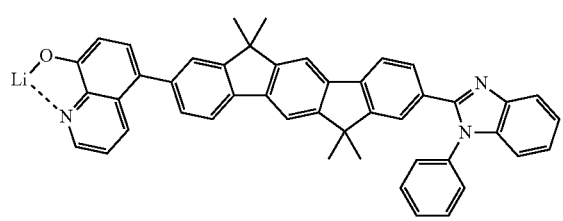

(160)
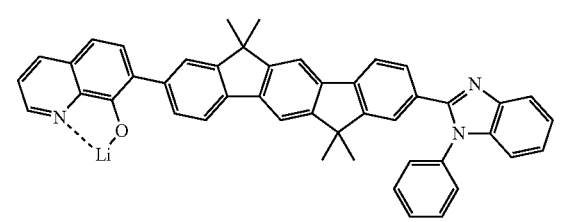

The present invention also relates to a ligand of the following formula (1'):

formula (1')
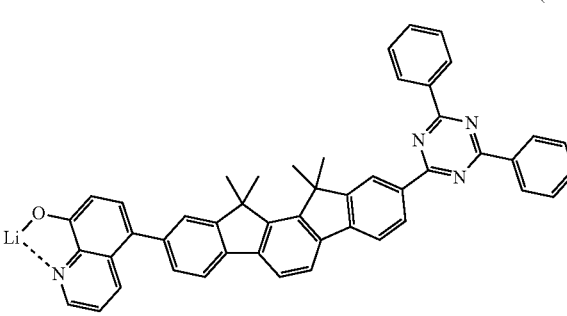

where the symbols and indices used have the same meanings as in the above-mentioned embodiments. Above-mentioned preferred meanings are likewise preferred here.

In a further embodiment of the present invention, the ligand of the formula (1') is used for the preparation of a coordination compound. To this end, the free ligand is reacted, for example, with a corresponding metal salt to give the complex.

Accordingly, the present invention also relates to a process for the preparation of a compound, oligomer or polymer of the formulae (1) to (21). The compounds of the formulae (1) to (21) according to the invention can be prepared by synthetic steps which are generally known to the person skilled in the art. A first step involves the synthesis of the corresponding ligands, which are combined in a further step to give the desired ligand system. This is followed by a reaction with the corresponding metal, which is usually employed as a solution of a suitable metal salt, for example nBuLi/CH$_3$CN or AlCl$_3$/EtOH.

A general synthetic procedure for the preparation of the compound, oligomer or polymer of the formulae (1) to (21) is depicted in Schemes (1) and (2). The central metal M here can be replaced in analogous reactions by one of the other metals mentioned above.

Scheme (1):

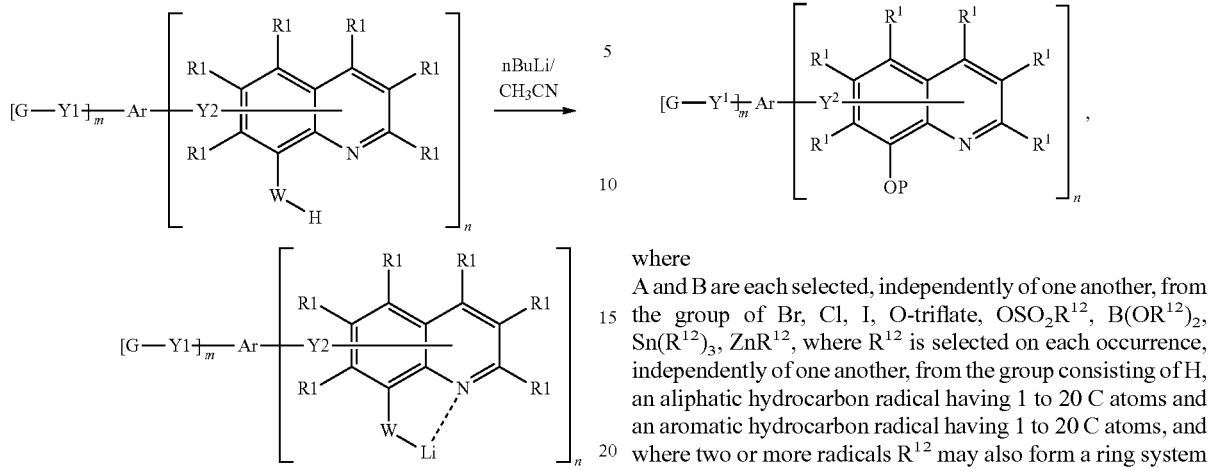

Scheme (2):

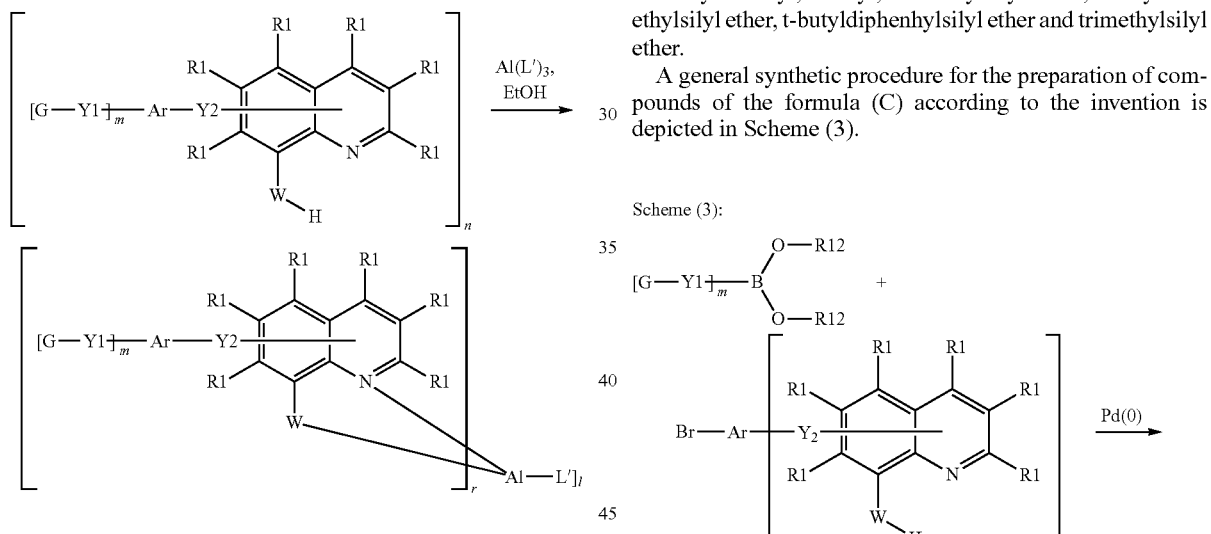

The present invention additionally relates to a process for the preparation of a ligand in which a compound of the following formula (A) is coupled to a compound of the following formula (B) by metal-catalysed Suzuki, Stille, Heck, Negishi, Sonogashira or Kumada cross-coupling reactions, giving a compound of the following formula (C):

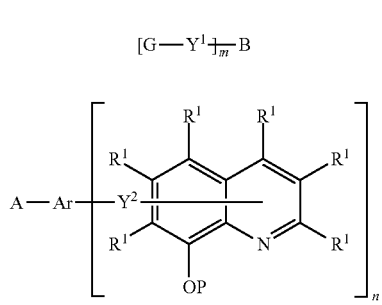

formula (A)

formula (B)

formula (C)

where
A and B are each selected, independently of one another, from the group of Br, Cl, I, O-triflate, $OSO_2R^{12}$, $B(OR^{12})_2$, $Sn(R^{12})_3$, $ZnR^{12}$, where $R^{12}$ is selected on each occurrence, independently of one another, from the group consisting of H, an aliphatic hydrocarbon radical having 1 to 20 C atoms and an aromatic hydrocarbon radical having 1 to 20 C atoms, and where two or more radicals $R^{12}$ may also form a ring system with one another;
P is a hydroxyl-protecting group; and the other symbols and indices have the same meanings as in the above embodiments.

Examples of the hydroxyl-protecting group P are methyl, t-butoxycarbonyl, benzyl, tri-t-butylsilyl ether, t-butyldimethylsilyl ether, t-butyldiphenylsilyl ether and trimethylsilyl ether.

A general synthetic procedure for the preparation of compounds of the formula (C) according to the invention is depicted in Scheme (3).

Scheme (3):

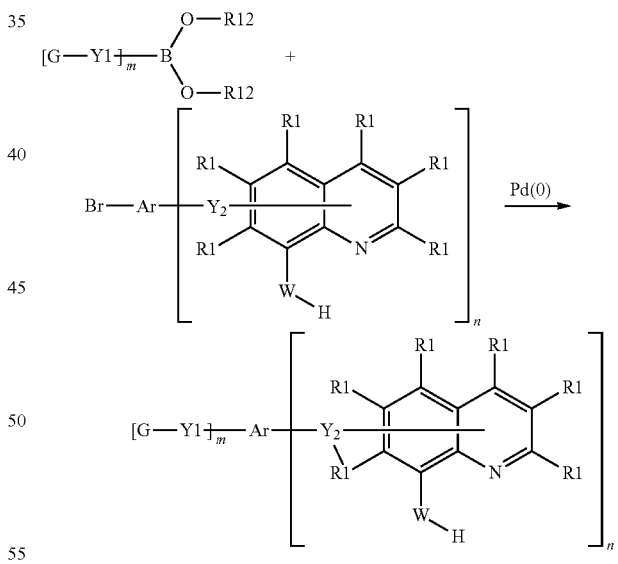

In the case where two radicals $R^{12}$ can form a ring system, these two linked radicals $R^{12}$ preferably represent a divalent aliphatic group having 2 to 8 carbon atoms. Examples thereof are compounds of the following formula —$CH_2$ $(CH_2)_n CH_2$—, where n=0, 1, 2, 3, 4, 5 or 6, where n=0, 1, 2 or 3 is preferred. In the case where more than two radicals $R^{12}$ form a ring system with one another, these radicals $R^{12}$ represent with one another a branched tri-, tetra-, penta- or polyvalent aliphatic group having 6 to 20 carbon atoms.

The present invention also relates to a process for the preparation of a compound of the following formula (B) in which a compound of the following formula (D) is reacted with a compound of the following formula (E) by, for example, metal-catalysed Suzuki, Stille, Heck, Negishi, Sonogashira, Kumada, etc., cross-coupling reactions or by nucleophilic addition onto a carbonyl group, giving a compound of the following formula (C):

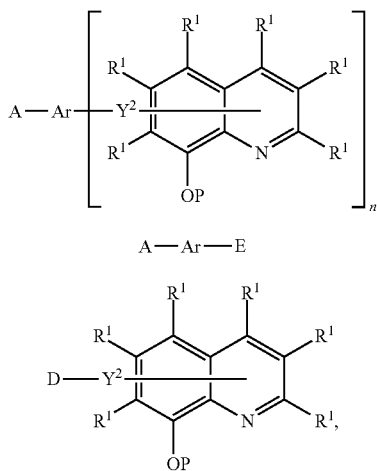

where

D is selected from the group consisting of Br, Cl, I, O-triflate, $OSO_2R^{12}$, $B(OR^{12})_2$, $Sn(R^{12})_3$, $ZnR^{12}$, Li and MgBr;

E is selected from the group consisting of Br, Cl, I, O-triflate, $OSO_2R^{12}$, $B(OR^{12})_2$, $Sn(R^{12})_3$, $ZnR^{12}$, or where E, together with the C atom to which it is bonded, forms a unit C=O;

and the other symbols and indices have the same meanings as in the above embodiments.

A general synthetic procedure for the preparation of compounds of the formula C according to the invention is depicted in Scheme (4).

Scheme (4):

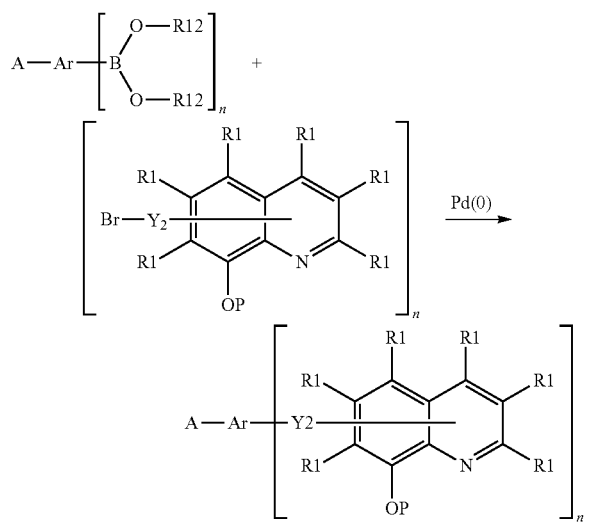

The present invention also relates to the use of a compound of the formula (C) for the preparation of a metal complex. To this end, the hydroxyl-protecting group on the compound of the formula (C) is cleaved off, and the resultant compound of the formula (1') is reacted, for example, with a corresponding metal salt to give the complex.

The synthesis of a compound of the formula (1) is depicted by way of example in Scheme 5.

Scheme 5:

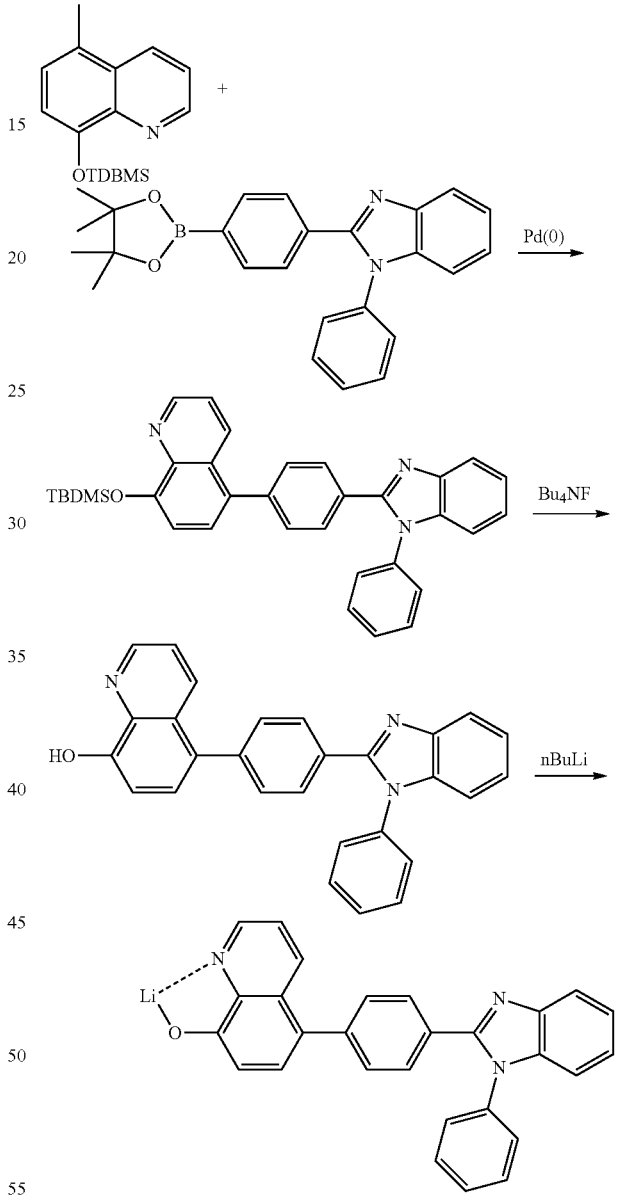

The synthesis of a compound of the formula (X) is shown by way of example in Scheme 6: 2-bromoanthraquinone is converted into the corresponding bromobis(hydroxyquinoline) derivative by reaction with a hydroxy-quinolinemagnesium bromide derivative and subsequent reduction using $SnCl_2$. This product is subsequently converted into the corresponding boronic ester. The resultant compound is reacted with 2,4-diphenyl-1,3,5-triazine by Suzuki coupling. After deprotection of the hydroxyl groups, the compound is reacted with n-BuLi to give the compound according to the invention.

Scheme 6:

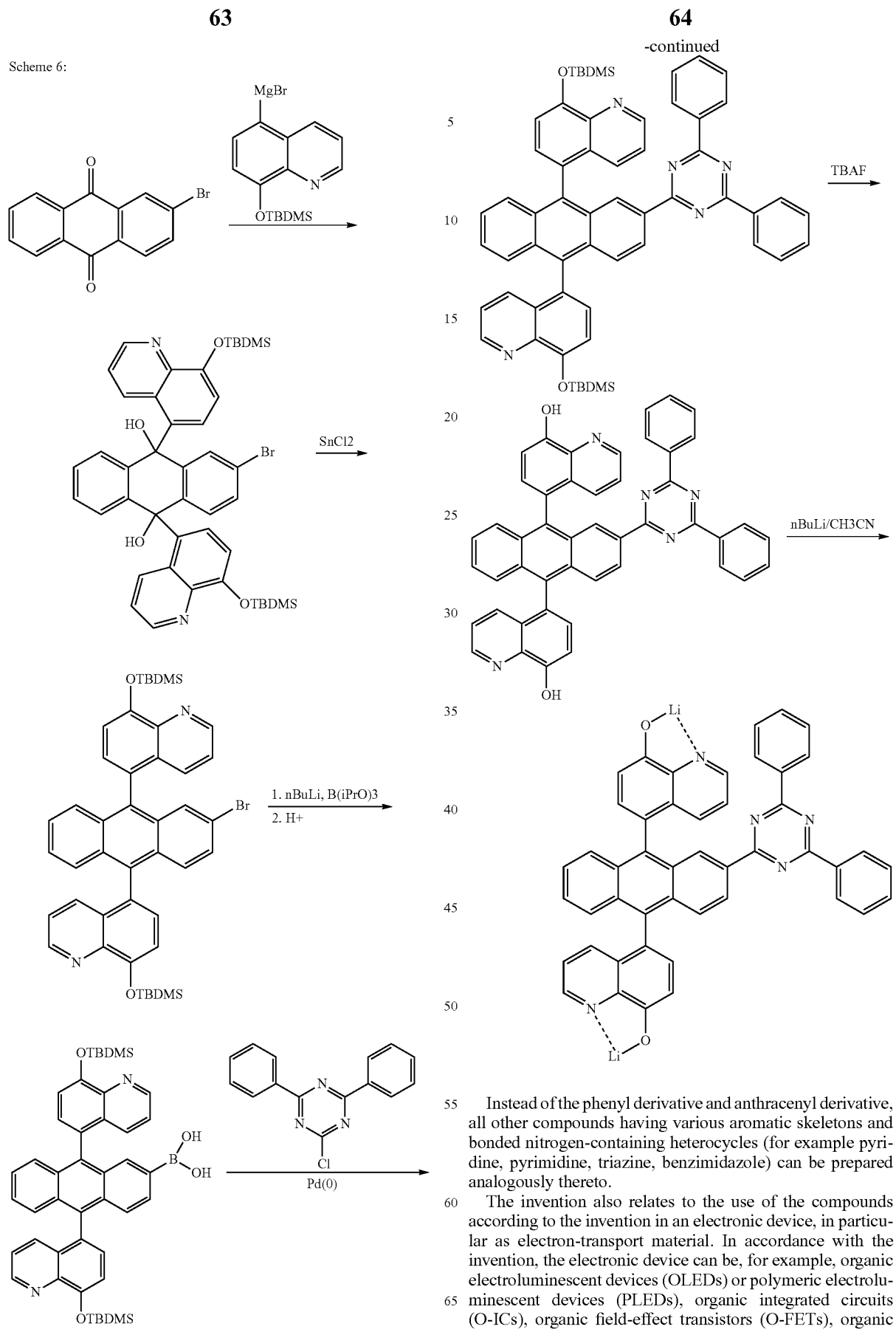

Instead of the phenyl derivative and anthracenyl derivative, all other compounds having various aromatic skeletons and bonded nitrogen-containing heterocycles (for example pyridine, pyrimidine, triazine, benzimidazole) can be prepared analogously thereto.

The invention also relates to the use of the compounds according to the invention in an electronic device, in particular as electron-transport material. In accordance with the invention, the electronic device can be, for example, organic electroluminescent devices (OLEDs) or polymeric electroluminescent devices (PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), but in particular organic electroluminescent devices (OLEDs, PLEDs).

The invention also relates to the use of the compounds according to the invention as charge-transport material and/or charge-injection material, preferably in a corresponding layer. These are, in particular, electron-transport layers or electron-injection layers. The use as charge-blocking material is also possible.

The invention likewise relates to electronic devices, such as, for example, organic electroluminescent devices or polymeric electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), but in particular organic electroluminescent devices (organic light-emitting diodes, OLEDs, PLEDs), comprising one or more compounds, oligomers or polymers of the formulae (1) to (21), as defined above. The electronic device here comprises anode, cathode and at least one layer which comprises at least one organic or organometallic compound. However, the device may also comprise inorganic materials.

The compound, oligomer or polymer of the formulae (1) to (21) is preferably present within one layer in the electronic device.

The invention thus also relates to a layer comprising at least one compound, oligomer or polymer of the formulae (1) to (21), as defined above.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers and/or charge-generation layers. Interlayers, which have, for example, an exciton-blocking function, may likewise be introduced between two emitting layers. However, it should be pointed out that each of these layers does not necessarily have to be present. These layers may comprise a compound, oligomer or polymer of the formulae (1) to (21), as defined above.

In a preferred embodiment of the invention, the compound, oligomer or polymer of the formulae (1) to (21) is employed as compound in an electron-transporting layer. The organic electroluminescent device here may comprise one electron-transporting layer or it may comprise a plurality of electron-transporting layers, where at least one electron-transporting layer comprises at least one compound, oligomer or polymer of the formulae (1) to (21), as defined above. The device may furthermore comprise further charge-transport layers and emitting layers.

Preference is furthermore given to an organic electroluminescent device in which one or more layers are applied by means of a sublimation process, in which the materials are applied by vapour deposition in vacuum sublimation units at an initial pressure of less than $10^{-5}$ mbar, preferably less than $10^{-6}$ mbar. It is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), inkjet printing or nozzle printing. Soluble compounds, which are obtained, for example, by suitable substitution, are necessary for this purpose. Since the compounds according to the invention have high solubility in organic solvents, they are particularly suitable for processing from solution.

These processes are generally known to the person skilled in the art and can be applied by him without problems to organic electroluminescent devices comprising a compound, oligomer or polymer of the formulae (1) to (21), as defined above.

The invention furthermore relates to a formulation or solution comprising at least one compound of the formula (1) to (21) and at least one solvent, preferably an organic solvent.

The compounds according to the invention described above, in particular compounds which are substituted by reactive groups or are functionalised, can be used as monomers for the generation of corresponding oligomers, dendrimers or polymers.

The compounds according to the invention and the organic electroluminescent devices produced therewith are distinguished by the following surprising advantages compared with the prior art:

- The compounds according to the invention have high solubility and can therefore be processed very well from solution.
- Organic electroluminescent devices comprising a compound, oligomer or polymer of the formulae (1) to (21) as electron-transport materials have an excellent lifetime.
- On use of the compounds according to the invention as electron-transport materials, it is not necessary to use a separate electron-injection layer or to dope the electron-transport layer with a further electron-injection material. This represents an advantage in the production of the OLED.
- The compounds according to the invention, employed in organic electroluminescent devices, result in high efficiencies and in steep current/voltage curves at the same time as a low use voltage.

These above-mentioned advantages are not accompanied by an impairment of the other electronic properties.

The invention is explained in greater detail by the following examples, without wishing to restrict it thereby. The person skilled in the art will be able to synthesise further compounds according to the invention without inventive step and employ them in organic electroluminescent devices.

EXAMPLES

The following syntheses are carried out, unless indicated otherwise, under a protective-gas atmosphere in dried solvents.

8-Hydroxyquinoline can be halogenated in the 5-position in accordance with Synthesis, 2006, 8 1325 or Chem. Eur. J., 2005, 11, 6818, and the hydroxyl group can subsequently be protected as silyl ether.

4-Bromobenzaldehyde can be converted into the corresponding bromo-benzimidazole derivative by reaction with N-phenyl-o-phenylenediamine in the presence of Oxone®, and this is subsequently converted into the corresponding boronic ester:

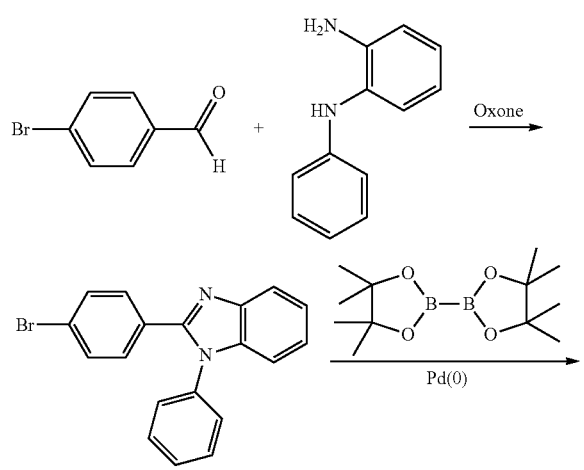

The resultant compound is reacted with the iodohydroxyquinoline derivative by Suzuki coupling. After deprotection of the hydroxyl group, the compound is reacted with n-BuLi to give the compound according to the invention.

Example 1

Synthesis of lithium 5-[4-(1-phenyl-1H-benzimidazol-2-yl)-phenyl]-8-hydroxyquinolate

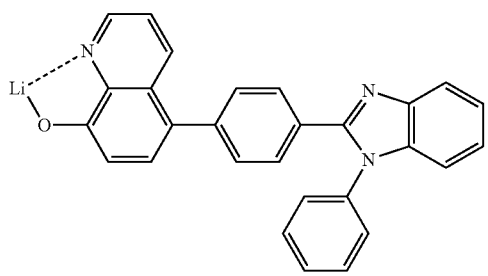

a) 8-Hydroxy-5-iodoquinoline

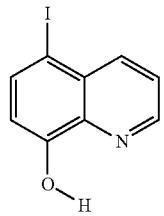 [SMILES: Oc1ccc(I)c2cccnc12]

A solution of 8-hydroxyquinoline (25.0 g, 172.3 mmol), NaI (26.0 g, 172.5 mmol) and NaOH (6.9 g, 172.5 mmol) in MeOH (750 ml) is degassed by passing-through of $N_2$ for 60 min. at room temperature. After cooling to −30° C., a 5% aqueous NaOCl solution (250 ml) is added dropwise. The mixture is stirred vigorously at −30° C. for 30 min. and then neutralised using a 10% aqueous HCl solution. The precipitated product is filtered off. After two recrystallisations from MeOH/heptane (1:1, v/v), a pale-yellow solid is obtained (14 g, 27%).

b) 8-(tert-Butyldimethylsilyloxy)-5-iodoquinoline

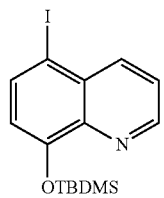 [SMILES: CC(C)(C)[Si](C)(C)Oc1ccc(I)c2cccnc12]

8-Hydroxy-5-iodoquinoline (7.0 g, 25.8 mmol), imidazole (1.85 g, 27.2 mmol) and tert-butyldimethylsilyl chloride (4.28 g, 28.4 mmol) are dissolved in anhydrous $CH_2Cl_2$ (40 ml) under $N_2$. The mixture is stirred vigorously overnight, then diluted with $CH_2Cl_2$ (60 ml) and washed with 5% aqueous HCl (2×30 ml) and water (40 ml). The organic phase is dried over sodium sulfate, and the solvent is distilled off under reduced pressure, leaving a brown liquid. This crude product is purified by flash chromatography on silica (heptane:ethyl acetate 5:1). The end product is isolated as pale-yellow solid (8 g, 80%).

c) 2-(4-Bromophenyl)-1-phenyl-1H-benzimidazole

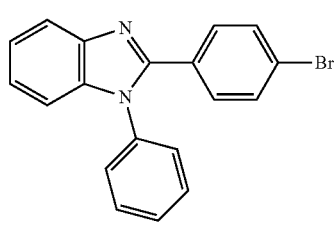 [SMILES: Brc1ccc(-c2nc3ccccc3n2-c2ccccc2)cc1]

N-Phenyl-o-phenylenediamine (50 g, 0.27 mol) is dissolved in anhydrous DMF (400 ml) under $N_2$, and 4-bromobenzaldehyde (45.5 g, 0.25 mol) is added dropwise. The reaction mixture is warmed to 40° C., and Oxone (potassium hydrogen monopersulfate, 98.1 g, 0.16 mol) is added in portions. After the mixture has been stirred at room temperature for 120 min., 1 l of water is added. The precipitated product is filtered off, washed with water and dried in vacuo. Recrystallisation from acetonitrile gives a cream-coloured solid (31 g, 35%).

d) 1-Phenyl-2-[4-(4,4,5,5-tetramethyl-1,3,2-dioxaborolan-2-yl)phenyl]-1H-benzimidazole

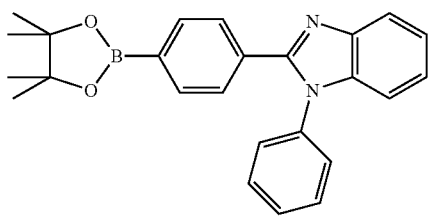 [SMILES: CC1(C)OB(c2ccc(-c3nc4ccccc4n3-c3ccccc3)cc2)OC1(C)C]

A mixture of 2-(4-bromophenyl)-1-phenyl-1H-benzimidazole (20.0 g, 57 mmol), bis(pinacolato)diboron (16.0 g, 63 mmol), potassium acetate (18.6 g, 0.19 mol), $PdCl_2(dppf) \times CH_2Cl_2$ (0.75 g, 1 mmol) and dioxane (360 ml) is degassed for 30 min. The reaction mixture is heated under reflux for 6 h. After cooling to room temperature, the mixture is poured into ice-water (80 ml) and extracted with toluene. The combined organic phases are dried over sodium sulfate, and the solvent is distilled off under reduced pressure, leaving a brown liquid. The end product is isolated as pale-brown solid (22.8 g, 97%).

e) 8-(tert-Butyldimethylsilanyloxy)-5-[4-(1-phenyl-1H-benzimidazol-2-yl)phenyl]quinoline

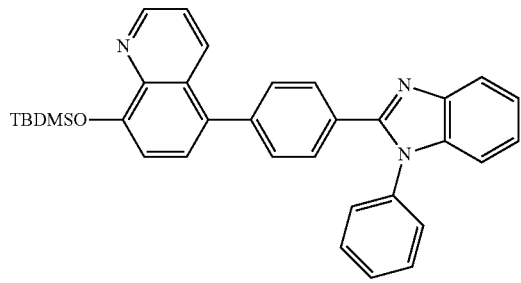 [SMILES: CC(C)(C)[Si](C)(C)Oc1ccc(-c2ccc(-c3nc4ccccc4n3-c3ccccc3)cc2)c2cccnc12]

A mixture of 1-phenyl-2-[4-(4,4,5,5-tetramethyl-1,3,2-dioxaborolan-2-yl)-phenyl]-1H-benzimidazole (8.9 g, 22.4 mmol), 8-(tert-butyldimethylsilyl-oxy)-5-iodoquinoline (7.2 g, 18.69 mmol), toluene (110 ml) and dioxane (110 ml) is degassed by passing through of $N_2$ for 30 min. $Pd(OAc)_2$ (9 mg, 0.04 mmol) and tris-o-tolylphosphine (75.6 mg, 0.25 mmol) is then added, and the mixture is heated at 80° C. for 8 h. After cooling to room temperature, the mixture is diluted with water (100 ml) and extracted with ethyl acetate (3×50 ml). The combined organic phases are dried over sodium sulfate, and the solvent is removed under reduced pressure. The crude product is purified by flash chromatography on silica and crystallisation (7.9 g, 80%).

f) 5-[4-(1-Phenyl-1H-benzimidazol-2-yl)phenyl] quinolin-8-ol

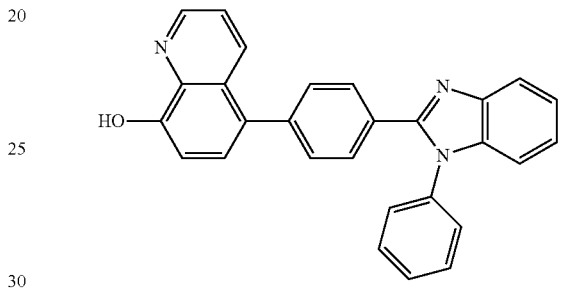

A 1M TBAF solution in THF (22.4 ml, 22.4 mmol) is added dropwise to a solution of 8-(tert-butyldimethylsilanyloxy)-5-[4-(1-phenyl-1H-benzimidazol-2-yl)phenyl]quinoline (7.9 g, 14.90 mmol) in THF (20 ml). After stirring for 4 h, the mixture is washed with 5% aqueous $NH_4Cl$ (100 ml) solution and extracted with ethyl acetate (3×50 ml). The combined organic phases are dried over sodium sulfate, and the solvent is removed under reduced pressure. The crude product is purified by flash chromatography on silica and crystallisation from MeOH (5.9 g, 90%).

g) Lithium 5-[4-(1-phenyl-1H-benzimidazol-2-yl)phenyl]-8-hydroxy-quinolate

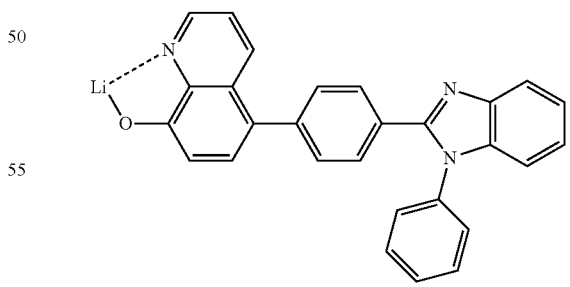

5-[4-(1-Phenyl-1H-benzimidazol-2-yl)phenyl]quinolin-8-ol (2.1 g, 4.8 mmol) is dissolved in acetonitrile (100 ml), and 2.5 M n-butyllithium (1.9 ml, 4.8 mmol) is added. The solution is stirred at room temperature for 1 h. The yellow precipitate is filtered off, washed with acetonitrile and dried in vacuo (1.9 g, 94%).

Example 2

Synthesis of lithium 5,5'-[2-(9,10-anthracen-2-yl)-4,6-diphenyl-1,3,5-triazinyl]bis-8-quinolinate

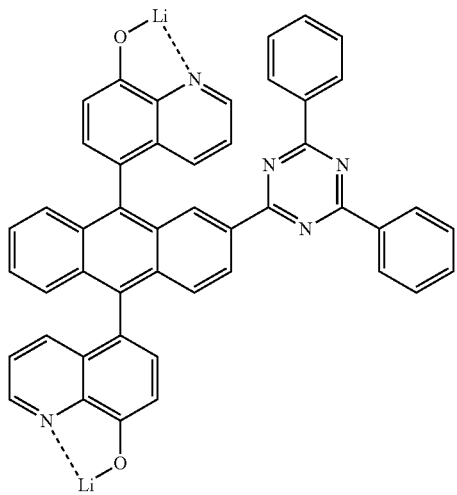

a) 5,5'-(2-Bromoanthracene-9,10-diyl)-8-(tert-butyldimethylsilanyloxy)-bisquinoline

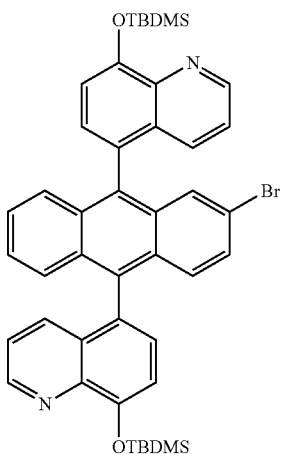 [SMILES: CC(C)(C)[Si](C)(C)Oc1ccc(-c2c3ccccc3c(-c3ccc(O[Si](C)(C)C(C)(C)C)c4ncccc34)c3cc(Br)ccc23)c2cccnc12]

Magnesium (2.3 g, 97 mmol) is initially introduced in 50 ml of dry THF. A solution of 5-bromo-8-hydroxyquinoline (20 g, 89 mmol) in 400 ml of dry THF is added dropwise, the mixture is stirred at 70° C. for 2 h, then allowed to come to room temperature. The resultant Grignard reagent is added dropwise, with ice-cooling, to 2-bromo-9,10-anthraquinone (25.5 g, 89 mmol) in 200 ml of dry THF. After 4 h with ice-cooling, 200 ml of saturated NH₄Cl solution are slowly added dropwise, the mixture is extracted with ethyl acetate, the organic phase is dried over Na₂SO₄ and evaporated in a rotary evaporator. The reaction mixture (52 g) is suspended in DMF (400 ml), tin chloride (67.5 g, 356 mmol) is added, and the mixture is heated to 140° C. 300 ml of EtOH are added, then 50 ml of 2M HCL are added dropwise. The solid is filtered off, washed with EtOH and dried in vacuo (38.2 g, 51%).

b) Bis-(8-(tert-butyldimethysilanyloxyquinolin-5-yl)-9,10-anthracenyl)-2-boronic acid

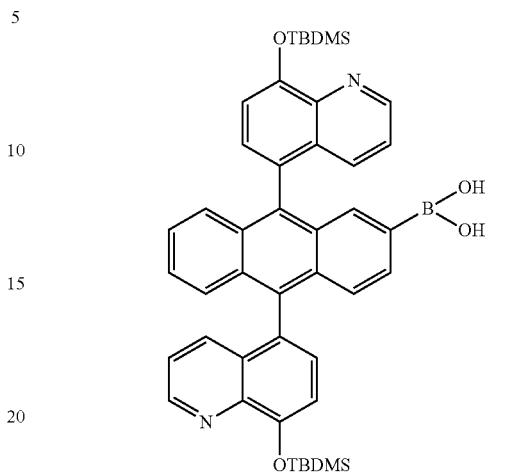

39.3 g (51 mmol) of the bromide from a) are dissolved in 600 ml of dry THF and cooled to −78° C. 26.2 ml (65.7 mmol/2.5 M in hexane) of n-butyllithium are added over the course of about 5 min. at this temperature, and the mixture is subsequently stirred at −78° C. for a further 2.5 h. 7.3 ml (65.7 mmol) of trimethyl borate are added as rapidly as possible at this temperature, and the reaction is allowed to come slowly to RT (about 18 h). The reaction solution is washed with water, and the precipitated solid and the organic phase are dried azeotropically with toluene. The crude product is washed by stirring with toluene/methylene chloride at about 40° C. and filtered off with suction, giving 30.1 g (80%) of the product as white solid.

c) 5,5'-(2-(4,6-Diphenyl-1,3,5-triazinyl)anthracene-9,10-diyl)-8-(tert-butyldimethylsilanyloxy)bisquinoline

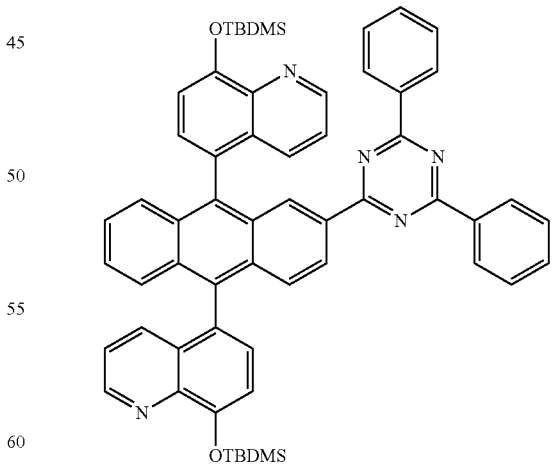

34.4 g (46.8 mmol) of the boronic acid from b), 11.3 g (42.15 mmol) of 2-chloro-4,6-diphenyl-1,3,5-triazine and 9.9 g of sodium carbonate are suspended in 300 ml of dioxane, 300 ml of toluene and 100 ml of water. 2.7 g (2.3 mmol) of Pd(PPh₃)₄ are added to this suspension. The reaction mixture is heated under reflux for 7 h. After cooling, the precipitated solid is filtered off with suction, washed with water and ethanol and dried. The residue is extracted with hot toluene and recrystallised from toluene. Yield: 27.2 g, 70% of theory d) 5,5'-[2-(4,6-Diphenyl-1,3,5-triazinyl)anthracene-9,10-diyl)bis-quinolin-8-ol

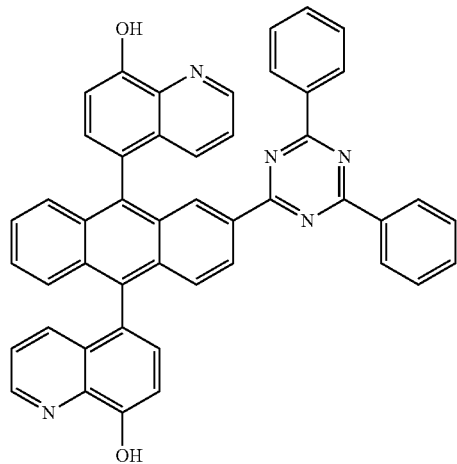 [SMILES: Oc1ccc(-c2c3ccccc3c(-c3ccc(O)c4ncccc34)c3cc(-c4nc(-c5ccccc5)nc(-c5ccccc5)n4)ccc23)c2cccnc12]

A 1M TBAF solution in THF (22.4 ml, 22.4 mmol) is added dropwise to a solution of 5,5'-(2-(4,6-diphenyl-1,3,5-triazinyl)anthracene-9,10-diyl)-8-(tert-butyldimethylsilanyloxy) bisquinoline (13.76 g, 14.90 mmol) in THF (20 ml). After stirring for 4 h, the mixture is washed with 5% aqueous $NH_4Cl$ solution (100 ml) and extracted with ethyl acetate. The combined organic phases are dried over sodium sulfate, and the solvent is removed under reduced pressure. The crude product is purified by flash chromatography on silica and with crystallisation from MeOH (9.25 g, 90%).

e) Lithium 5,5'-[2-(4,6-diphenyl-1,3,5-triazinyl)-(9,10-anthracenediyl)]-bis-8-quinolinolate

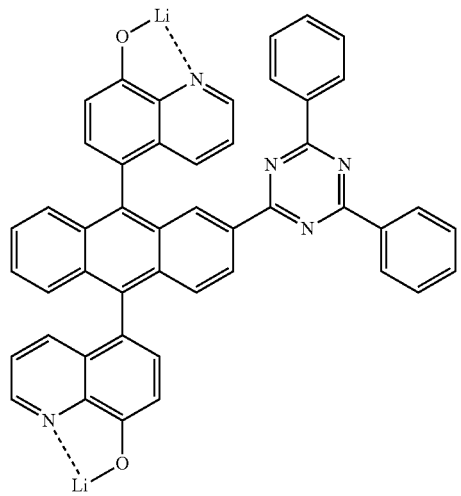

5,5'-[2-(4,6-Diphenyl-1,3,5-triazinyl)anthracene-9,10-diyl)bisquinolin-8-ol (6.95 g, 10 mmol) is dissolved in acetonitrile (300 ml), and 2.5 M n-butyl-lithium (9.9 ml, 25 mmol) is added. The solution is stirred at room temperature for 1 h. The yellow precipitate is filtered off, washed with acetonitrile and dried in vacuo (5.8 g, 80%).

Example 3

Production of OLEDs

OLEDs according to the invention and OLEDs in accordance with the prior art are produced by a general process in accordance with WO 2004/058911, which is adapted to the circumstances described here (layer-thickness variation, materials used).

The results for various OLEDs are presented in Examples 4 to 23 below (see Table 1 and 2). Glass plates coated with structured ITO (indium tin oxide) in a thickness of 150 nm are coated with 20 nm of PEDOT (poly(3,4-ethylenedioxy-2,5-thiophene), spin-coated from water; purchased from H. C. Starck, Goslar, Germany) for improved processing. These coated glass plates form the substrates to which the OLEDs are applied. The OLEDs have the following layer structure: substrate ITO/hole-transport layer (HTL 140 nm)/interlayer (IL 5 nm)/electron-blocking layer (EBL 20 nm)/emission layer (EML (H1 or H2+x % by vol. of D1 or D2) z nm)/electron-transport layer (ETL y nm)/optional electron-injection layer (EIL 1 nm) and finally a cathode. The cathode is formed by an aluminium layer with a thickness of 100 nm. The precise structure of the OLEDs is shown in Table 1. The materials used for the production of the OLEDs are shown in Table 3.

All materials are applied by thermal vapour deposition in a vacuum chamber. The emission layer here always consists of at least one matrix material (=host material) and an emitting dopant (=emitter), which is admixed with the matrix material or the matrix materials in a certain proportion by volume by co-evaporation. An indication such as H1:D1 (95%:5%) here means that material H1 is present in the layer in a proportion by volume of 95% and D1 is present in the layer in a proportion by volume of 5%. The electron-transport layer can also consist analogously of a mixture of two materials.

The OLEDs are characterised by standard methods. For this purpose, the electroluminescence spectra, current/voltage/luminance characteristic lines (IUL characteristic lines) and the lifetime are measured. The lifetime is defined as the time after which the luminous density has dropped to a certain proportion from a certain initial luminous density $I_0$. The indication LD50 means that the said lifetime is the time at which the luminous density has dropped to $0.5 \cdot I_0$ (to 50%), i.e. from, for example, 6000 $cd/m^2$ to 3000 $cd/m^2$. The current efficiency (cd/A) and the power efficiency (lm/W) are calculated from the IUL characteristic lines.

The compounds according to the invention can be employed, inter alia, as electron-transport material for fluorescent and phosphorescent OLEDs. Compounds ETM2, ETM3 and ETM4 according to the invention are used here. The comparison in accordance with the prior art used is compound ETM1. The results for the OLEDs are summarised in Table 2. Ex. 1-9 show OLEDs comprising materials in accordance with the prior art and serve as comparative examples. The OLEDs according to the invention in Ex. 10-23 exhibit the advantages on use of compounds of the formula (1) according to the invention. The use of compounds according to the invention enables improvements to be achieved, compared with the prior art, in the operating voltage, efficiency and lifetime of the components Compared with the reference components, the electrical characteristic data are in all cases comparable or better. With an otherwise identical layer structure, the components according to the invention exhibit improved performance data.

TABLE 1

Structure of the OLEDs

| Ex. | EML | ETL | EIL |
|---|---|---|---|
| 4 (comp.) | H1:D1 (95%:5%) 30 nm | ETM1 20 nm | — |
| 5 (comp.) | H1:D1 (95%:5%) 30 nm | ETM1 20 nm | EIL1 1 nm |
| 6 (comp.) | H1:D1 (95%:5%) 30 nm | ETM1:EIL1 (50:50) 20 nm | — |
| 7 (comp.) | H2:D2 (85%:15%) 40 nm | ETM1 30 nm | — |
| 8 (comp.) | H2:D2 (85%:15%) 40 nm | ETM1 30 nm | EIL1 1 nm |
| 9 (comp.) | H2:D2 (85%:15%) 40 nm | ETM1:EIL1 (50:50) 30 nm | — |
| 10 | H1:D1 (95%:5%) 30 nm | ETM2 20 nm | — |
| 11 | H1:D1 (95%:5%) 30 nm | ETM3 20 nm | — |
| 12 | H1:D1 (95%:5%) 30 nm | ETM4 20 nm | — |
| 13 | H1:D1 (95%:5%) 30 nm | ETM1 20 nm | ETM2 |
| 14 | H1:D1 (95%:5%) 30 nm | ETM1 20 nm | ETM3 |
| 15 | H1:D1 (95%:5%) 30 nm | ETM1:EMT3 (50:50) 20 nm | |
| 16 | H1:D1 (95%:5%) 30 nm | ETM1:ETM4 (50:50) 20 nm | |
| 17 | H2:D2 (85%:15%) 40 nm | ETM2 20 nm | — |
| 18 | H2:D2 (85%:15%) 40 nm | ETM3 20 nm | — |
| 19 | H2:D2 (85%:15%) 40 nm | ETM4 20 nm | — |
| 20 | H2:D2 (85%:15%) 40 nm | ETM1 20 nm | ETM2 |
| 21 | H2:D2 (85%:15%) 40 nm | ETM1 20 nm | ETM3 |
| 22 | H2:D2 (85%:15%) 40 nm | ETM1:EMT3 (50:50) 20 nm | |
| 23 | H2:D2 (85%:15%) 40 nm | ETM1:ETM4 (50:50) 20 nm | |

TABLE 2

Results for the OLEDs

| Ex. | Voltage [V] for 1000 cd/m2 | Efficiency [cd/A] at 1000 cd/m2 | CIE x/y at 1000 cd/m² | LD50 $I_0 =$ 6000 cd/m² |
|---|---|---|---|---|
| 4 (comp.) | 7.5 | 4.3 | 0.146  0.167 | 50 |
| 10 | 4.4 | 8.1 | 0.143  0.161 | 130 |
| 11 | 4.8 | 7.4 | 0.143  0.162 | 100 |
| 12 | 4.0 | 8.3 | 0.141  0.160 | 160 |
| 5 (comp.) | 4.4 | 7.8 | 0.142  0.160 | 160 |
| 13 | 4.3 | 8.1 | 0.142  0.161 | 180 |
| 14 | 4.0 | 8.3 | 0.142  0.161 | 210 |
| 6 (comp.) | 4.3 | 7.9 | 0.142  0.162 | 230 |
| 15 | 3.9 | 8.6 | 0.143  0.161 | 260 |
| 16 | 4.0 | 8.8 | 0.143  0.162 | 280 |
| 7 (comp.) | 7.1 | 14.8 | 0.34  0.58 | 110 |
| 17 | 4.8 | 36.3 | 0.35  0.61 | 280 |
| 18 | 4.6 | 42.4 | 0.35  0.61 | 360 |
| 19 | 3.9 | 46.5 | 0.35  0.61 | 380 |
| 8 (comp.) | 3.8 | 39.3 | 0.35  0.60 | 670 |
| 20 | 3.7 | 40.1 | 0.35  0.60 | 750 |
| 21 | 3.6 | 40.6 | 0.35  0.60 | 780 |
| 9 (comp.) | 3.7 | 42.5 | 0.35  0.61 | 860 |
| 22 | 3.8 | 45.3 | 0.35  0.61 | 950 |
| 23 | 3.5 | 48.7 | 0.35  0.61 | 1030 |

TABLE 3

Structural formulae of the materials used

IL

HTL

TABLE 3-continued
Structural formulae of the materials used
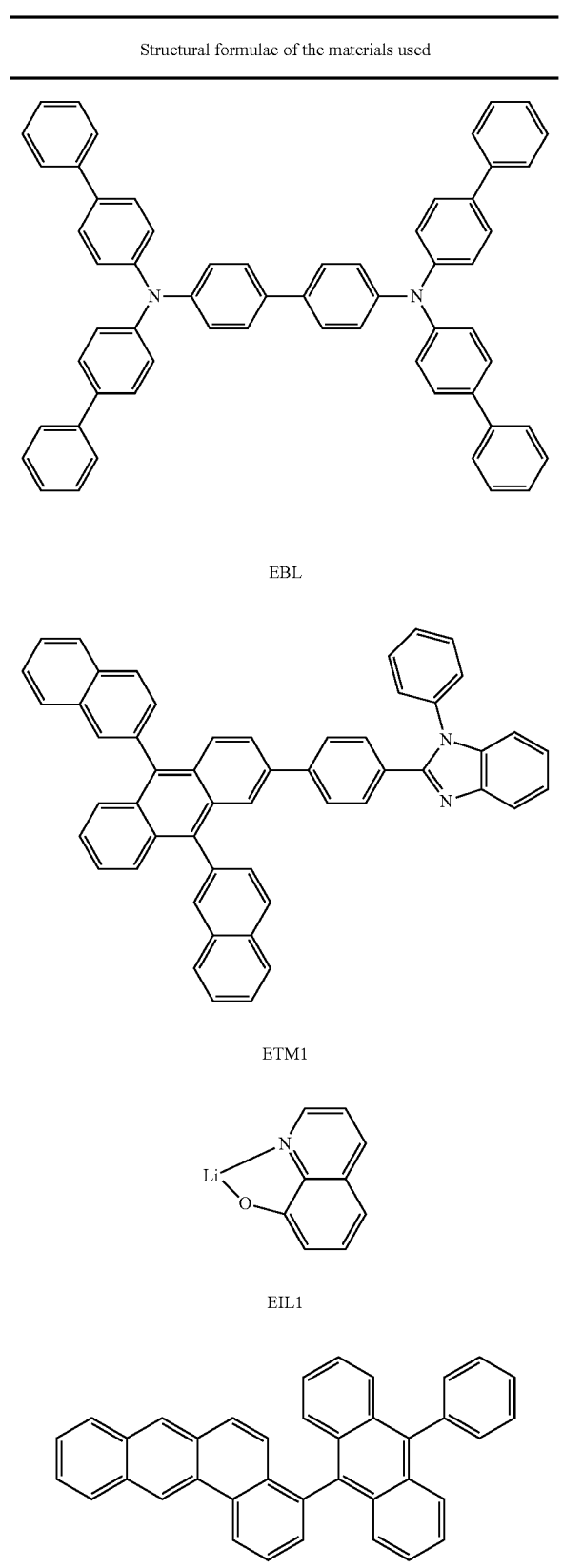
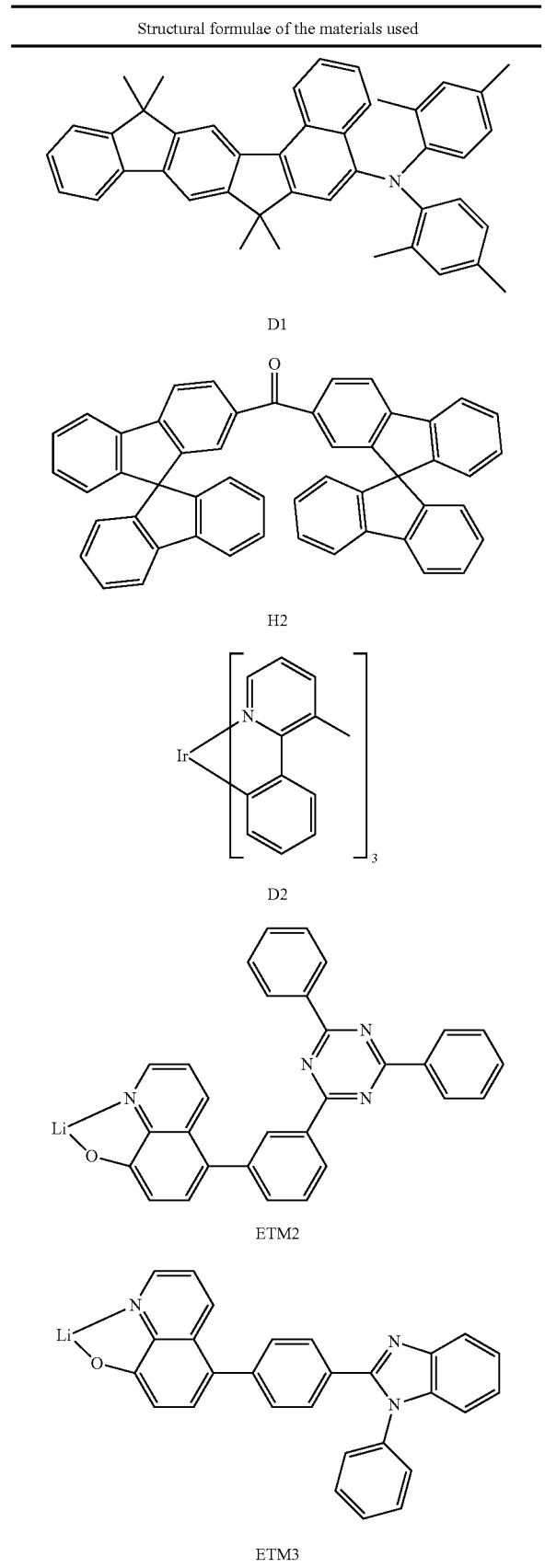

TABLE 3-continued

Structural formulae of the materials used

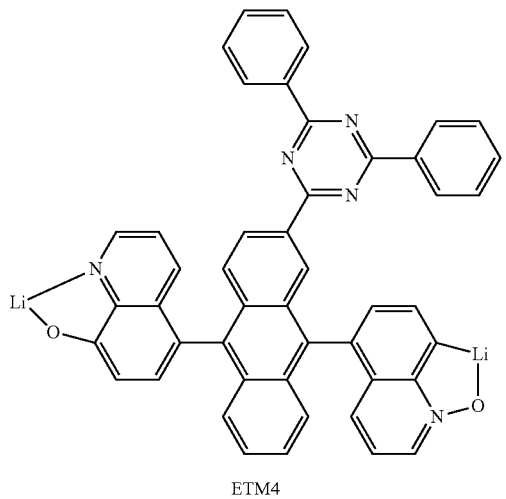

ETM4

The invention claimed is:

1. A compound of the general formula (1) or (2),

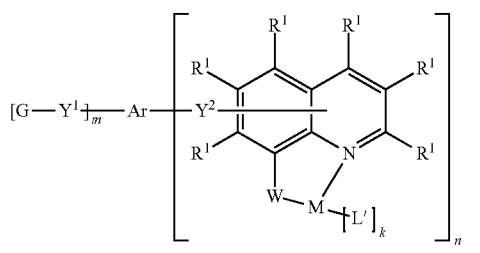

formula (1)

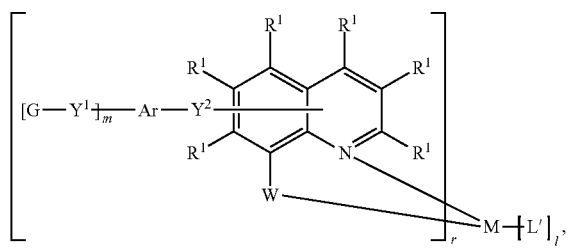

formula (2)

where the symbols and indices used have the following meanings:

G is, identically or differently on each occurrence, a group of the following formula (a), (b) or (c):

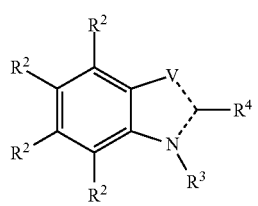

formula (a)

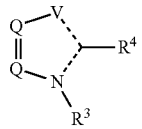

formula (b)

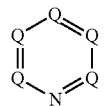

formula (c)

Q is, identically or differently on each occurrence, a N or $CR^3$,

V is selected from the group consisting of O, S, N, $CR^4$ and $NR^4$, with the proviso that, if V is equal to O, S or $NR^4$, $R^3$ represents a non-bonding electron pair;

the two dashed bonds in formula (a) and (b) mean that one of the bonds is a single covalent bond and the other is a double covalent bond;

$R^1$ is selected identically or differently on each occurrence, from the group defined for $R^2$, $R^3$ or $R^4$; where one $R^1$ is not present, and the quinoline unit is bonded to $Y^2$ at this position;

$R^2$, $R^3$ and $R^4$ are, identically or differently on each occurrence, a H, D, F, Cl, Br, I, CHO, $N(Ar^1)_2$, $C(=O)Ar^1$, $P(=O)(Ar^1)_2$, $S(=O)Ar^1$, $S(=O)_2Ar^1$, $CR^5=CR^5Ar^1$, CN, $NO_2$, $Si(R^5)_3$, $B(OAr^1)_2$, $B(OR^5)_2$, $OSO_2R^5$, OH, a saturated or unsaturated, straight-chain, branched or cyclic $C_{1-40}$-alkyl group, $C_{1-40}$-alkoxy group or $C_{1-40}$-thioalkyl group, each of which is optionally substituted by one or more radicals $R^5$, where one or more non-adjacent $CH_2$ groups is optionally replaced by $R^5C=CR^5$, $Si(R^5)_2$, $Ge(R^5)_2$, $Sn(R^3)_2$, C=O, C=S, C=Se, $C=NR^5$, $P(=O)(R^5)$, SO, $SO_2$, $NR^5$, O, S or $CONR^5$, and where one or more H atoms is optionally replaced by D, F, Cl, Br, I, CN or $NO_2$, an aromatic or heteroaromatic ring system having 5 to 60 aromatic ring atoms, which is optionally substituted by one or more radicals $R^6$, an aryloxy or heteroaryloxy group having 5 to 60 aromatic ring atoms, which is optionally substituted by one or more radicals $R^6$, and a combination of these systems; where one of the substituents $R^2$, $R^3$ or $R^4$ is not present on the group G, and the group G is bonded to $Y^1$ at this position;

W is, identically or differently on each occurrence, an O, S or $NR^B$, where $R^8$ is selected from the group defined for $R^2$, $R^3$ or $R^4$;

$Y^1$ and $Y^2$ are each, independently of one another, either not present, so that the groups bonded thereto are linked directly to one another by a single covalent bond, or are a saturated, linear, branched or cyclic $C_{1-40}$-alkyl group or an aromatic or heteroaromatic ring system having 5 to 60 ring atoms, which is optionally substituted by one or more radicals $R^6$;

Ar is an aromatic or heteroaromatic ring system having 5 to 60 aromatic ring atoms, which is optionally substituted by one or more radicals $R^9$, where $R^9$ is selected from the group defined for $R^2$, $R^3$ or $R^4$;

$Ar^1$ is, identically or differently on each occurrence, an aromatic or heteroaromatic ring system having 5 to 30 aromatic ring atoms, which is optionally substituted by one or more radicals $R^7$, where, in addition, two radicals Ar¹ which are bonded to the same nitrogen or phosphorus atom is optionally linked to one another by a single bond or a bridge selected from the group consisting of B(R⁷), C(R⁷)₂, Si(R⁷)₂, C=O, C=NR⁷, C=C(R⁷)₂, O, S, S=O, SO₂, N(R⁷), P(R⁷) and P(=O)R⁷;

R⁵ is, identically or differently on each occurrence, a H, D, a saturated or unsaturated, linear, branched or cyclic $C_{1-20}$-alkyl group, in which one or more H atoms is optionally replaced by D or F, or an aromatic or heteroaromatic ring system having 5 to 20 ring atoms, in which one or more H atoms is optionally replaced by F, and which is optionally substituted by one or more radicals R⁶;

R⁶ is, identically or differently on each occurrence, a H, D, F, Cl, Br, I, CHO, N(Ar¹)₂, C(=O)Ar¹, P(=O)(Ar¹)₂, S(=O)Ar¹, S(=O)₂Ar¹, CR⁷=CR⁷Ar¹, CN, NO₂, Si(R⁷)₃, B(OAr¹)₂, B(OR⁷)₂, OSO₂R⁷, OH, or a saturated or unsaturated, straight-chain, branched or cyclic $C_{1-40}$-alkyl group, $C_{1-40}$-alkoxy group or $C_{1-40}$-thioalkyl group, each of which is optionally substituted by one or more radicals R⁷, where one or more non-adjacent CH₂ groups is optionally replaced by R⁷C=CR⁷, C≡C, Si(R⁷)₂, Ge(R⁷)₂, Sn(R⁷)₂, C=O, C=S, C=Se, C=NR⁷, P(=O)(R⁷), SO, SO₂, NR⁷, O, S or CONR⁷, and where one or more H atoms is optionally replaced by D, F, Cl, Br, I, CN or NO₂;

R⁷ is identically or differently on each occurrence, a H, D, a saturated or unsaturated, linear, branched or cyclic $C_{1-20}$-alkyl group, in which one or more H atoms is optionally replaced by F or D, and an aromatic or heteroaromatic ring system having 5 to 20 ring atoms, in which one or more H atoms is optionally replaced by F or D;

M is, identically or differently on each occurrence, a metal selected from Li, Al or Zr;

L' is, identically or differently on each occurrence, a monodentate or bidentate ligand;

m is, identically or differently on each occurrence, 0, 1, 2, 3 or 4, with the proviso that at least one index m is >0;

n is 1, 2, 3 or 4;

r is 1, 2, 3 or 4;

k is, identically or differently on each occurrence, 0, 1, 2, 3, 4, 5 or 6; and l is 0, 1, 2, 3, 4, 5 or 6.

2. The compound according to claim 1, wherein the following applies to compounds of the formula (I):
if M is a metal having two coordination sites, then k is equal to 0;
if M is a metal having six coordination sites and L' is a monodentate ligand, then k is equal to 4;
if M is a metal having eight coordination sites and L' is a monodentate ligand, then k is equal to 6;
if M is a metal having six coordination sites and L' is a bidentate ligand, then k is equal to 2;
if M is a metal having eight coordination sites and L' is a bidentate ligand, then k is equal to 3;
and wherein the following applies to compounds of the formula (II):
if M is a metal having two coordination sites and r is equal to 1, then l is equal to 0;
if M is a metal having six coordination sites, L' is a monodentate ligand and r is equal to 1, then l is equal to 4;
if M is a metal having eight coordination sites, L' is a monodentate ligand and r is equal to 1, then l is equal to 6;
if M is a metal having six coordination sites, L' is a monodentate ligand and r is equal to 2, then l is equal to 2;
if M is a metal having eight coordination sites, L' is a monodentate ligand and r is equal to 2, then l is equal to 4;
if M is a metal having six coordination sites and r is equal to 3, then l is equal to 0;
if M is a metal having eight coordination sites, L' is a monodentate ligand and r is equal to 3, then l is equal to 2;
if M is a metal having eight coordination sites and r is equal to 4, then l is equal to 0;
if M is a metal having six coordination sites, L' is a bidentate ligand and r is equal to 1, then l is equal to 2;
if M is a metal having eight coordination sites, L' is a bidentate ligand and r is equal to 1, then l is equal to 3;
if M is a metal having six coordination sites, L' is a bidentate ligand and r is equal to 2, then l is equal to 1;
if M is a metal having eight coordination sites, L' is a bidentate ligand and r is equal to 2, then l is equal to 2;
if M a metal having eight coordination sites, L' a bidentate ligand and r equal to 3, then l is equal to 1;
if M a metal having eight coordination sites, L' bidentate ligand and r equal to 4, then l is equal to 0.

3. The compound according to claim 1, wherein the group Ar is selected from the following formulae, each of which may also be substituted by one or more radicals R⁹:

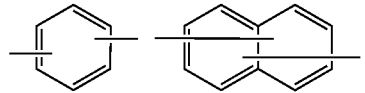

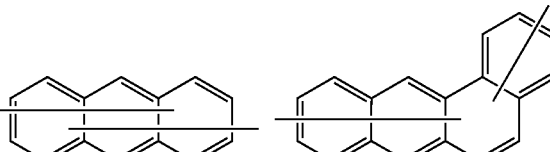

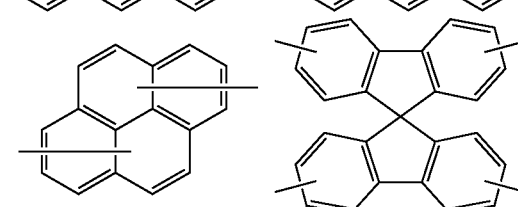

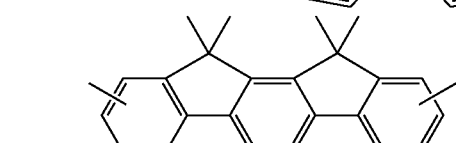

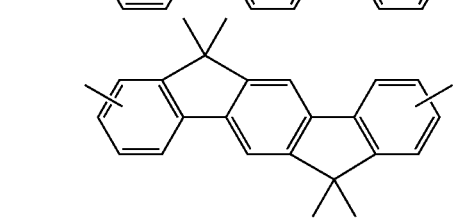

4. The compound according to claim 1, wherein the group G is selected from the following formulae, each of which may also be substituted by one or more substituents R², R³ or R⁴:

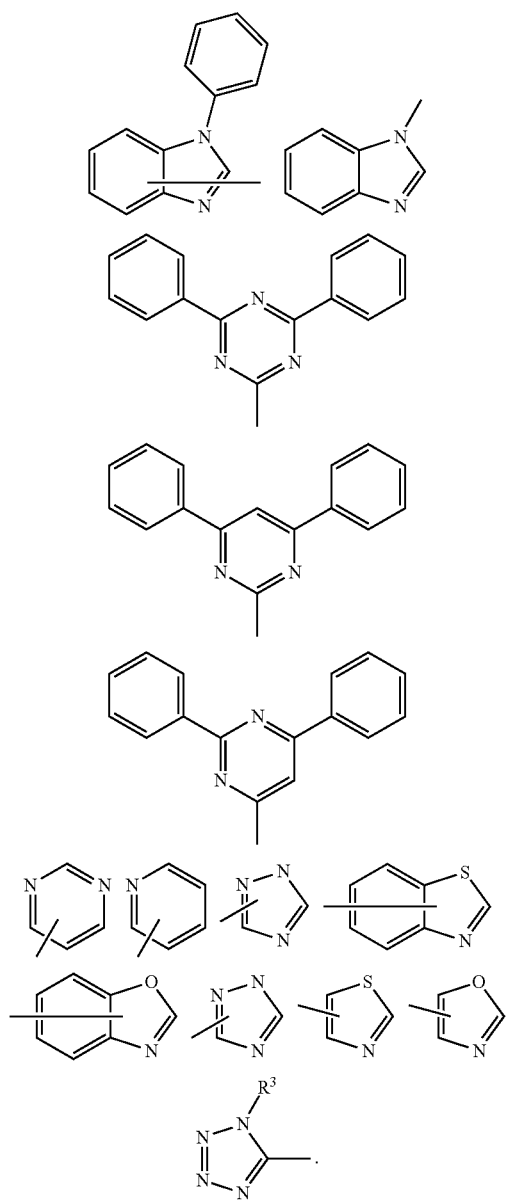
5. The compound according to claim 1, wherein the groups $Y^1$ and $Y^2$, identically or differently on each occurrence, are not present or are selected from the following groups, each of which may also be substituted by one or more substituents $R^6$:
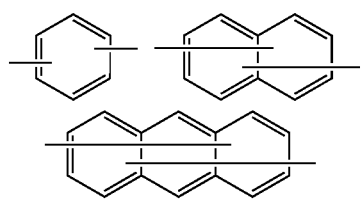
6. The compound according to claim 1, selected from the compounds of the formulae (3) to (12):
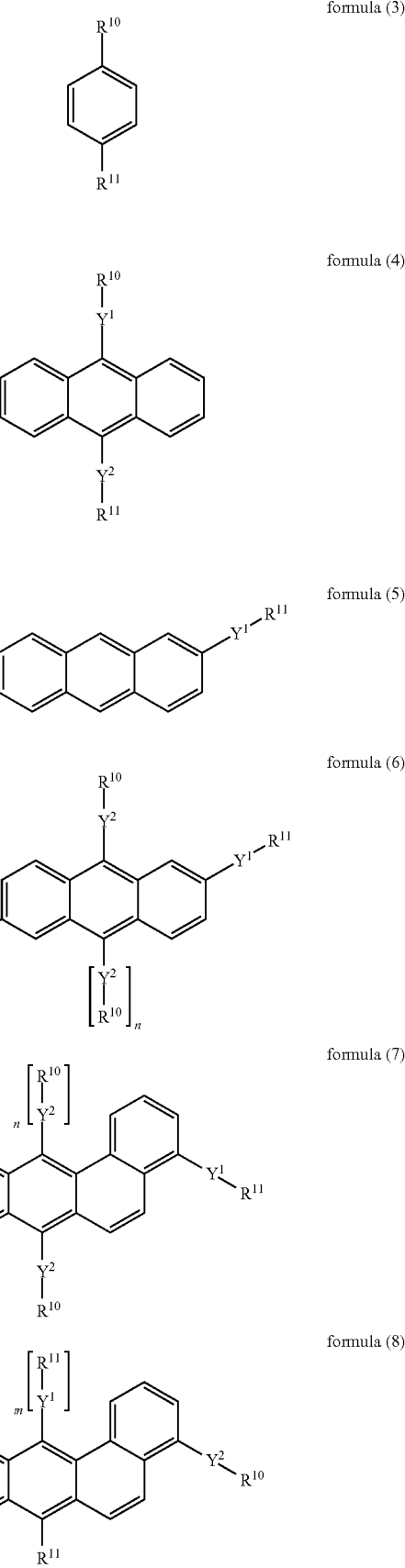

formula (9)
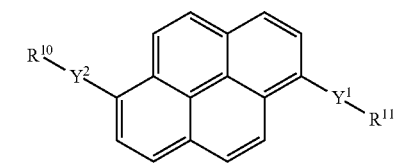

formula (10)
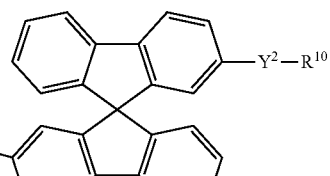

formula (11)
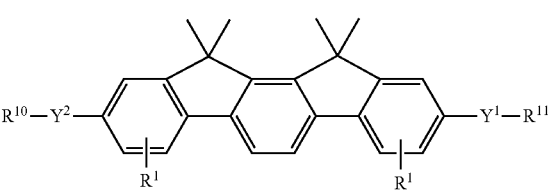

formula (12)
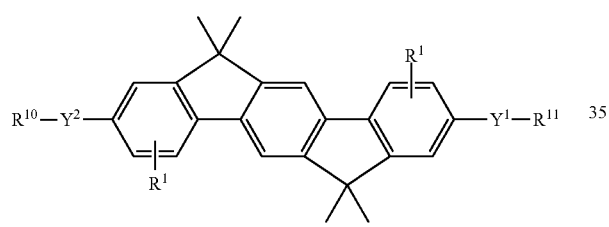

where the symbols used have the following meanings:

the same meaning as defined in claim 1;

$R^{10}$ is, identically or differently on each occurrence, either H or a radical of the following formula (d):

formula (d)
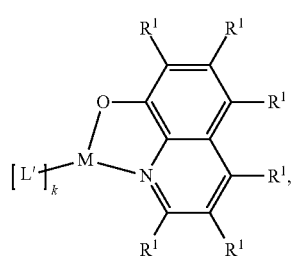

where L', k and $R^1$ have the same meanings as defined in claim 1, with the proviso that one $R^1$ is not present, and the compound of the formula (d) is bonded to the compound of the formula (3) to (12) at this position;

$R^{11}$ is, identically or differently on each occurrence, either H or a radical of the following formula (e) or (f):

formula (e)
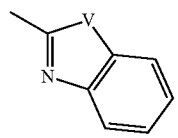

formula (f)
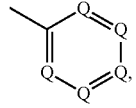

where V is selected from the group consisting of O, S and $NR^4$ and Q is selected from the group consisting of N and $CR^3$, where at least one Q, stand for N, and where $R^3$ has the same meaning as defined in claim 1;

with the proviso that both at least one $R^{10}$ in each formula and also at least one $R^{11}$ in each formula is other than H.

7. The compound according to claim 6, wherein $R^{10}$ is selected from the following formulae, where the bond drawn in indicates the position of the link to $Y^2$:

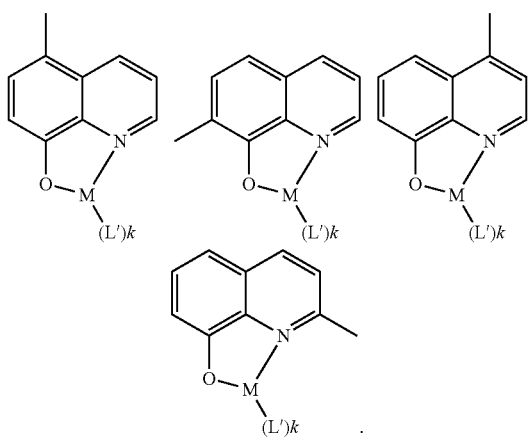

8. An oligomer or polymer which comprises the compound according to claim 1, containing a structural unit of the general formula (13) to (21):

formula (13)

$$\begin{array}{c} | \\ L \\ | \\ Ar-[Y^1-G]_m \\ | \\ L \\ | \\ M-[L']_a \\ | \end{array}$$

formula (14)

$$\begin{array}{c} | \\ L \\ | \\ -L-Ar-[Y^1-G]_m \\ | \\ L \\ | \\ M-[L']_a \\ | \end{array}$$

-continued

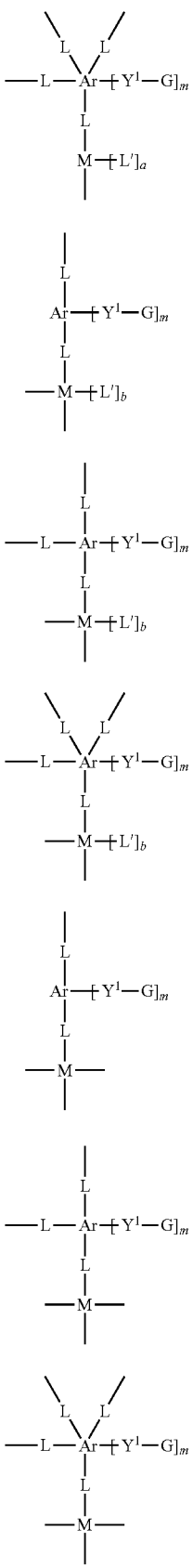

formula (15)

formula (16)

formula (17)

formula (18)

formula (19)

formula (20)

formula (21)

where the symbols Ar, L', $Y^1$ and G and the index m have the same meanings as defined in claim 1, and the other symbols and indices have the following meanings:

M is a divalent metal;

L is a bidentate ligand of the following formula (g):

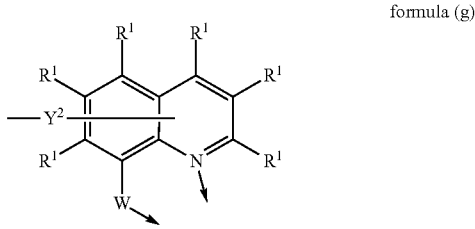

formula (g)

where the bond dash leading away from $Y^2$ represents a bond to Ar in the structural units of the formulae (13) to (21), and the arrows leading away from W and N represent a coordination bond to M, and the symbols $Y^2$, W and $R^1$ have the same meanings as defined in claim 1, where one $R^1$ is not present and the quinoline unit is bonded to $Y^2$ at this position;

a is 0, 1 or 2;

b is 0 or 1;

with the proviso that the bond dashes leading away from L in the structural units of the formulae (13) to (21) represent a bond to M of a further structural unit, and the bond dashes leading away from M in the structural units of the formulae (13) to (21) represent a bond to L of a still further structural unit.

9. The compound according to claim 1, wherein L' is a bidentate ligand which may also be substituted.

10. The compound according to claim 1, wherein L' is a 8-hydroxyquinoline, which may also be substituted.

11. A process for the preparation of the compound according to claim 1 which comprises reacting a compound of the formula (1') with a compound of the metal M

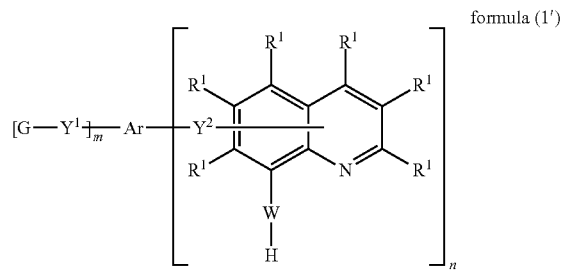

formula (1')

wherein $R^1$ is selected identically or differently on each occurrence, from the group defined for $R^2$, $R^3$ or $R^4$; where one $R^1$ is not present, and the quinoline unit is bonded to $Y^2$ at this position;

$R^2$, $R^3$ and $R^4$ are, identically or differently on each occurrence, a H, D, F, Cl, Br, I, CHO, $N(Ar^1)_2$, $C(=O)Ar^1$, $P(=O)(Ar^1)_2$, $S(=O)Ar^1$, $S(=O)_2Ar^1$, $CR^5=CR^5Ar^1$, CN, $NO_2$, $Si(R^5)_3$, $B(OAr^1)_2$, $B(OR^5)_2$, $OSO_2R^5$, OH, a saturated or unsaturated, straight-chain, branched or cyclic $C_{1-40}$-alkyl group, $C_{1-40}$-alkoxy group or $C_{1-40}$-thioalkyl group, each of which is optionally substituted by one or more radicals $R^3$, where one or more non-adjacent $CH_2$ groups is optionally replaced by $R^5C=CR^5$, $Si(R^5)_2$, $Ge(R^5)_2$, $Sn(R^5)_2$, C=O, C=S, C=Se, C=NR$^5$, P(=O)(R$^5$), SO, SO$_2$, NR$^5$, O, S or CONR$^5$, and where one or more H atoms is optionally replaced by D, F, Cl, Br, I, CN or NO$_2$, an aromatic or heteroaromatic ring system having 5 to 60 aromatic ring atoms, which is optionally substituted by one or more radicals R$^6$, an aryloxy or heteroaryloxy group having 5 to 60 aromatic ring atoms, which is optionally substituted by one or more radicals R$^6$, and a combination of these systems; where one of the substituents R$^2$, R$^3$ or R$^4$ is not present on the group G, and the group G is bonded to Y$^1$ at this position;

W is, identically or differently on each occurrence, an O, S or NR$^B$, where R$^8$ is selected from the group defined for R$^2$, R$^3$ or R$^4$;

Y$^1$ and Y$^2$ are each, independently of one another, either not present, so that the groups bonded thereto are linked directly to one another by a single covalent bond, or are a saturated, linear, branched or cyclic C$_{1-40}$-alkyl group or an aromatic or heteroaromatic ring system having 5 to 60 ring atoms, which is optionally substituted by one or more radicals R$^6$;

Ar is an aromatic or heteroaromatic ring system having 5 to 60 aromatic ring atoms, which is optionally substituted by one or more radicals R$^9$, where R$^9$ is selected from the group defined for R$^2$, R$^3$ or R$^4$;

Ar$^1$ is, identically or differently on each occurrence, an aromatic or heteroaromatic ring system having 5 to 30 aromatic ring atoms, which is optionally substituted by one or more radicals R$^7$, where, in addition, two radicals Ar$^1$ which are bonded to the same nitrogen or phosphorus atom is optionally linked to one another by a single bond or a bridge selected from the group consisting of B(R$^7$), C(R$^7$)$_2$, Si(R$^7$)$_2$, C=O, C=NR$^7$, C=C(R$^7$)$_2$, O, S, S=O, SO$_2$, N(R$^7$), P(R$^7$) and P(=O)R$^7$;

R$^5$ is, identically or differently on each occurrence, a H, D, a saturated or unsaturated, linear, branched or cyclic C$_{1-20}$-alkyl group, in which one or more H atoms is optionally replaced by D or F, or an aromatic or heteroaromatic ring system having 5 to 20 ring atoms, in which one or more H atoms is optionally replaced by F, and which is optionally substituted by one or more radicals R$^6$;

R$^6$ is, identically or differently on each occurrence, a H, D, F, Cl, Br, I, CHO, N(Ar$^1$)$_2$, C(=O)Ar$^1$, P(=O)(Ar$^1$)$_2$, S(=O)$_2$Ar$^1$, CR$^7$=CR$^7$Ar$^1$, CN, NO$_2$, Si(R$^7$)$_3$, B(OAr$^1$)$_2$, B(OR$^7$)$_2$, OSO$_2$R$^7$, OH, or a saturated or unsaturated, straight-chain, branched or cyclic C$_{1-40}$-alkyl group, C$_{1-40}$-alkoxy group or C$_{1-40}$-thioalkyl group, each of which is optionally substituted by one or more radicals R$^7$, where one or more non-adjacent CH$_2$ groups is optionally replaced by R$^7$C=CR$^7$, Si(R$^7$)$_2$, Ge(R$^7$)$_2$, Sn(R$^7$)$_2$, C=O, C=S, C=Se, C=NR$^7$, P(=O)(R$^7$), SO, SO$_2$, NR$^7$, O, S or CONR$^7$, and where one or more H atoms is optionally replaced by D, F, Cl, Br, I, CN or NO$_2$;

R$^7$ is identically or differently on each occurrence, a H, D, a saturated or unsaturated, linear, branched or cyclic C$_{1-20}$-alkyl group, in which one or more H atoms is optionally replaced by F or D, and an aromatic or heteroaromatic ring system having 5 to 20 ring atoms, in which one or more H atoms is optionally replaced by F or D;

m is, identically or differently on each occurrence, 0, 1, 2, 3 or 4, with the proviso that at least one index m is >0; and n is 1, 2, 3 or 4.

12. An electronic device which comprises the compound according to claim 1.

13. The electronic device as claimed in claim 12, wherein the device is an organic electroluminescent device (OLED, PLED), an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC) or an organic laser diode (O-laser).

14. An organic electroluminescent device which comprises the compound according to claim 1 is employed in an electron-transporting layer.

15. A formulation comprising at least one compound according to claim 1 and at least one solvent.

16. A compound of the following formula (1'):

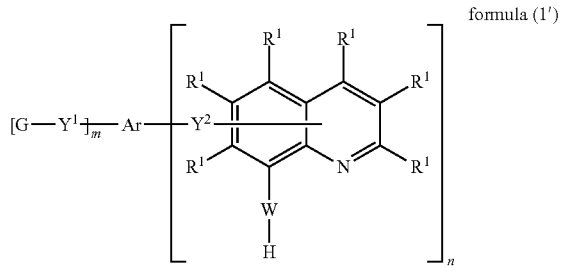

formula (1')

wherein

G is, identically or differently on each occurrence, a group of the following formula (a) or (b):

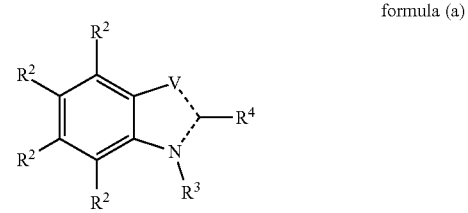

formula (a)

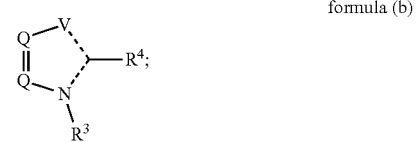

formula (b)

Q is, identically or differently on each occurrence, a N or CR$^3$,

V is selected from the group consisting of O, S, N, CR$^4$ and NR$^4$, with the proviso that, if V is equal to O, S or NR$^4$, R$^3$ represents a non-bonding electron pair;

the two dashed bonds in formula (a) and (b) mean that one of the bonds is a single covalent bond and the other is a double covalent bond;

R$^1$ is selected identically or differently on each occurrence, from the group defined for R$^2$, R$^3$ or R$^4$; where one R$^1$ is not present, and the quinoline unit is bonded to Y$^2$ at this position;

R$^2$, R$^3$ and R$^4$ are, identically or differently on each occurrence, a H, D, F, Cl, Br, I, CHO, N(Ar$^1$)$_2$, C(=O)Ar$^1$, P(=O)(Ar$^1$)$_2$, S(=O)Ar$^1$, S(=O)$_2$Ar$^1$, CR$^5$=CR$^5$Ar$^1$, CN, NO$_2$, Si(R$^5$)$_3$, B(OAr$^1$)$_2$, B(OR$^5$)$_2$, OSO$_2$R$^5$, OH, a saturated or unsaturated, straight-chain, branched or cyclic $C_{1-40}$-alkyl group, $C_{1-40}$-alkoxy group or $C_{1-40}$-thioalkyl group, each of which is optionally substituted by one or more radicals $R^5$, where one or more non-adjacent $CH_2$ groups is optionally replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$, and where one or more H atoms is optionally replaced by D, F, Cl, Br, I, CN or $NO_2$, an aromatic or heteroaromatic ring system having 5 to 60 aromatic ring atoms, which is optionally substituted by one or more radicals $R^6$, an aryloxy or heteroaryloxy group having 5 to 60 aromatic ring atoms, which is optionally substituted by one or more radicals $R^6$, and a combination of these systems; where one of the substituents $R^2$, $R^3$ or $R^4$ is not present on the group G, and the group G is bonded to $Y^1$ at this position;

W is, identically or differently on each occurrence, an O, S or $NR^B$, where $R^8$ is selected from the group defined for $R^2$, $R^3$ or $R^4$;

$Y^1$ and $Y^2$ are each, independently of one another, either not present, so that the groups bonded thereto are linked directly to one another by a single covalent bond, or are a saturated or unsaturated, linear, branched or cyclic $C_{1-40}$-alkyl group or an aromatic or heteroaromatic ring system having 5 to 60 ring atoms, which is optionally substituted by one or more radicals $R^6$;

Ar is an aromatic or heteroaromatic ring system having 5 to 60 aromatic ring atoms, which is optionally substituted by one or more radicals $R^9$, where $R^9$ is selected from the group defined for $R^2$, $R^3$ or $R^4$;

$Ar^1$ is, identically or differently on each occurrence, an aromatic or heteroaromatic ring system having 5 to 30 aromatic ring atoms, which is optionally substituted by one or more radicals $R^7$, where, in addition, two radicals $Ar^1$ which are bonded to the same nitrogen or phosphorus atom is optionally linked to one another by a single bond or a bridge selected from the group consisting of $B(R^7)$, $C(R^7)_2$, $Si(R^7)_2$, $C=O$, $C=NR^7$, $C=C(R^7)_2$, O, S, $S=O$, $SO_2$, $N(R^7)$, $P(R^7)$ and $P(=O)R^7$;

$R^5$ is, identically or differently on each occurrence, a H, D, a saturated or unsaturated, linear, branched or cyclic $C_{1-20}$-alkyl group, in which one or more H atoms is optionally replaced by D or F, or an aromatic or heteroaromatic ring system having 5 to 20 ring atoms, in which one or more H atoms is optionally replaced by F, and which is optionally substituted by one or more radicals $R^6$;

$R^6$ is, identically or differently on each occurrence, a H, D, F, Cl, Br, I, CHO, $N(Ar^1)_2$, $C(=O)Ar^1$, $P(=O)(Ar^1)_2$, $S(=O)Ar^1$, $S(=O)_2Ar^1$, $CR^7=CR^7Ar^1$, CN, $NO_2$, $Si(R^7)_3$, $B(OAr^1)_2$, $B(OR^7)_2$, $OSO_2R^7$, OH, or a saturated or unsaturated, straight-chain, branched or cyclic $C_{1-40}$-alkyl group, $C_{1-40}$-alkoxy group or $C_{1-40}$-thioalkyl group, each of which is optionally substituted by one or more radicals $R^7$, where one or more non-adjacent $CH_2$ groups is optionally replaced by $R^7C=CR^7$, $Si(R^7)_2$, $Ge(R^7)_2$, $Sn(R^7)_2$, $C=O$, $C=S$, $C=Se$, $C=NR^7$, $P(=O)(R^7)$, SO, $SO_2$, $NR^7$, O, S or $CONR^7$, and where one or more H atoms is optionally replaced by D, F, Cl, Br, I, CN or $NO_2$;

$R^7$ is identically or differently on each occurrence, a H, D, a saturated or unsaturated, linear, branched or cyclic $C_{1-20}$-alkyl group, in which one or more H atoms is optionally replaced by F or D, and an aromatic or heteroaromatic ring system having 5 to 20 ring atoms, in which one or more H atoms is optionally replaced by F or D;

m is, identically or differently on each occurrence, 0, 1, 2, 3 or 4, with the proviso that at least one index m is >0; and n is 1, 2, 3 or 4.

\* \* \* \* \*